(12) United States Patent
Wolf et al.

(10) Patent No.: US 7,888,509 B2
(45) Date of Patent: Feb. 15, 2011

(54) CHIRAL 1,8-DIARYLNAPHTHALENES, METHODS OF MAKING THEM, AND THEIR USE AS SENSORS

(75) Inventors: Christian Wolf, Arlington, VA (US); Xuefeng Mei, Arlington, VA (US)

(73) Assignee: Georgetown University, Washington, DC (US)

( * ) Notice: Subject to any disclaimer, the term of this patent is extended or adjusted under 35 U.S.C. 154(b) by 953 days.

(21) Appl. No.: 10/576,567

(22) PCT Filed: Nov. 1, 2004

(86) PCT No.: PCT/US2004/036409
§ 371 (c)(1),
(2), (4) Date: May 7, 2007

(87) PCT Pub. No.: WO2005/043124
PCT Pub. Date: May 12, 2005

(65) Prior Publication Data
US 2007/0276140 A1      Nov. 29, 2007

Related U.S. Application Data

(60) Provisional application No. 60/515,631, filed on Oct. 30, 2003.

(51) Int. Cl.
C07D 401/02      (2006.01)
C07D 215/02      (2006.01)
C07D 217/02      (2006.01)

(52) U.S. Cl. ................. 546/152; 544/180; 544/224; 544/242; 544/336; 546/102; 546/139; 546/153; 548/152; 548/217; 548/235; 548/247; 548/335.1; 548/577

(58) Field of Classification Search ................. None
See application file for complete search history.

(56) References Cited

U.S. PATENT DOCUMENTS 6,214,324 B1      4/2001      Candau et al.

OTHER PUBLICATIONS

Zoltewicz et al., Tetrahedron (1997), 53(15), pp. 5379-5388.*
Cross, W., et al.; "The Structure, Modelling and Dynamics of Hindered 5,6-Diarylacenaphthenes" J. Chem. Soc., Perkin Trans. 2 (2001) pp. 459-467.
Steele, M., et al.; "Attempts to Find a Solution to the Problem of Atropisomer Interconversion in 1,8-Diarylnaphthalenes and 5,6-Diarylacenaphthenes"; J. Chem. Soc., Perkin Trans. 1 (2001) pp. 588-598.
Thirsk, C., et al.; "The Structure, Modeling and Dynamics of 2,7-Diisopropoxy-1,8-diarylnaphthalenes"; J. Chem. Soc., Perkin Trans. 2 (2002) pp. 1510-1519.
Wolf, C. et al.; "Synthesis of Conformationally Stable 1,8-Diarylnaphthalenes: Development of New Photoluminescent Sensors for Ion-Selective Recognition" Journal of the American Chemical Society; (2003) vol. 125, No. 35, pp. 10651-10658.
International Search Report for PCT/US04/36409 , May 2005.

* cited by examiner

*Primary Examiner*—Zinna N Davis
(74) *Attorney, Agent, or Firm*—Foley Hoag, LLP

(57) ABSTRACT

One aspect of the invention relates to 1,8-diarylnaphthalene compounds. In certain embodiments, a compound of the invention is an N-oxide of a 1,8-diarylnaphthalene. In certain embodiments, the aryl group is an optionally substituted acridyl group. In certain embodiments, a compound of the invention is a single steroisomer. In certain embodiments, a compound of the invention is a single enantiomer. Another aspect of the present invention relates to a method of detecting the presence of an analyte in a sample by monitoring the fluorescence of a compound of the invention in a sample. In certain embodiments, the analyte is a metal ion. Another aspect of the present invention relates to a method of determining the enantiomeric purity of an analyte by monitoring the fluorescence of a compound of the invention in the presence of the analyte. In certain embodiments, the analyte is a compound that is capable of hydrogen bonding.

49 Claims, 48 Drawing Sheets anti-1        syn-1

Figure 4

| entry | [naphthalene with R,R] | stannane | Catalyst (mol%) | additives | yield of major product (%) |
|---|---|---|---|---|---|
| 1 | R = I | 12 | Pd(PPh$_3$)$_4$ (10)[a] | / | 14 + 15 (17) |
| 2 | R = I | 12 | Pd(PPh$_3$)$_4$ (10)[a] | Cy$_2$NMe | 14 + 15 (17) |
| 3 | R = Br | 12 | Pd(PPh$_3$)$_4$ (10)[b] | CuO | 3 (5) |
| 4 | R = Br | 12 | Pd(PPh$_3$)$_4$ (10)[c] | CuO | 3 (5) |
| 5 | R = Br | 12 | Pd(PPh$_3$)$_4$ (10)[a] | CuO | 3 (10) |
| 6 | R = Br | 12 | Pd(PPh$_3$)$_4$ (20)[a] | CuO | 3 (18) |
| 7 | R = Br | 12 | Pd(PPh$_3$)$_4$ (30)[a] | CuO | 3 (25) |
| 8 | R = Br | 12 | Pd(PPh$_3$)$_4$ (40)[a] | CuO | 3 (25) |
| 9 | R = Br | 12 | Pd(PPh$_3$)$_4$ (50)[a] | CuO | 3 (25) |
| 10 | R = Br | 11 | Pd(PPh$_3$)$_4$ (30)[a] | CuO | 2 (25) |

18: R=Me
19: R=Ph

20: R=Me
21: R=Ph

Figure 26
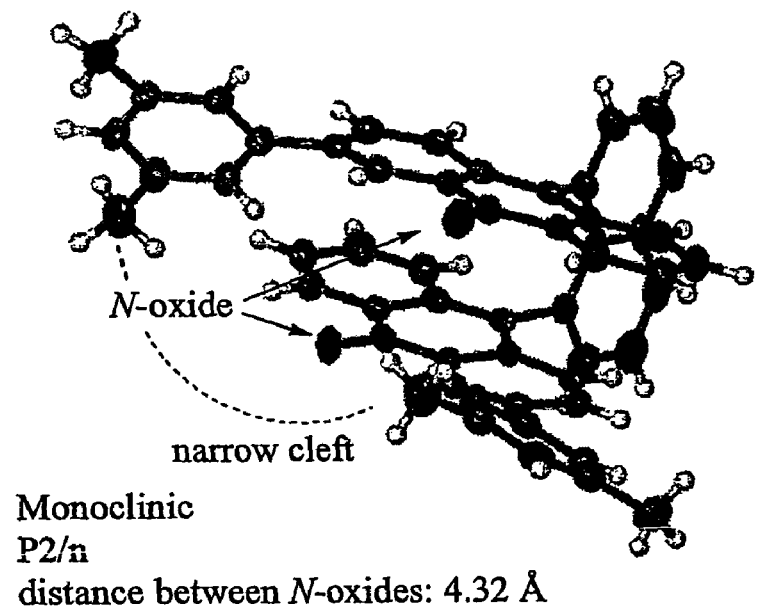
Monoclinic
P2/n
distance between N-oxides: 4.32 Å
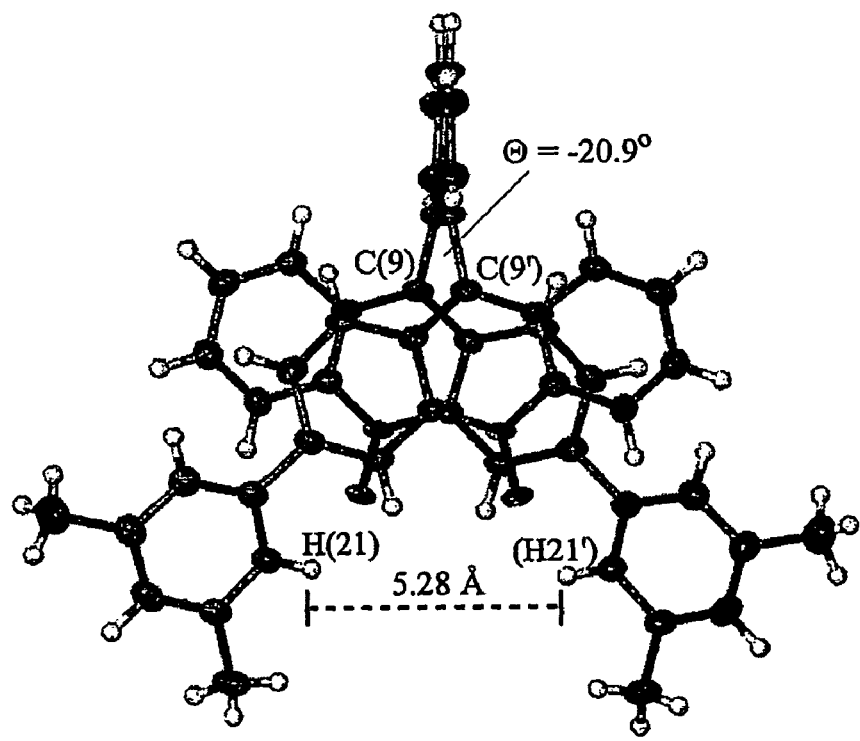

Figure 27
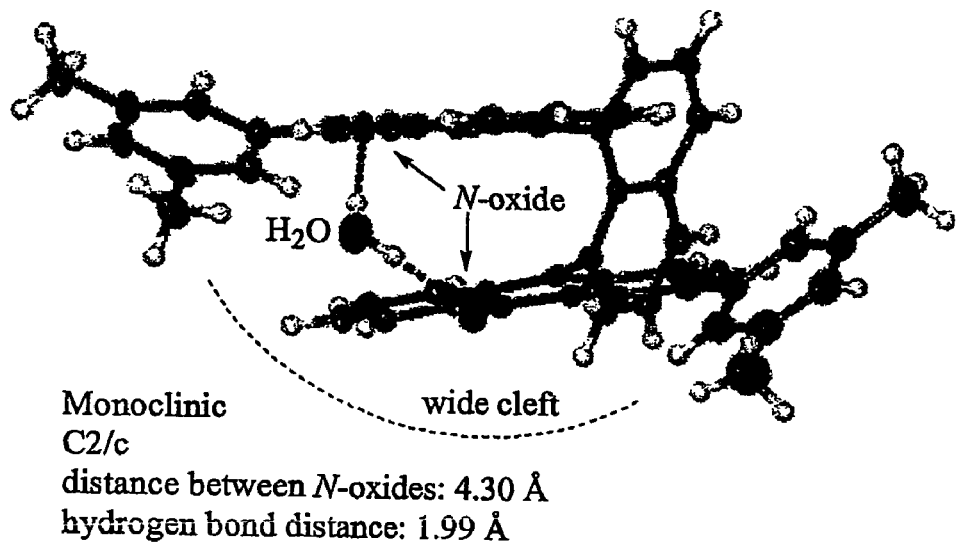
Monoclinic
C2/c
distance between *N*-oxides: 4.30 Å
hydrogen bond distance: 1.99 Å
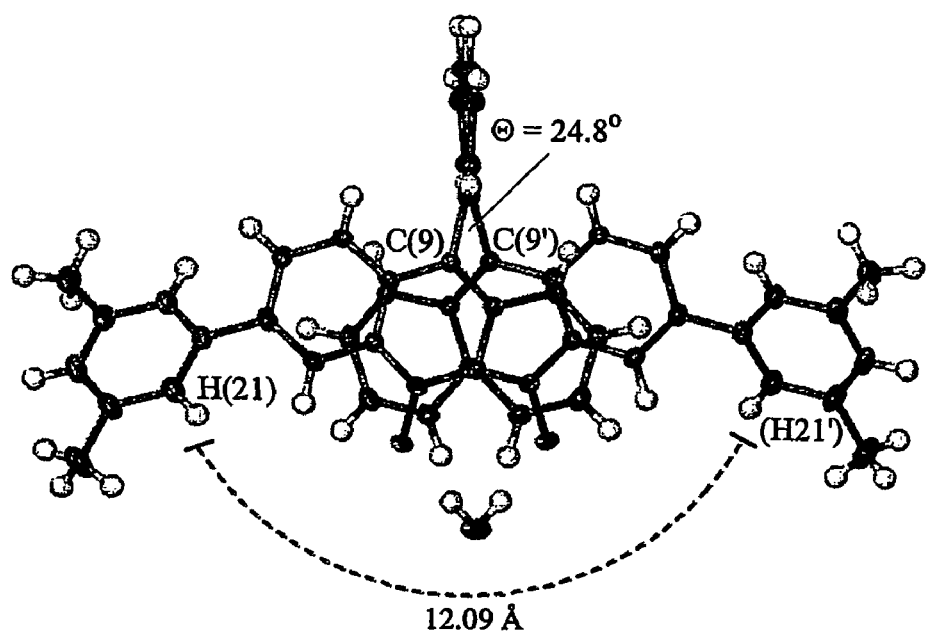

Figure 28

| complex: | 33-H$_2$O-CH$_3$CN | 33-CH$_2$Cl$_2$ |
|---|---|---|
| empirical formula | C28 H23 N2 O1.50 | C27 H21 Cl2 N O |
| formula weight | 411.48 | 446.35 |
| temperature | 186(2) K | 183(2) K |
| wavelength | 0.71073 Å | 0.71073 Å |
| crystal system | Monoclinic | Monoclinic |
| space group | C2/c | P2/n |
| unit cell dimensions | a = 24.551(2) Å | a = 13.839(2) Å |
| | b = 13.3883(12) Å | b = 11.2871(18) Å |
| | c = 13.7187(12) Å | c = 15.055(3) Å  γ = 90° |
| | α = 90° | α = 90° |
| | β = 107.204(2)° | β = 113.991(3)° |
| | γ = 90° | γ = 90° |
| distance O-O | 4.32 Å | 4.30 Å |
| distance N-N | 3.84 Å | 3.82 Å |
| distance C(9)-C(9') | 2.87 Å | 2.91 Å |
| distance H(21)-H(21') | 12.09 Å | 5.28 Å |
| torsion Θ between acridyl rings | 24.8° | -20.9° |
| Volume | 4307.5(7) Å$^3$ | 2148.4(6) Å$^3$ |
| Z | 8 | 4 |
| density (calculated) | 1.269 Mg/m$^3$ | 1.380 Mg/m$^3$ |
| Absorption coefficient | 0.079 mm$^{-1}$ | 0.322 mm$^{-1}$ |
| F(000) | 1736 | 928 |
| crystal size | 0.95 x 0.46 x 0.46 mm$^3$ | 0.50 x 0.30 x 0.20 mm$^3$ |
| theta range for data collection | 1.74 to 27.00°. | 1.69 to 25.00°. |
| index ranges | -31<=h<=31, -16<=k<=17, -17<=l<=17 | -16<=h<=15, -13<=k<=10, -17<=l<=17 |
| Reflections collected | 18167 | 10895 |
| independent reflections | 4690 [R(int) = 0.0368] | 3798 [R(int) = 0.0654] |
| completeness to theta = 27.00° | 99.8 % | 99.9 % |
| max. and min. transmission | 0.9647 and 0.9289 | 0.9383 and 0.8554 |
| refinement method | Full-matrix least-squares on F$^2$ | Full-matrix least-squares on F$^2$ |
| data / restraints / parameters | 4690 / 0 / 292 | 3798 / 0 / 283 |
| goodness-of-fit on F$^2$ | 1.090 | 0.875 |
| final R indices [I>2sigma(I)] | R1 = 0.0568, wR2 = 0.1498 | R1 = 0.0539, wR2 = 0.1284 |
| largest diff. peak and hole | 0.610 and -0.467 e.Å$^{-3}$ | 0.279 and -0.345 e.Å$^{-3}$ |

Figure 45

| analyte | ratio (32/analyte) | α | $K_{(+)-1-(R)-analyte}^{a}$ | $K_{(+)-1-(S)-analyte}^{a}$ |
|---|---|---|---|---|
| A | 1:1 | 1.7 (R/S) | 88.5 M$^{-1}$ | 56.5 M$^{-1}$ |
| B | 1:1 | 1.3 (S/R) | 610.0 M$^{-1}$ | 840.0 M$^{-1}$ |
| C | 1:1 | 2.2 (S/R) | 75.6 M$^{-1}$ | 241.3 M$^{-1}$ |
| D | 1:1 | 1.1 (S/R) | 18.4 M$^{-1}$ | 20.0 M$^{-1}$ |
| E | 1:2 | 2.1 (S/R) | 2100.0 M$^{-2}$ | 4900.0 M$^{-2}$ |
| F | 1:2 | 2.2 (R/S) | 16000.0 M$^{-2}$ | 7100.0 M$^{-2}$ |
| G | 1:2 | 1.3 (R/S) | 5300.0 M$^{-2}$ | 4700.0 M$^{-2}$ |
| H | 1:2 | 4.5 (R/S) | 63000.0 M$^{-2}$ | 36000.0 M$^{-2}$ |

[a]Obtained using the Benesi-Hildebrand equation for 1:1 complexes (A-D) and 1:2 complexes (E-H).

Figure 46

| complex: | 32 | |
|---|---|---|
| Empirical formula | $C_{52}H_{38}N_2$ | |
| Formula weight | 690.84 | |
| Temperature | 173(2) K | |
| Wavelength | 0.71073 Å | |
| Crystal system | Monoclinic | |
| Space group | C2/c | |
| Unit cell dimensions | a = 16.1895(13) Å | α= 90°. |
| | b = 10.3998(9) Å | β= 92.680(2)°. |
| | c = 21.2941(18) Å | γ = 90°. |
| Volume | 3581.3(5) Å$^3$ | |
| Z | 4 | |
| Density (calculated) | 1.281 mg/m$^3$ | |
| Absorption coefficient | 0.074 mm$^{-1}$ | |
| F(000) | 1456 | |
| Crystal size | 0.30 x 0.20 x 0.10 mm$^3$ | |
| Theta range for data collection | 1.91 to 24.99°. | |
| Index ranges | -19<=h<=19, -12<=k<=12, -25<=l<=25 | |
| Reflections collected | 13111 | |
| Independent reflections | 3166 [R(int) = 0.0375] | |
| Completeness to theta = 24.99° | 100.0 % | |
| Absorption correction | Multiscan | |
| Max. and min. transmission | 0.9927 and 0.9782 | |
| Refinement method | Full-matrix least-squares on F$^2$ | |
| Data / restraints / parameters | 3166 / 0 / 247 | |
| Goodness-of-fit on F$^2$ | 1.087 | |
| Final R indices [I>2sigma(I)] | R1 = 0.0485, wR2 = 0.1122 | |
| R indices (all data) | R1 = 0.0697, wR2 = 0.1190 | |
| Largest diff. peak and hole | 0.182 and -0.147 e.Å$^{-3}$ | |

Figure 48

| % (*R*) | I | $I_0/I$ |
|---|---|---|
| 0 | 70354 | 2.324019 |
| 10 | 61948 | 2.639375 |
| 20 | 56011 | 2.919141 |
| 30 | 52849 | 3.093796 |
| 40 | 47734 | 3.425315 |
| 50 | 41878 | 3.904293 |
| 60 | 35989 | 4.543166 |
| 70 | 32725 | 4.996303 |
| 80 | 31520 | 5.18731 |
| 90 | 29509 | 5.540818 |
| 100 | 25983 | 6.29273 | note: $I_0$ was 163504.

CHIRAL 1,8-DIARYLNAPHTHALENES, METHODS OF MAKING THEM, AND THEIR USE AS SENSORS

GOVERNMENT SUPPORT

The invention was made with support provided by the National Science Foundation (Grant No. CHE-0347368). Therefore, the government has certain rights in the invention.

RELATED APPLICATIONS

This application claims the benefit of priority to Patent Cooperation Treaty Application number PCT/US2004/036409, filed Nov. 1, 2004; which claims the benefit of priority to U.S. Provisional Patent Application Ser. No. 60/515,631, filed Oct. 30, 2003.

BACKGROUND OF THE INVENTION

Chemical sensors are highly useful in the chemical and pharmaceutical industry. Chemical sensors are used to determine the concentration in biological samples of metal ions, such as calcium, and important gases, such as NO, $O_2$, and $CO_2$. For example, sensors are used to determine the level of calcium ions (Ca(II)) in the blood of animals. In addition, chemical sensors are important in the development of analytical techniques to measure the enantiomeric purity of chiral compounds. Analytical techniques to determine enantiomeric purity are important to the pharmaceutical industry because many biologically active compounds are single enantiomers.

In general, a chemical sensor consists of a receptor and a transducer. The receptor selectively binds the analyte while the transducer generates a signal based on the change in a chemical parameter that occurs in response to analyte binding. The sensitivity of the sensor is defined by the minimum amount of analyte that induces an identifiable signal relative to the noise. The selectivity of the sensor corresponds to its capacity to distinguish the analyte from the other chemical species which may be present in the medium. A very selective sensor is distinguished by the fact that the signal induced by the presence of the analyte is much more intense than the signal induced by any other chemical species present in the same amount. One of the main difficulties encountered in this field is to prepare sensors which are both sensitive and highly selective.

Recently, there has been an increasing interest in the development of practical, sensitive and miniaturzed probe systems for use in monitoring metal ions in biological media, living cells, and environmental samples. Fluorescence based sensors are especially useful due to their sensitivity, achieving attomole ($10^{-8}$ mole) detection limits. Such sensors often use probes that have chemical reagents or bioreceptors (such as an antibody) chemically bound to optical fibers or physically entrapped in sensing microcavities containing liquid reagents or gels attached to the distal end or to the cladding of the optical fiber. Direct attachment allows fast response time since sensor response depends on the mass transfer rate of the analyte to the immobilized reagent. In some cases, gels may be saturated with large quantities of reagent in order to enhance the sensitivity of the sensor. Physical entrapment onto the probe can also be another form of immobilization that is suitable to chemical or biological reagents. Immobilization on cellulose or poly(vinyl chloride) films allows greater loading, but decreases response time because the reagent is immobilized in single layers.

Several chemical sensors have been developed for the detection of metal ions. One of the first fluorescent calcium indicators was 2-{[2-[bis(carboxymethyl)amino]-5'-methylphenoxy]methyl}-6-methoxy-8-[bis(carboxymethyl)amino]quinoline (Quin-2). See R. Y. Tsien *Biochemistry* 1980, 19, 2396. Calcium binding to this sensor elicits an increase of fluorescence intensity of this compound. In comparison, Mauze et al. describe a chemical sensor comprising 2,2-bis(3,4-(15-crown-5)-2-nitrophenylcarbamoxymethyl) tetradecanol-14 which has at least one binding site and is provided with a fluorophore such as Rhodamine-B at that binding site. See U.S. Pat. No. 5,154,890. The sensing material is immobilized in a gel of polyacrylamide. U.S. Pat. No. 5,176,882 teaches a dual fiberoptic cell for multiple serum measurements where both a gas and an ion are analyzed simultaneously using a single probe having two separate fiber optic sensors incorporated therein. The gas is detected by the color change of a dye and the ion is detected by the fluorescing of a fluorescent metal ion sensitive dye. Nevertheless, sensors which have been developed to this point have several deficiencies, including low sensitivity due to weak analytical signal, low selectivity due to interferences, long term instability because of degradation of the immobilized reagent or its desorptive loss from the support, and/or slow response time because of barriers to mass transport in the polymer support.

Analytical methods to measure enantiomeric purity are needed because many biologically active compounds, such as pharmaceuticals, agrochemicals, flavors, and nutrients, are chiral. In fact, more than 50% of today's top-selling drugs are single enantiomers. The increasing demand for enantiopure chemicals has been accompanied by significant progress in asymmetric synthesis and catalysis. See (a) Helmchen, G.; Hoffmann, R. W.; Mulzer, J.; Schaumann, E. (Eds.) "Stereoselective Synthesis" in "Methods of Organic Chemistry", Houben-Weyl, Vol. 21a-21f, 4th edition, Thieme, Stuttgart, 1995; (b) Gawley, R. E. Aubé, J. "Principles of Asymmetric Synthesis" Tetrahedron Organic Chemistry Series, Elsevier, N.Y., 1996; (c) Ho, T.-L. "Stereoselectivity in Synthesis" Wiley-VCH, New York, 1999; (d) Jonathan, M. J. W. "Catalysis in Asymmetric Synthesis" Sheffield Academic Press, Sheffield, 1999; and (e) Ojima, I.; (Ed.) "Catalytic Asymmetric Synthesis" 2nd edition, Wiley-VCH, New York, 2000. In addition, many analytical techniques, such as chiroptical methods, NMR spectroscopy, mass spectrometry, electrophoresis, and chromatography using chiral stationary phases, have been developed for the determination of the enantiomeric purity of chiral compounds. See Eliel, E. L.; Wilen, S. H. "Stereochemistry of Organic Compounds" John Wiley and Sons, New York, 1994, pp. 214-274.

Stereoselective analysis is very important to verify the purity and stereochemical stability of chiral chemicals and drugs. It also plays an integral part in the development of new asymmetric reactions. Recently, high-throughput screening (HTS) methods based on chiral chromatography for fast evaluation of enantioselective catalysts have been developed. See Wolf, C.; Hawes, P. A. *J. Org. Chem.* 2002, 67, 2727-2729; Wolf, C.; Francis, C. J.; Hawes, P. A.; Shah, M. *Tetrahedron: Asymm.* 2002, 13, 1733-1741; and Duursma, A.; Minnaard, A. J.; Fering a, B. L. *Tetrahedron* 2002, 58, 5773-5778. It has been demonstrated that multi-substrate screening followed by chromatography can provide yields, stereoselectivity, catalytic activity, chiral induction, and substrate tolerance of a catalyst in a single experiment. However, employing chromatography in HTS is usually too time-consuming, i.e. individual substrate screening combined with real-time enantioselective analysis seems to be a more promising approach.

Routine analysis of the enantiomeric composition of a sample usually entails chiral chromatography using expensive GC or HPLC columns, chiroptical methods, electrophoresis with chiral additives or NMR spectroscopy with chiral shift reagents. Enantioselective sensing based on fluorescence spectroscopy offers a variety of advantages over these techniques including different detection modes (fluorescence quenching, enhancement, and lifetime), high sensitivity, low cost of instrumentation, waste reduction, time efficiency, and the possibility of performing real-time analysis. Because of the high sensitivity inherent to fluorescence spectroscopy only a very small amount of the sensor is required, which makes this technique more cost-effective and practicable than chromatography. To date, only a few enantioselective fluorescence sensors including chiral macrocycles, dendrimers, or oligomers have been reported. See Lin, J.; Hu, Q.-S.; Xu, M.-H.; Pu, L. *J. Am. Chem. Soc.* 2002, 124, 2088-2089; Lee, S. J.; Lin, W. *J. Am. Chem. Soc.* 2002, 124, 4554-4555; Xu, M.-H.; Lin, J.; Hu, Q.-S.; Pu, L. *J. Am. Chem. Soc.* 2002, 124, 14239-14246; and Ma, L.; White, P. S.; Lin, W. *J. Org. Chem.* 2002, 67, 7577-7586.

Enantioselectivity in energy transfer reactions between a variety of chiral quencher molecules and photoexcited chiral Lanthamide chelates has also been observed by time-resolved or steady-state circularly polarized luminescence measurements. See Meskers, S. C. J.; Dekkers, H. P. J. M. *J. Am. Chem. Soc.* 1998, 120, 6413-6414 and Meskers, S. C. J.; Dekkers, P. J. M. *J. Phys. Chem. A* 2001, 105, 4589-4599. Nevertheless, the development of enantioselective sensing to a broadly applicable technique requires the design of new selector molecules combining well-defined stereoselective recognition of various classes of compounds with the advantage of fluorescence detection.

SUMMARY OF THE INVENTION

One aspect of the invention relates to 1,8-diarylnaphthalene compounds. In certain embodiments, the aryl group is an optionally substituted acridyl group. In a preferred embodiment, the acridyl group is substituted with a methyl, isopropyl, or 3,5-methylphenyl group. In a preferred embodiment, the compound of the invention is a single steroisomer. In certain embodiments, the compounds of the invention relate to the N-oxide of a 1,8-diacridylnaphthalene. In a preferred embodiment, the acridyl group is substituted with 3,5-methylphenyl group. In a preferred embodiment, the N-oxide compound of the invention is a single enantiomer.

Another aspect of the present invention relates to a method of detecting the presence of an analyte by monitoring the fluorescence of the compound of the invention in the presence of the analyte. In certain embodiments, the analyte is a metal ion. In a preferred embodiment, the analyte is $Cu^{2+}$.

Another aspect of the present invention relates to a method of determining the enantiomeric purity of an analyte by monitoring the fluorescence of the compound of the invention in the presence of the analyte. In certain embodiments, the analyte is a compound that is capable of hydrogen bonding. In a preferred embodiment, the analyte is a compound containing a hydroxyl, carboxylic acid, or amine functional group.

BRIEF DESCRIPTION OF FIGURES

FIG. 4 depicts optimized results of the Pd-catalyzed cross-coupling reactions ([a]DMF, 140° C., 18 h; [b]DMF, 100° C., 18 h [c]DMF, 140° C., 5 h).

FIG. 26 depicts a side view (top) and view along the naphthalene plane (bottom) of the X-ray structure of 33 (closed structure). Co-crystallizing dichloromethane is omitted for clarity.

FIG. 27 depicts a side view (top) and view along the naphthalene plane (bottom) of the X-ray structure of 33-H$_2$O (open structure). Co-crystallizing acetonitrile is omitted for clarity.

FIG. 28 depicts crystal data and structure refinement for single crystals of N,N'-dioxide 16.

FIG. 45 depicts enantioselective fluorescence quenching of (+)-32 in the presence of carboxylic acids A-H.

FIG. 46 depicts crystal data and structure refinement for single crystals of 32.

FIG. 48 depicts fluorescence quenching of 32 in the presence of H measured for calibration.

DETAILED DESCRIPTION OF THE INVENTION

Background and Design of 1,8-Diarylnaphthalene Sensors

Figure 1:
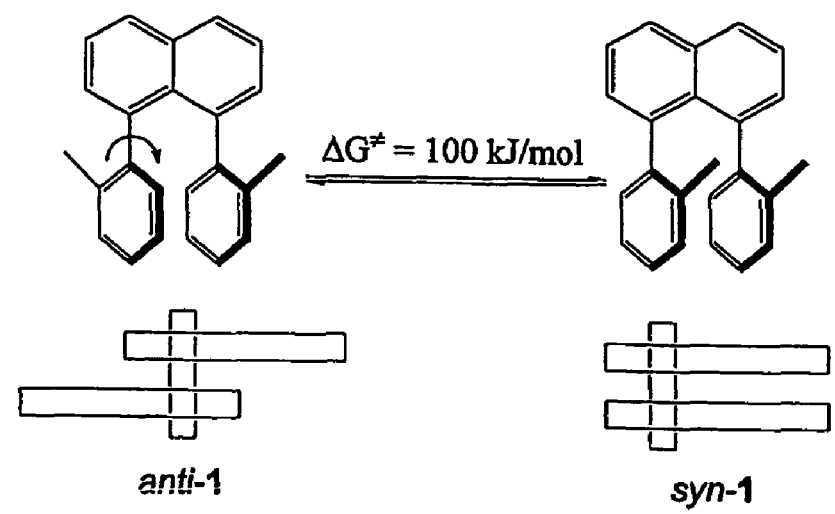
FIG. 1 depicts the structure of 1 exhibiting antiparallel (anti-isomer) or parallel (syn-isomer) 2-methylphenyl moieties.

The unique stereochemical, electronic, and photochemical properties of sterically congested aromatic compounds have attracted considerable attention during recent years because they afford promising optoelectronic devices, rotors, and chemical sensors. See Wong, K-T.; Chien, Y.-Y.; Chen, R.-T.; Wang, C.-F.; Lin, Y.-T.; Chiang, H.-H.; Hsieh, P.-Y.; Wu, C.-C.; Chou, C. H.; Su, Y. O.; Lee, G.-H.; Peng, S.-M. *J. Am. Chem. Soc.* 2002, 124, 11576-11577 and Rathore, R.; Deselnicu, M. I.; Burns, C. L. *J. Am. Chem. Soc.* 2002, 124, 14832-14833. The preparation of conformationally stable 1,8-diarylnaphthalenes has been an unresolved challenge since Clough and Roberts reported the synthesis of atropisomeric 1,8-bis(2,2'-dimethyl-1,1'-diphenyl)naphthalene, 1, almost 30 years ago, FIG. 1. Clough, R. L.; Roberts, J. D. *J. Am. Chem. Soc.* 1976, 98, 1018-1020. Exhibiting an energy barrier to isomerization of 100 kJ/mol, 1 remains the most stable atropisomer of this class of compounds reported to date.

Despite the variety of cross-coupling procedures that has been developed for the synthesis of biaryls in recent years, coupling reactions using highly hindered aromatic compounds has rarely been achieved. Yin, J.; Rainka, M. P.; Zhang, X.-X.; Buchwald, S. L *J. Am. Chem. Soc.* 2002, 124, 1162-1163 and references therein. A number of aryl and hetaryl groups have been introduced into the peri-positions of naphthalene by us and others to study the energy barrier to rotation about the naphthyl-aryl bond. Incorporation of ortho- or meta-substituted aryl moieties into both peri-positions of naphthalene results in two chiral anti-isomers and one meso syn-isomer. See (a) Cozzi, F.; Ponzini, F.; Annunziata, R.; Cinquini, M.; Siegel, J. S. *Angew. Chem. Int. Ed. Engl.* 1995, 34, 1019-1020; (b) Ernst, L.; Sakhaii, P. *Magn. Reson. Chem.* 2000, 38, 559-565; (c) Wolf, C.; Ghebremariam, B. T. *Tetrahedron: Asymm.* 2002, 13, 1153-1156; and (d) Wolf, C.; Tumambac, G. E. *J. Phys. Chem. A* 2003, 107, 815-817.

Computational studies and x-ray analysis have shown that the peri-aryl rings are coplanar and almost perpendicular to the naphthalene moiety in the ground state. In contrast to the significant steric hindrance to isomerization suggested by CPK models, 1,8-diarylnaphthalenes such as 1 are not stable to interconversion at room temperature. The development of a synthetic route toward conformationally stable, atropisomeric 1,8-diarylnaphthalenes would facilitate studies of intramolecular interactions between stacked aryl groups and has been considered an entry to a new class of chiral ligands for asymmetric catalysis. See Sinnokrot, M. O.; Valeev, E. F.; Sherrill, C. D. *J. Am. Chem. Soc.* 2002, 124, 10887-10893 and Steele, M.; Watkinson, M.; Whiting, A. *J. Chem. Soc., Perkin Trans.* 1 2001, 588-598.

To date, all attempts to prepare 1,8-diarylnaphthalenes exhibiting conformational stability have been unsuccessful because of the severe steric repulsion that one can expect during the construction of such a highly constrained framework. Based on ab initio calculations, Thirsk et al. recently predicted a rotational energy barrier of approximately 160 kJ/mol to isomerization for ortho-substituted 2,7-diisopropoxy-1,8-diarylnaphthalenes. However, their attempts to synthesize such conformationally stable atropisomers using Suzuki cross-coupling were not successful. Thirsk, C.; Hawkes, G. E.; Kroemer, R. T.; Liedl, K. R.; Loertig, T.; Nasser, R.; Pritchard, R. G.; Steele, M.; Warren, J. E.; Whiting, A. *J. Chem. Soc., Perkin Trans.* 2 2002, 1510-1519.

We assumed that introduction of acridyl moieties into the peri-positions of naphthalene would result in a rigid scaffold that renders rotation of the aryl rings about the acridyl-naphthalene axis impossible. Careful incorporation of substitutents into the fluorescent acridyl rings was expected to afford bidentate selectors exhibiting well-defined pockets for coordination to Lewis or Bronsted acids. Selective interactions between this new class of chemosensors and metal ions or other substrates would be measurable by sensitive fluorescence spectroscopy and allow real-time monitoring of trace analytes. Although a variety of fluorescent sensors for alkali, alkaline earth, and transition metals have been developed, high ion selectivity and the ability to differentiate between different oxidation states remain a challenge. See Zheng, Y.; Gattas-Asfura, K. M.; Li, C.; Andreopoulos, F. M.; Pham, S. M.; Leblanc, R. M. *J. Phys. Chem. B* 2003, 107, 483-488 and Kim, J. S.; Noh, K. H.; Lee, S. H.; Kim, S. K.; Kim, S. K.; Yoon, J. *J. Org. Chem.* 2003, 68, 597-600.

The present invention generally relates to molecules that may be used as sensors to detect chiral compounds, metal ions, or biopolymers such as RNA or DNA. In certain embodiments, the compounds of the invention may be useful as Lewis acidic or Lewis basic catalysts. We have discovered the first synthetic route to 1,8-dihetarylnaphthalenes exhibiting conformational stability, i.e., hindered rotation about the hetaryl-naphthalene bond at high temperature. We obtained, purified and separated all possible isomers, i.e., the meso-syn isomer as well as enantiopure anti-isomers. We have discovered selector molecules that can differentiate between enantiomers of a broad range of classes of chiral compounds, including but not limited to amines amino acids and alcohols. The 1,8-diacridylnaphthalenes also show selectivity for various metal ions. We have discovered that 1,8-diacridylnaphthalenes may be used for the analysis of small amounts of metal ions and chiral compounds using fluorescence or NMR spectroscopy. Remarkably, 1,8-diacridylnaphthalenes are also useful in asymmetric catalysis, determination of the absolute configuration of a stereogenic center in a compound, and selective interactions with RNA or DNA sequences.

Synthesis of 1,8-Diarylnaphthalenes

Figure 2:
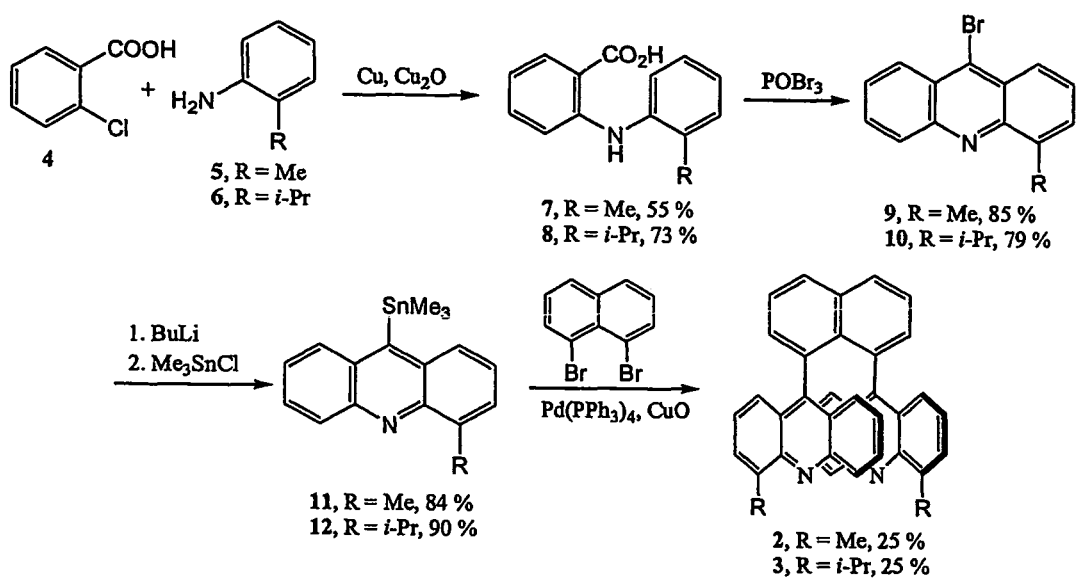
FIG. 2 depicts the synthesis of 1,8-diacridylnaphthalenes 2 and 3.
Figure 38:
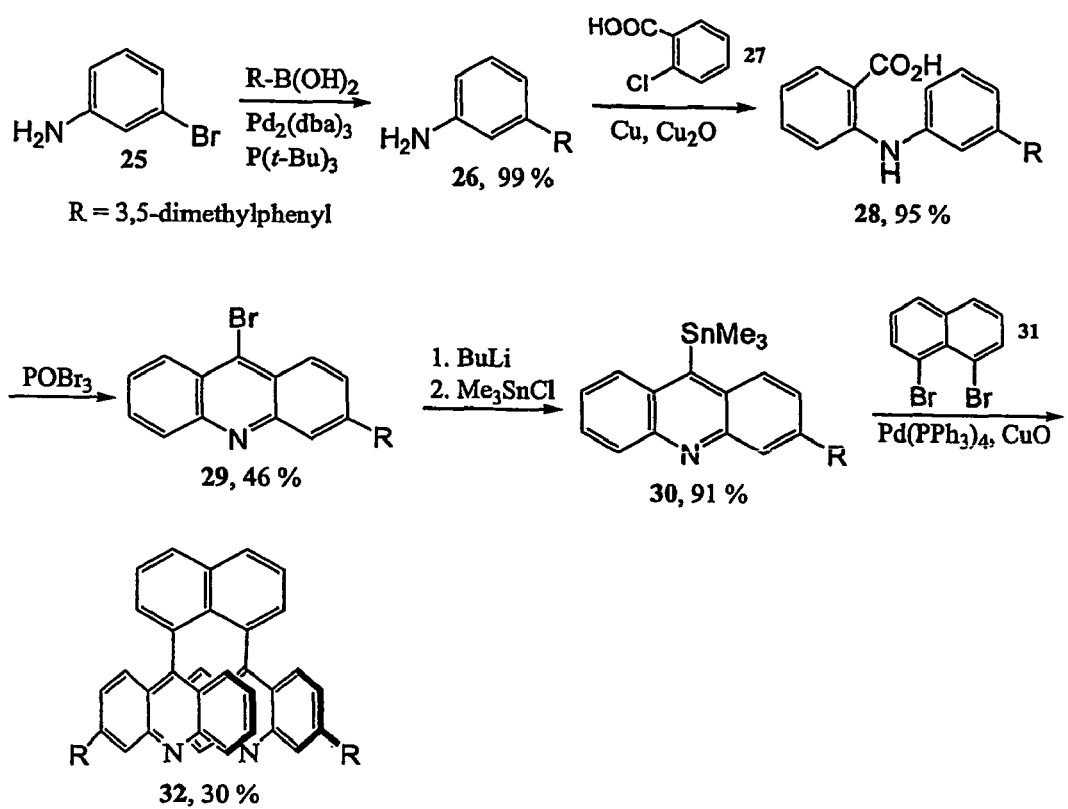
FIG. 38 depicts the synthesis of 1,8-diacridylnaphthalene 32.

The synthesis of 1,8-diarylnaphthalenes is depicted in FIG. 2 and FIG. 38. FIG. 2 depicts the synthesis of 1,8-bis(4,4'-dimethyl-9,9'-diacridyl)naphthalene (2). Retrosynthetic analysis of 1,8-bis(4,4'-dimethyl-9,9'-diacridyl)naphthalene (2) and 1,8-bis(4,4'-diisopropyl-9,9'-diacridyl)naphthalene (3) suggested Stille or Suzuki cross-coupling of 1,8-dibromo- or 1,8-diiodonaphthalene with a 4-substituted-9-acridyl stannane or boronic acid derivative, which can be formed via ring construction from 2-substituted anilines. We have found that 1,8-bis(4,4'-dialkyl-9,9'-diacridyl)naphthalenes 2 and 3 can be synthesized from readily available 2-chlorobenzoic acid, 4, and anilines 5 and 6, respectively.

Figure 3:
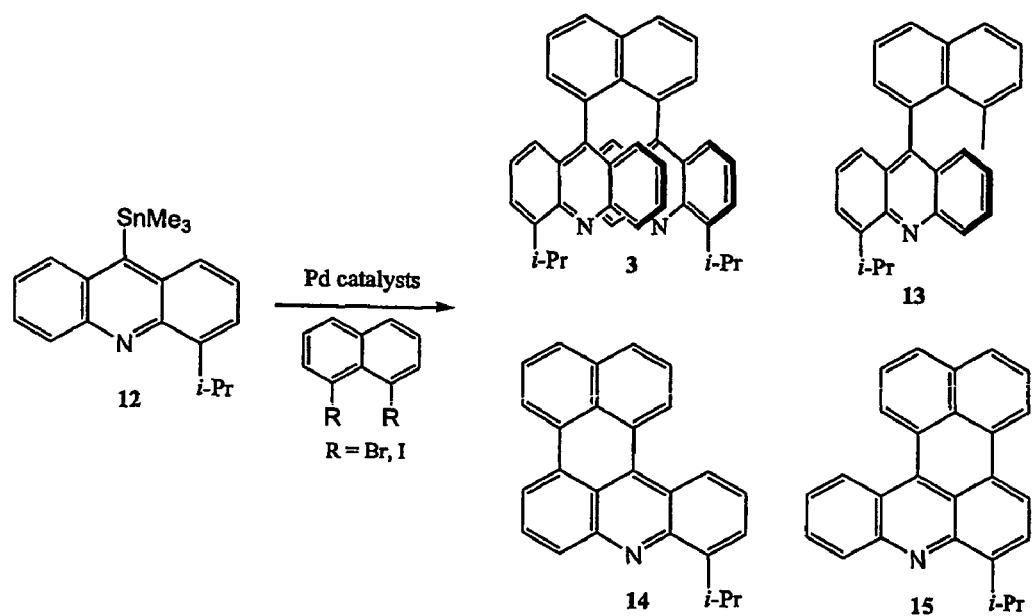
FIG. 3 depicts Stille cross-coupling products obtained from stannane 12 and 1,8-dihalonaphthalenes.

Commercially available acid, 4, was converted to 4-alkyl-9-trimethylstannylacridine, 11 and 12, in 3 steps with high overall yield. First, we attempted Stille cross-coupling of stannane 12 and 1,8-diiodonaphthalene using Pd(PPh$_3$)$_4$ as the catalysts. However, 14 and 15 were obtained as the only cross-coupling products in addition to degradation products of stannane 11, FIG. 3. The structure of 14 and 15 was determined by NMR and LC/APCI/MS.

We therefore decided to use 1,8-dibromonaphthalene in the Stille reaction. See Seyferth, D.; Vick, S. C. *J. Organomet. Chem.* 1977, 141, 178-187. Screening of various catalysts such as Pd(PPh$_3$)$_4$, PdCl$_2$dppf or Pd$_2$(dba)$_3$/t-Bu$_3$P and optimization of reaction conditions revealed that employing Pd(PPh$_3$)$_4$ and CuO in DMF at 140° C. affords 1,8-bis(4,4'-dialkyl-9,9'-diacridyl)naphthalenes 2 and 3 via Stille coupling of stannanes 11 or 12 with 1,8-dibromonaphthalene in remarkable yields. We were pleased to find less than 10% of coupling by-products 13, 14 and 15 under these conditions, FIG. 4. Notably, Suzuki coupling of 1,8-dibromonaphthalene and 4-isopropoyl-9-acridylboronic acid or its pinacolate derivative employing Pd(PPh$_3$)$_4$, PdCl$_2$dppf or Pd$_2$(dba)$_3$/t-Bu$_3$P as the catalyst as well as t-BuOK, K$_3$PO$_4$ or Cs$_2$CO$_3$ as the base in DME and DMF, respectively, did not result in the formation of the desired coupling product.

Figure 5:
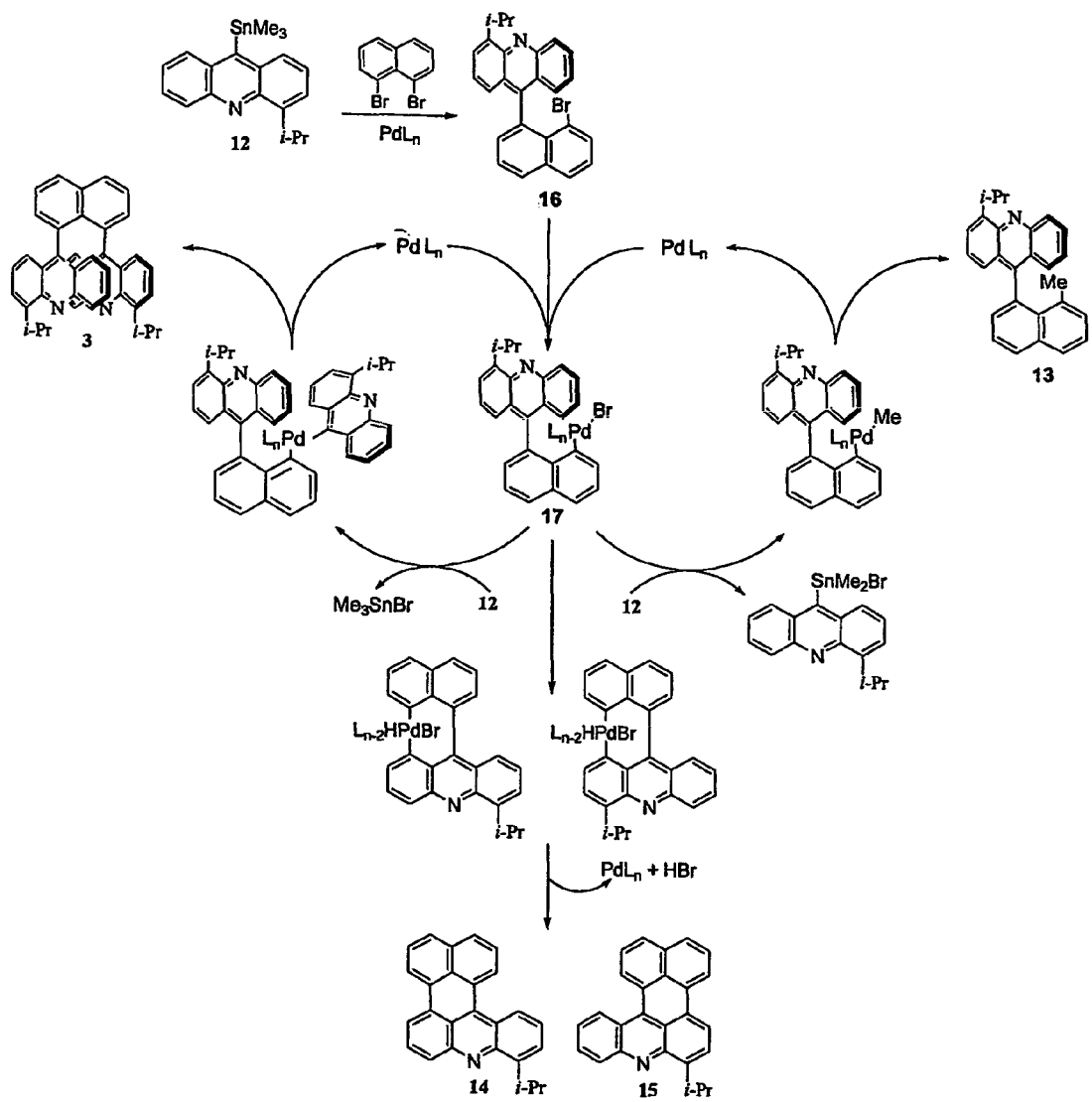
FIG. 5 depicts possible transmetallation pathways during the second catalytic cycle of the Pd-catalyzed Stille coupling of 1-(4-isopropyl-9-acridyl)-8-bromonaphthalene, 16, and stannane 12.

The observed cross-coupling by-products are indicative of the steric hindrance that occurs during the Pd-catalyzed reaction between the intermediate 1-(4-isopropyl-9-acridyl)-8-bromonaphthalene, 16, and another stannane 12, FIG. 5. Oxidative addition of 16 to the Pd catalysts provides a reactive Pd complex 17 that can undergo transetallation followed by reductive elimination to yield Stille products 3 and 13 or intramolecular coupling through Pd-activation of a peri acridyl C—H bond to form 14 and 15. The formation of carbon-carbon bonds via metal-mediated C—H bond activation has been reported by others and used as a powerful strategy for the synthesis of complex compounds. See (a) Dyker, G. *Angew. Chem., Int. Ed. Engl.* 1994, 33, 103-105; (b) Reetz; M. T.; Wanninger, K; Hermes, M. *J. Chem. Soc. Chem. Commun.* 1997, 535-536; (c) Jia, C.; Kitamura, T.; Fujiwara, Y.; *Acc. Chem. Res.* 2001, 34, 633-639; (d) Ritleng, V.; Sirlin, C.; Pfeffer, M. *Chem. Rev.* 2002, 102, 1731-1769; and (e) Dangel, B. D.; Godula, K.; Youn, S. W.; Sezen, B.; Sames, D. *J. Am. Chem. Soc.* 2002, 124, 11856-11857.

Due to the steric hindrance that can be expected between Pd complex 17 and a second stannyl reagent 12, the transfer of a methyl group instead of the acridyl moiety becomes a competitive side reaction that results in the formation of the undesired coupling product 13. Since the transmetallation between 17 and 12 is considered to be slow, C—H insertion of 17 and subsequent reductive elimination affords 14 and 15.

Because of the severe steric hindrance and possible side reactions inherent to their synthesis, highly constrained 1,8-diarylnaphthalenes exhibiting conformational stability have not been reported previously. The preparation of 2 and 3 in 25% yield using our CuO-promoted Stille coupling procedure is quite remarkable since it affords two consecutive coupling steps.

Figure 15:
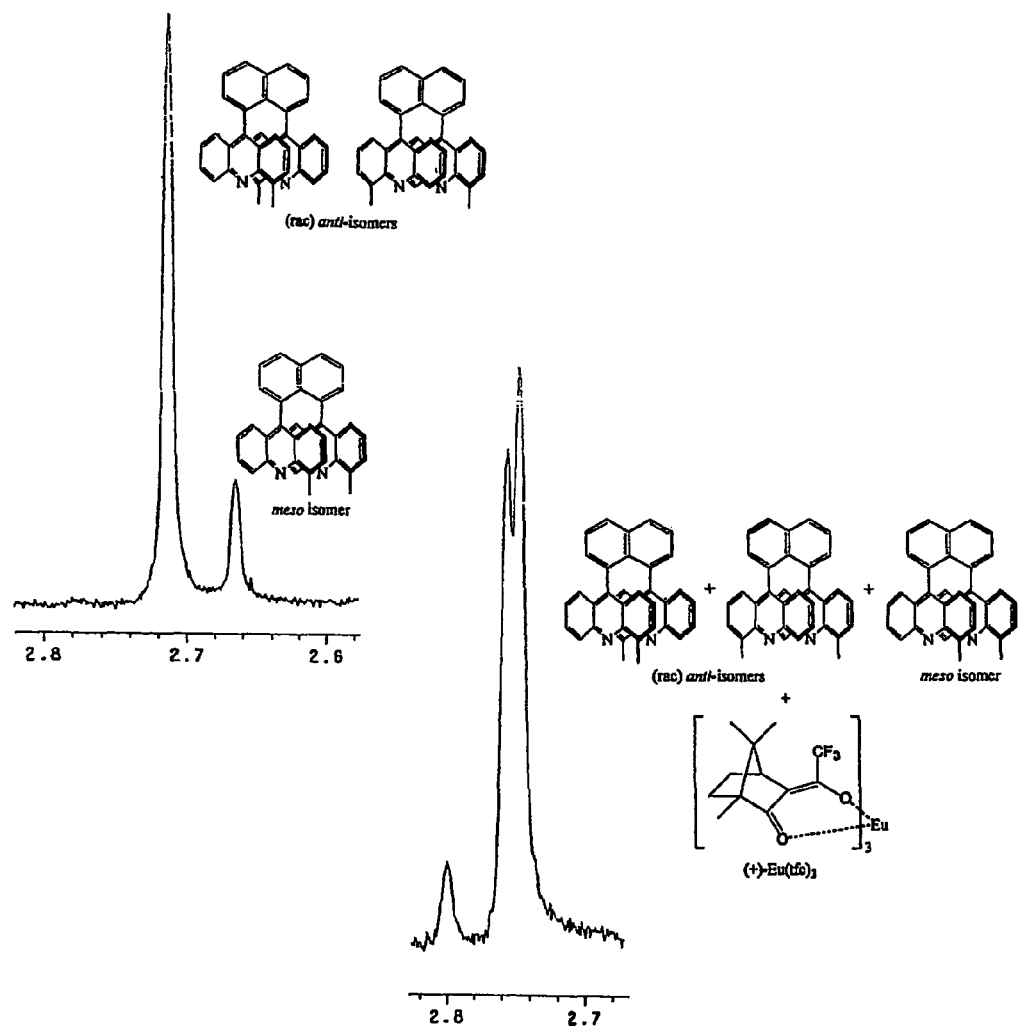
FIG. 15 depicts $^1$H-NMR of the methyl signals of the anti- and syn-isomers of 1,8-bis(9,9'-dimethyl-4,4'-diacridyl)naphthalene, 2, in absence (left) and in presence (right) of 1.2 mol equivalents of (+)-Eu(tfc)$_3$.
Figure 16:
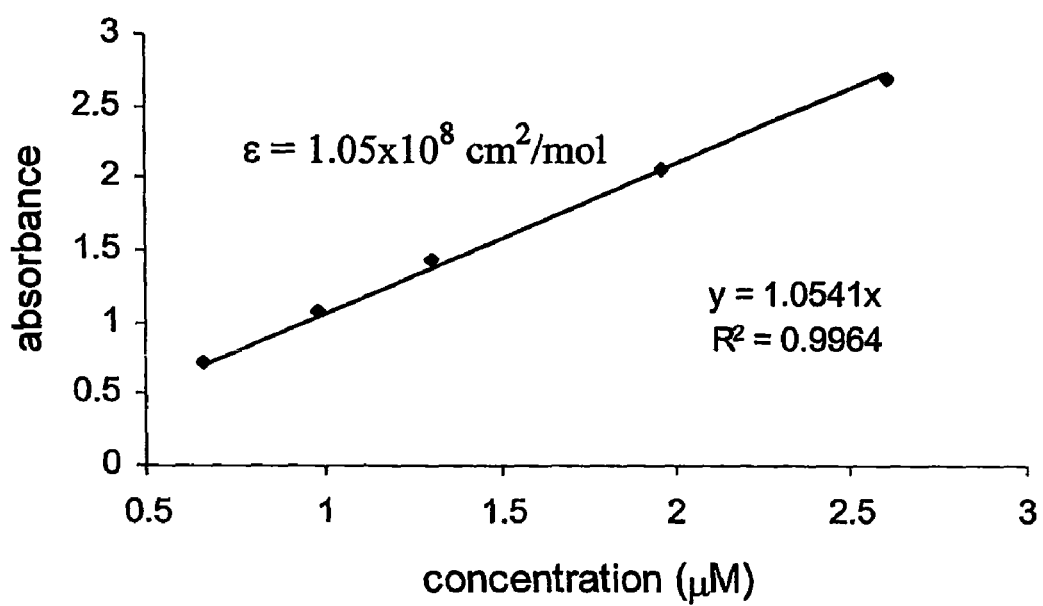
FIG. 16 depicts the determination of the extinction coefficient, ε, of 2 in $CH_2Cl_2$.
Figure 17:
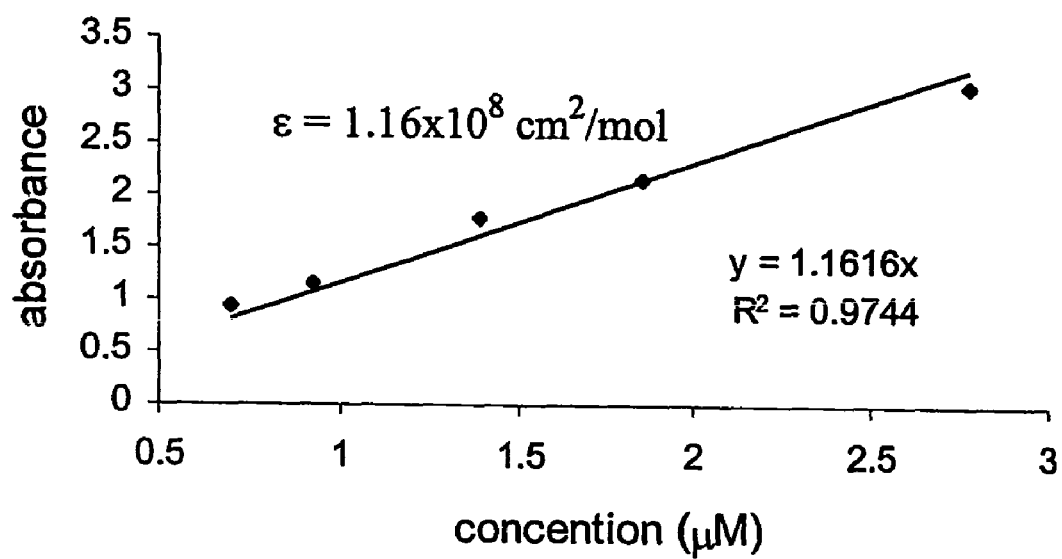
FIG. 17 depicts the determination of the extinction coefficient, ε, of 3 in $CH_2Cl_2$.
Figure 18:
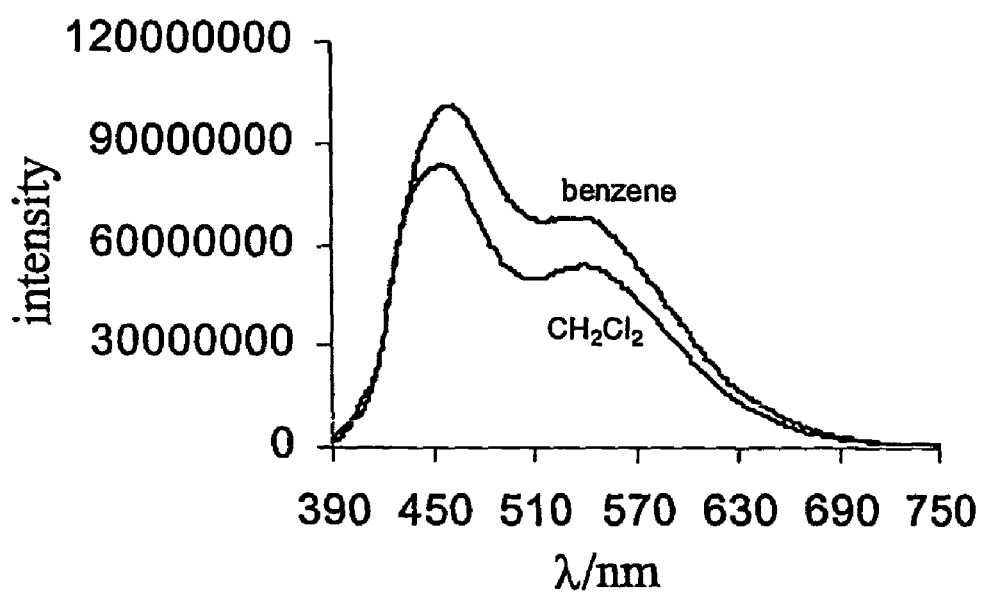
FIG. 18 depicts a fluorescence spectrum of a 4.6:1 anti/syn mixture of 2 in benzene and dichloromethane.
Figure 19:
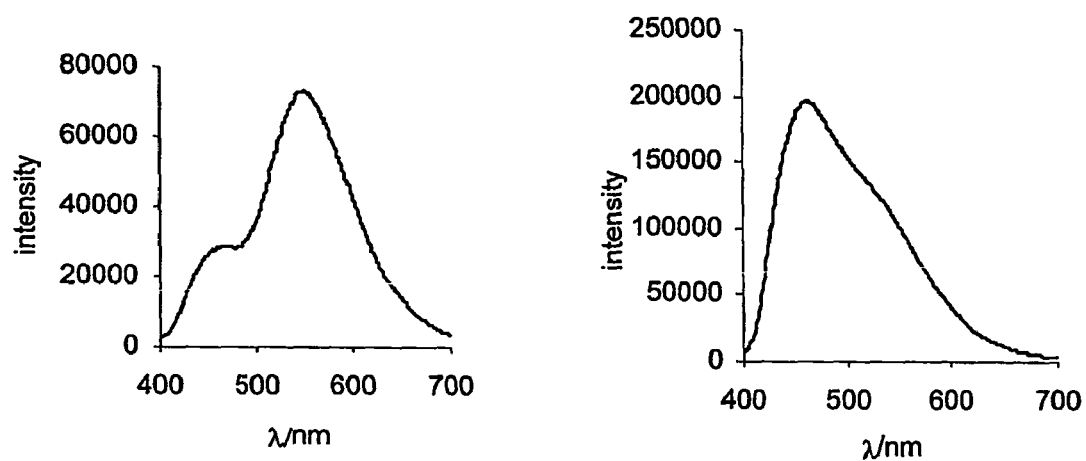
FIG. 19 depicts a fluorescence spectrum of anti-2 (left) and syn-2 (right) in benzene.
Figure 20:
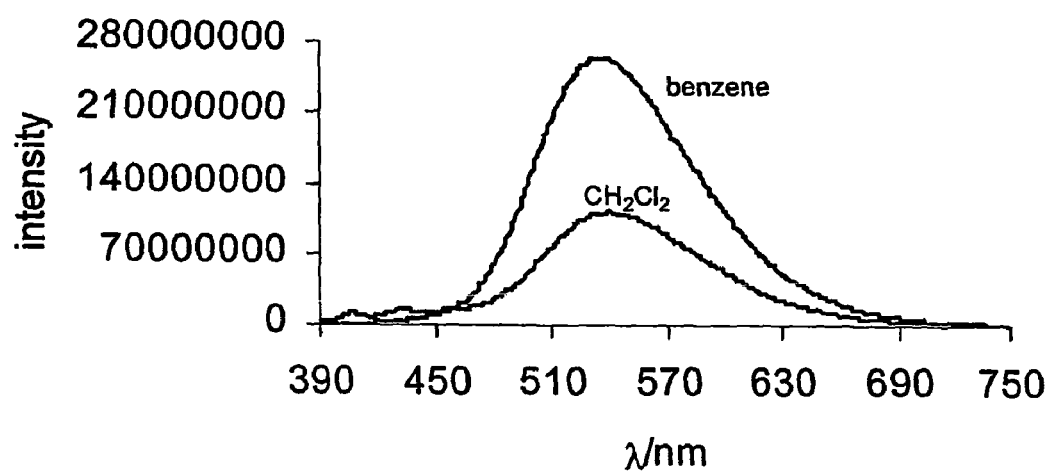
FIG. 20 depicts a fluorescence spectrum of 3 in benzene and dichloromethane.

We were pleased to find that the diastereoisomers of 2 and 3 can be separated by HPLC on a (S)-Phenylglycine column. Semi-preparative separation allowed us to determine the anti/syn ratio of 2 and 3 as 4.6:1 and 1:1, respectively. The isomer ratios of 2 and 3 determined after semi-preparative HPLC separation are in very good agreement with $^1$H-NMR integration results of the product mixtures. The syn and anti-conformation of 2 was determined by $^1$H-NMR using a chiral Lanthamide shift reagent. The formation of diastereomeric complexes of the C$_2$-symmetric anti-isomers of 2 exhibiting anisochronous signals was observed in the presence of (+)-Eu(tfc)$_3$, whereas the signals of the methyl protons of the meso-form are downfield-shifted but are still isochronous, see FIG. 15. Addition of (+)-Eu(tfc)$_3$ to a solution of the syn- and anti-isomers of 2 causes a significant downfield shift for the meso syn-isomer compared to the chiral anti-isomers. The chiral lanthamide shift reagent also differentiates between the two enantiomers of anti-2 which proves that the major fraction obtained by Stille coupling of 1,8-dibromonaphthalene and 12 is anti-2. The conformation of the two isomers of 3 could not be determined using NMR shift reagents or NOESY experiments. In addition, we were not able to separate the enantiomers of anti-2 and anti-3, respectively.

Figure 6:
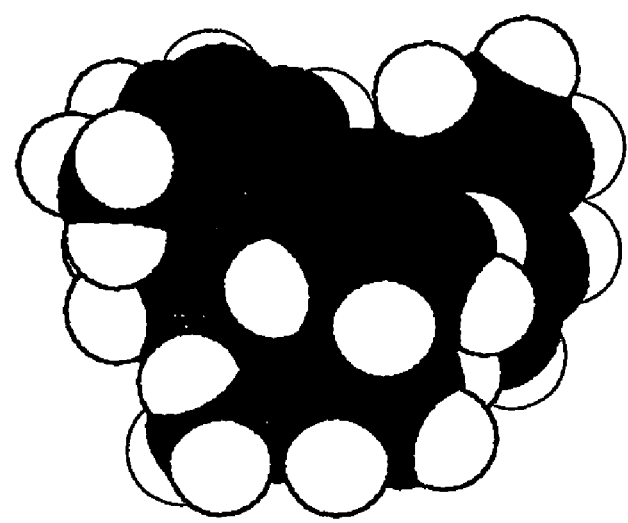
FIG. 6 depicts a space-filling model of anti-2 calculated by PM3.

Isomerization via rotation of one acridyl ring about the chiral acridyl-naphthyl axis is highly restricted due to steric hindrance. According to PM3 calculations, diacridyls 2 and 3 afford compact structures in which both acridyl rings are roughly perpendicular to the mean plane of the naphthyl ring with dihedral angles ranging from 85° to 95°. The acridyl moieties are slightly twisted away from each other and undergo enforced π-stacking, FIG. 6. See (a) Hunter, C. A.; Lawson, K. R.; Perkins, J.; Urch, C. J. *J. Chem. Soc., Perkin*

Trans. 2 2002, 651-669 and Rashkin, M. J.; Waters, M. L. *J. Am. Chem. Soc.* 2002, 124, 1860-1861.

The isolated isomers were heated in acetonitrile in a closed vessel to 180° C. for 24 h. As expected, rotation of either acridyl moiety about the chiral acridyl-naphthalene axis of 2 and 3 is highly sterically hindered and HPLC analysis did not show any sign of isomerization. Utilizing reversible first-order kinetics and the Eyring equation, the Gibbs standard activation energy, $\Delta G^{0\neq}$, for the isomerization of 2 and 3 was calculated to be higher than 180 kJ/mol. Notably, acridyl-naphthalens 2 and 3 began to decompose at 200° C.

Figure 7:
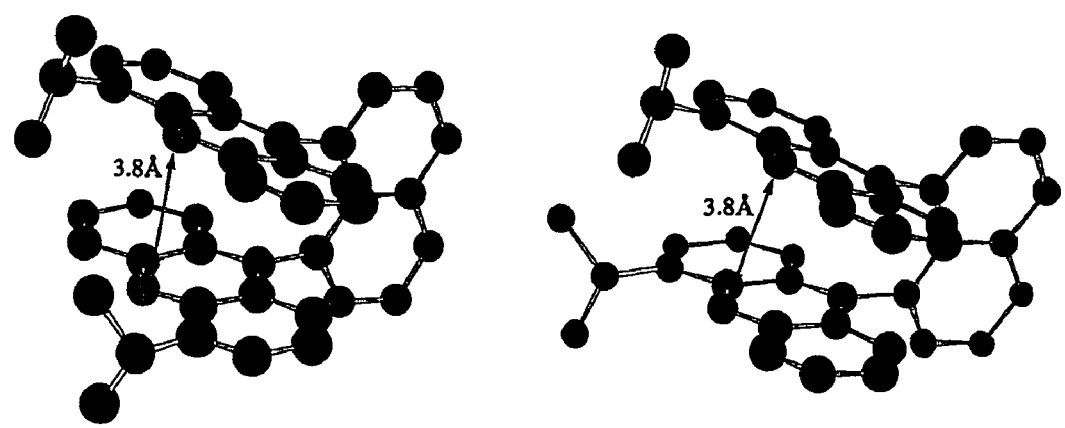
FIG. 7 depicts a PM3 computation of the ground state of anti-(left) and syn-3 (right).

Investigation of the photochemical properties of 2 and 3 revealed UV absorption maxima at 246 nm (log $\epsilon$=8.02 and 8.06, respectively). The UV spectra proved to be reminiscent of isolated, non-conjugated naphthyl and acridyl chromophores as one would expect for a structure exhibiting both hetaryl rings perpendicular to the naphthalene plane. The UV data are thus in agreement with the results of our PM3 calculations. The fluorescence spectra of 2 and 3 were found to be significantly red-shifted compared to that of acridine which exhibits an emission maximum around 400 nm in benzene. This may be attributed to the enhanced $\pi$-stacking of the two acridyl rings. Fluorescence studies of both isomers of diacridine 3 revealed only one maximum at approximately 530 nm and a quantum yield of 18%. In contrast, the fluorescence of the isomers of 2 proved to be significantly different We found that syn-2 is a blue light emitter with a fluorescence maximum at 460 nm, whereas excited anti-2 emits green light at approximately 540 nm. Notably, syn-2 was found to be more fluorescent than its diastereoisomeric anti-isomer. The quantum yields for syn- and anti-2 were determined as 22% and 13%, respectively. The striking difference in the flourescence behavior of the isomers of 2 may be attributed to increased $\pi$-$\pi$ interactions between the anti-parallel acridyl rings of anti-2. The distance between the acridyl nitrogens of syn-2 was determined as 3.6 Å based on PM3 optimization of the ground state. By contrast, PM3 calculations suggest a N—N distance of only 3.4 Å for anti-2. We assume that the close proximity of the acridyl rings facilitates non-radiative relaxation of excited anti-2 resulting in a significantly lower quantum yield than its syn-isomer. Computational studies of the ground state of syn- and anti-3 provided N—N distance of 3.8 Å for both isomers, which explains their indistinguishable fluorescence maximum and quantum yield, FIG. 7.

In summary, we have synthesized conformationally stable 1,8-diarylnaphthalenes via CuO-promoted Stille cross-coupling of 1,8-ibromonaphthalene and 4-alkyl-9-trimethylstannylacridines. The syn- and anti-isomers of 1,8-bis(4,4'-dimethyl-9,9'-diacridyl)naphthalene, 2, and its diisopropyl analog 3 have been isolated for investigation of their stereodynamic properties. No sign of syn/anti-isomerization was observed even at high temperatures indicating a rotational energy barrier above 180 kJ/mol.

Figure 39:
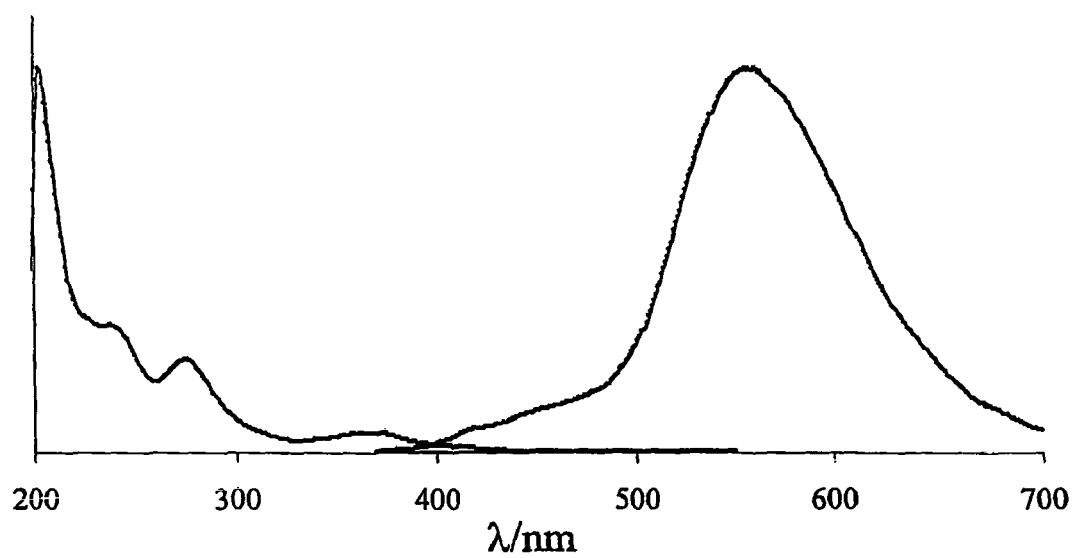
FIG. 39 depicts UV absorption and fluorescence spectrum of 32 (2.6 10-6 M) in acetonitrile. Excitation wavelength was 360 nm. The absorption and emission spectra have been normalized.
Figure 40:
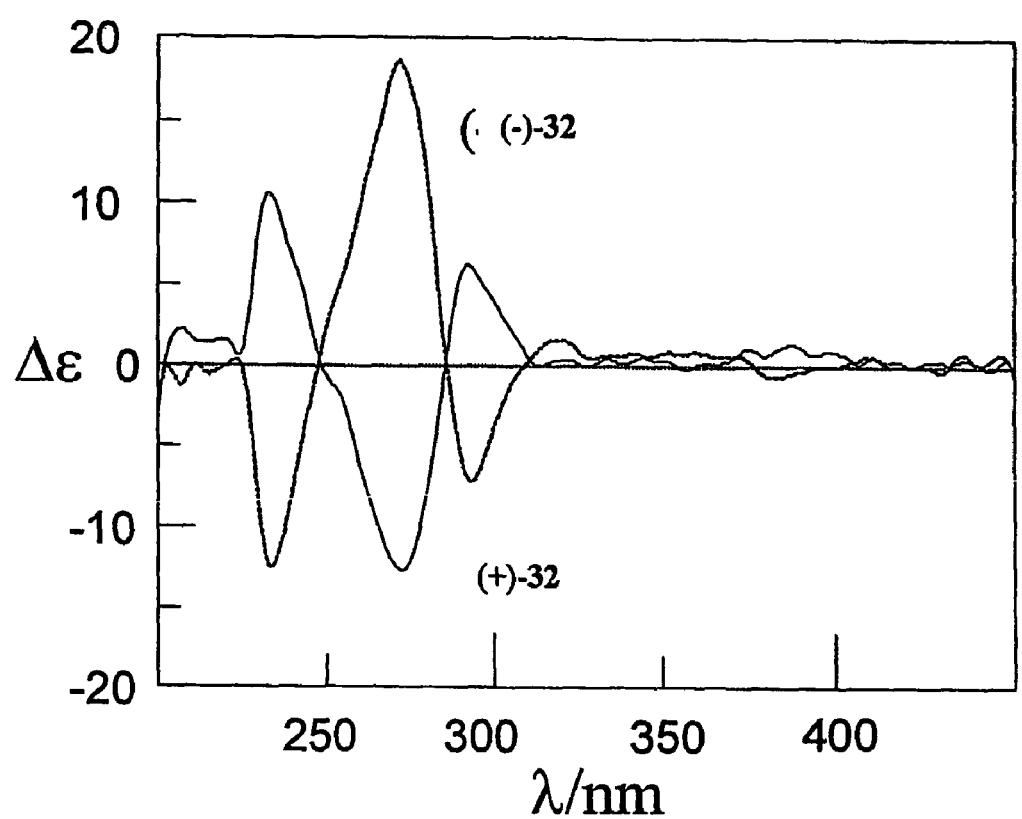
FIG. 40 depicts CD spectrum of the enantiomers of 32 ($c=5\times10^{-5}$ M) in acetonitrile.

FIG. 38 depicts the synthesis of 1,8-bis(3,3'-(3,5-dimethylphenyl)-9,9'-diacridyl)naphthalene (32). Suzuki coupling of commercially available 3-bromoaniline, 25, and 3,5-dimethylboronic acid afforded 3-(3,5-dimethyl-phenyl)aniline, 26, in high yields. Treatment of 26 with 2-chlorobenzoic acid 27 gave N-3-(3,5-dimethylphenyl)anthranilic acid, 28, which was converted to 9-bromo-3-(3,5-dimethylphenyl)acridine, 29, using phosphorous oxybromide. Lithiation of 29 at –78° C. followed by stannylation with trimethylstannyl chloride resulted in the formation of 3-(3,5-dimethylphenyl)-9-trimethylstannylacridine, 30, in high yields. Employing stannane 30 and 1,8-dibromonaphthalene 31 in a CuO-promoted Stille coupling yielded 1,8-bis(3,3'-(3,5-dimethylphenyl)-9,9'-diacridyl)naphthalene, 32. We were pleased to find that the anti-isomers of 32 can be separated on a WhelkO-1 column. The CD spectra of the enantiomers of 32 are shown in FIG. 39.

Figure 42:
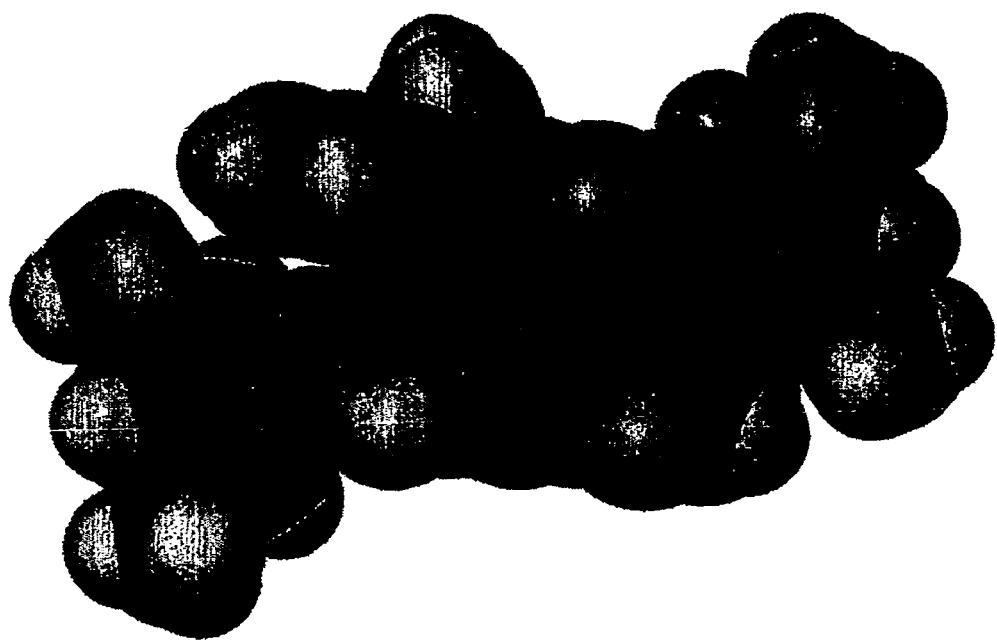
FIG. 42 depicts a single crystal structure of 32.

We were able to grow a monoclinic single crystal of 32 belonging to the C2/c space group through slow evaporation of a dichloromethanelacetonitrile solution (1:1 v/v) to reveal the 3-dimensional structure of the sensor by X-ray analysis, FIG. 42. FIG. 42 shows a view of the anti-parallel acridyl rings (front) attached, to the peri positions of naphthalene (rear). The N—N-distance was determined as 4.38 Å and the splaying angle between the acridyl rings is 11.6°, FIG. 46.

Use of 1,8-Diarylnaphthalenes as Metal Ion Sensors

We chose to investigate the usefulness of this new class of conformationary stable, bidentate 1,8-dihetarylnaphthalenes combining unique stereochemical and photoluminescent features as selective sensors. The majority of fluorosensors developed to date are macrocyclic structures exhibiting a chelating group and a fluorophore physically separated by a spacer. See de Silva, A. P.; Gunaratne, H. Q. N.; Gunnlaugsson, T.; Huxley, A. J. M.; McCoy, C. P.; Rademacher, J. T.; Rice, T. E. *Chem. Rev.* 1997, 97, 1515-1566. However, small sensors afford advantageous cell permeability properties and are therefore particularly promising for biomedical trace analysis.

Figure 8:
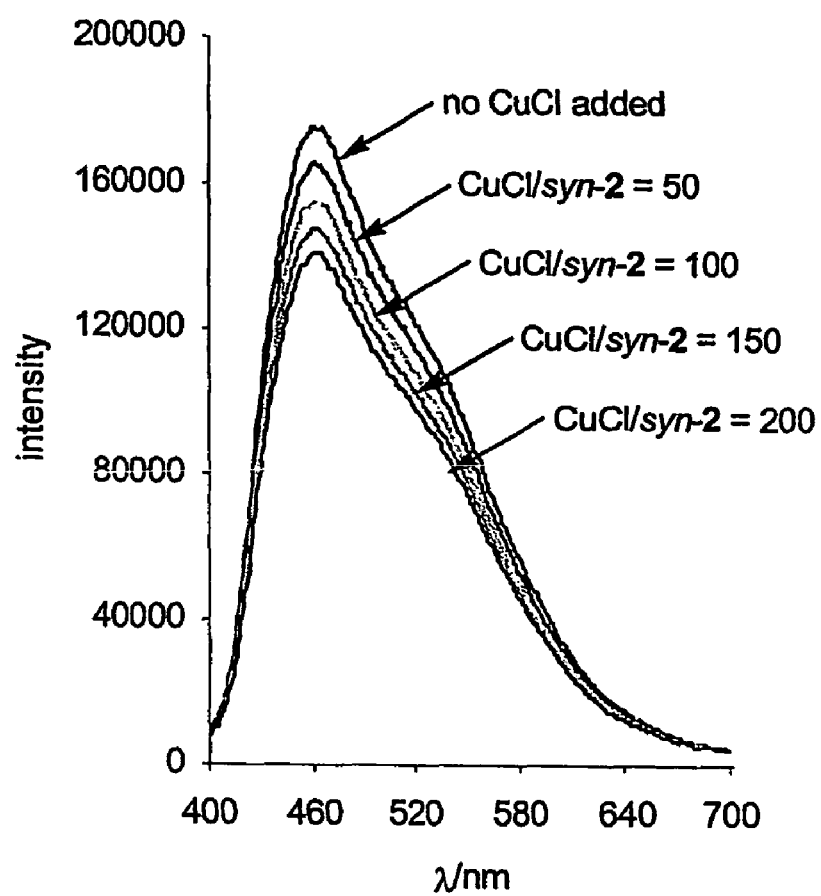
FIG. 8 depicts fluorescence quenching of syn-2 using various concentrations of CuCl. Diacridylnaphthalene syn-2 was dissolved in acetonitrile at a concentration of $10^{-6}$ M.
Figure 9:
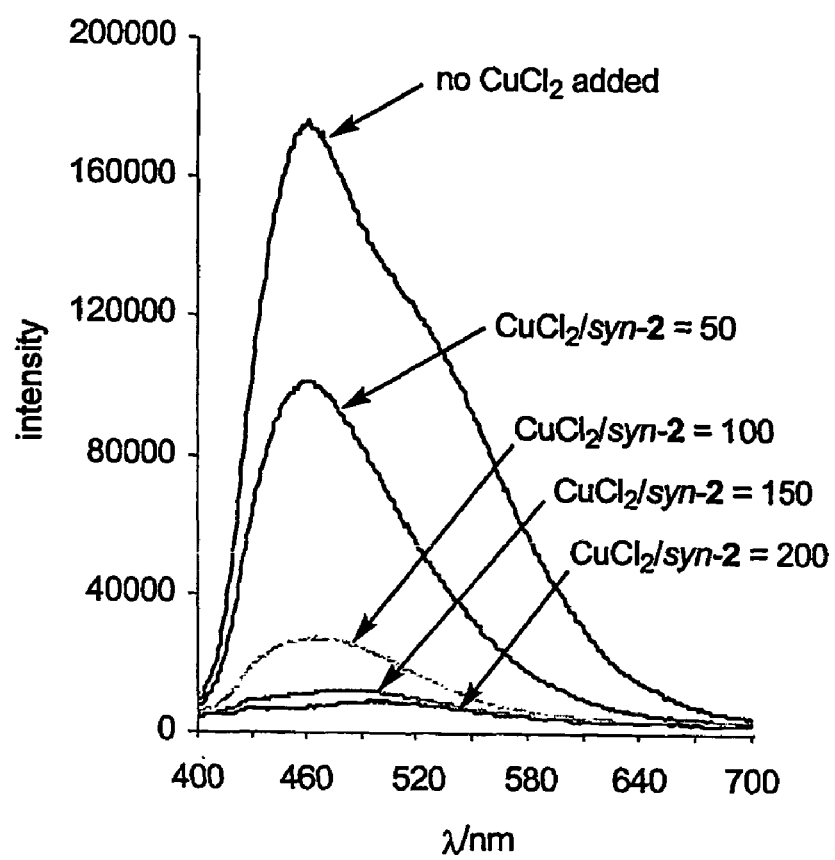
FIG. 9 depicts fluorescence quenching of syn-2 using various concentrations of $CuCl_2$. Diacridylnaphthalene syn-2 was dissolved in acetonitrile at a concentration of $10^{-6}$ M.

Because of its higher quantum yield, we decided to employ the syn-isomer of 2 in metal ion-sensing studies. Fluorescence emission titrations with syn-2 and CuCl and $CuCl_2$ were performed in acetonitrile at room temperature. We did not observe any significant red or blue shifts in the emission spectra of syn-2 in presence of the metal ions. Addition of CuCl did not result in significant quenching even at high excess, FIG. 8. By contrast, titration of the same sensor with $CuCl_2$ revealed highly efficient quenching, FIG. 9.

Because of its considerably different fluorescence response to Cu(I) and Cu(II) ions, the syn-isomer of 2 may be used as a highly selective sensor for real-time qualitative and quantitative analysis of the oxidation state of copper ions in solution. Binding to a metal ion opens new vibrational or electronic pathways for non-radiative relaxation of excited syn-2. Coordination of the diacridylnaphthalene sensor to Cu(II) exhibiting a $d^9$-electronic configuration is likely to result in considerable fluorescence quenching because of photo-induced electron transfer.

Figure 10:
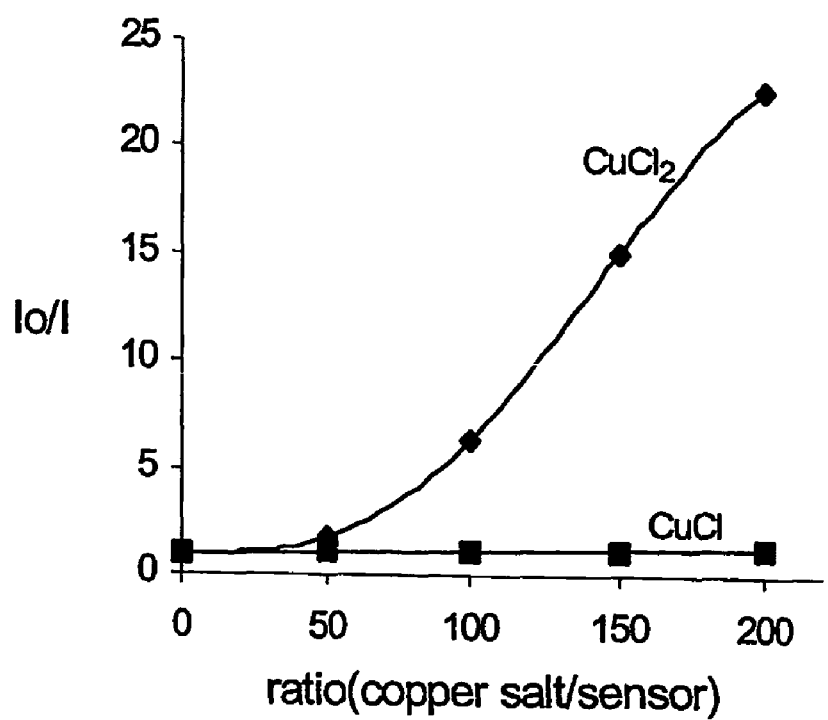
FIG. 10 depicts Stern-Völmer plot of syn-2 in the presence of Cu(I) and Cu(II) chloride. The concentration of syn-2 was $10^{-6}$ M.

Interestingly, we observed non-linear Stern-Völmer quenching of syn-2 by Cu(II) chloride. A fluorescence titration experiment with $CuCl_2$ gave a sigmoidal quenching curve indicating cooperative recognition such as formation of less fluorescent agglomerates at high Cu(II)/sensor ratio, FIG. 10. Chemical sensing based on cooperative recognition has rarely been observed and is believed to result in higher selectivity compared to non-cooperative sensing exhibiting a linear fluorescence response. See Glass, T. E. *J. Am. Chem. Soc.* 2000, 122, 4522-4523.

Figure 11:
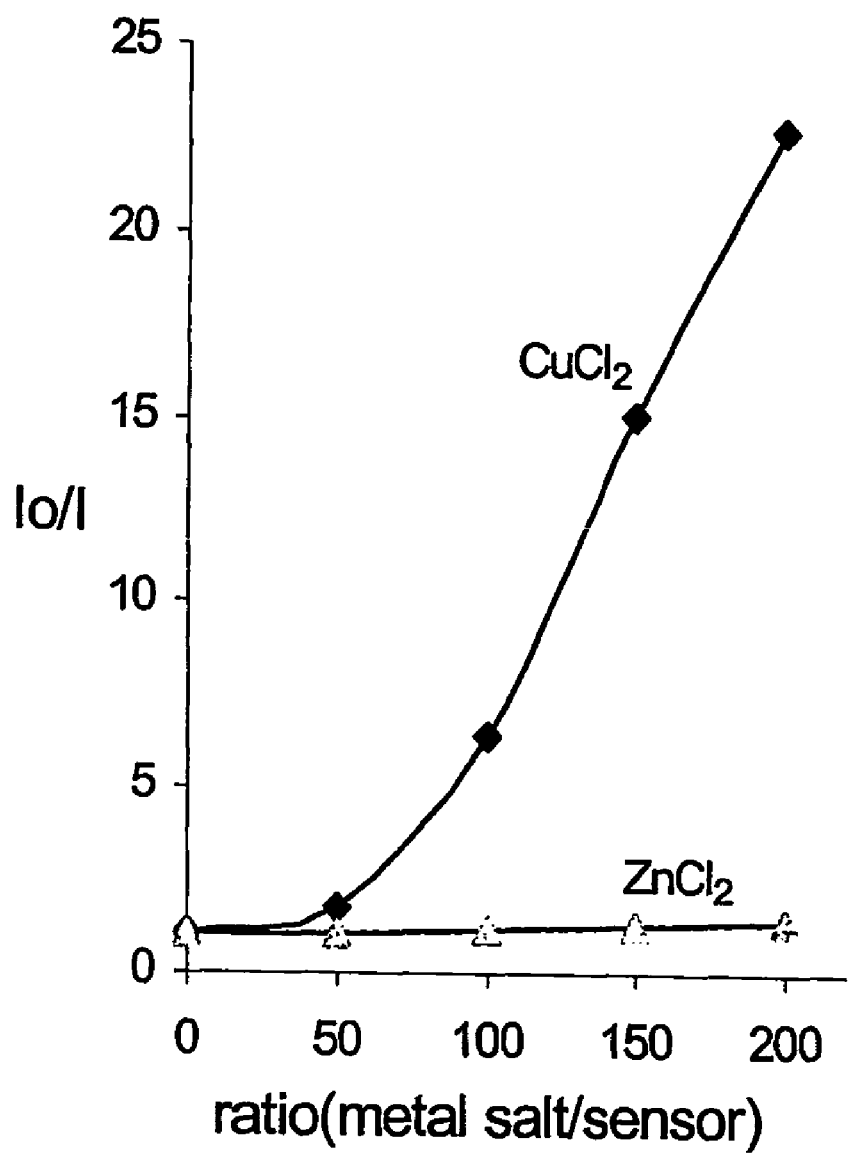
FIG. 11 depicts Stern-Vömer plot of syn-2 in the presence of Cu(II) and Zn(II) chloride. The concentration of syn-2 was $10^{-6}$ M.

By contrast, photo-induced electron transfer is not significant in Cu(I)-syn-2 because of the $d^{10}$-electronic configuration of the metal ion. Further titration experiments revealed that the selector is also capable of differentiating between $CuCl_2$ and $ZnCl_2$. Stern-Völmer plots of the two salts show that Zn(II) barely induces fluorescence quenching of syn-2, FIG. 11. This may also be attributed to negligible photo-induced electron transfer of excited Zn(II)-syn-2.

Figure 12:
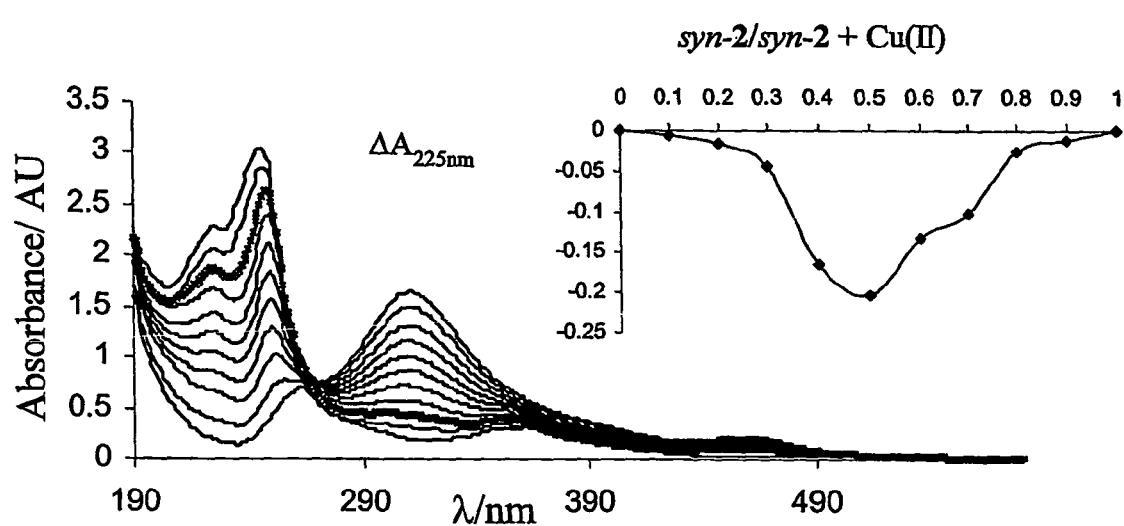
FIG. 12 depicts UV Titration of syn-2 with $CuCl_2$. Inset: Job plot recorded at 225 nm. Sum of concentrations was fixed at $1.5 \times 10^{-5}$ M.
Figure 13:
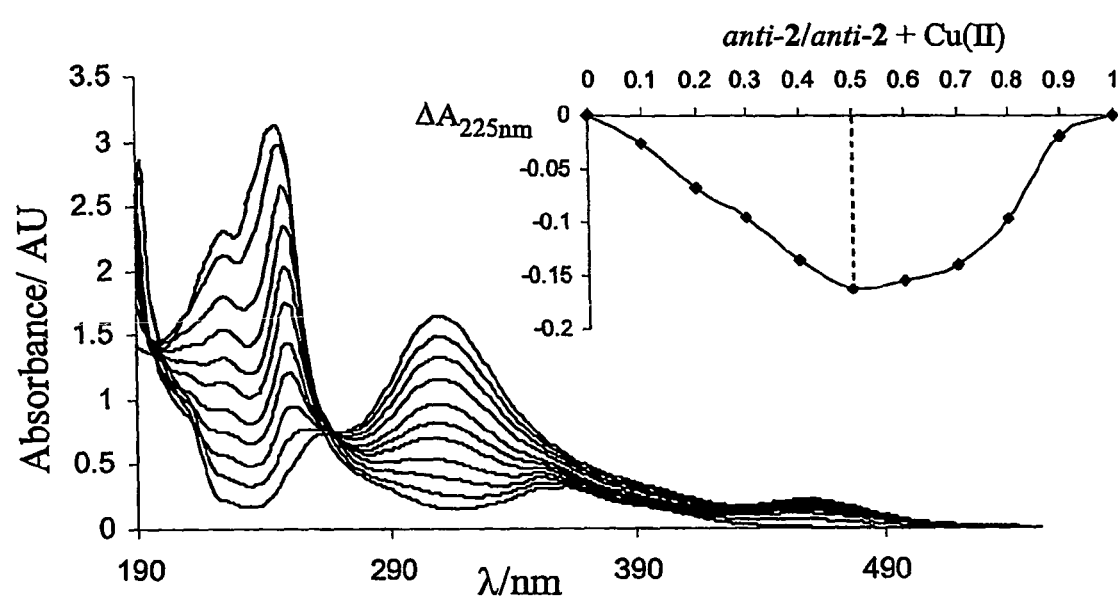
FIG. 13 depicts UV Titration of anti-2 with $CuCl_2$. Inset: Job plot recorded at 225 nm. Sum of concentrations was fixed at $1.5 \times 10^{-5}$ M.

We conducted UV titration experiments of syn- and anti-2 using Cu(II) chloride for the determination of the stoichiometry of the metal-sensor complexes formed in acetonitrile, FIGS. 12 and 13. In accordance with our fluorescence experiments, we did not observe any significant red or blue shifts in the absorption spectra of the diacridylnaphthalenes in presence of Cu(II). Job analysis of Cu(II) chloride and syn-2 or anti-2 at a total concentration of $1.5 \times 10^{-5}$ M revealed the existence of one maximum at a molar ratio of 0.5 which is in agreement with the formation of an equimolar complex, FIGS. 12 and 13. See Connors, K. A. *Binding Constants, The Measurement of Molecular Complex Stability*; Wiley: New York, 1987. Notably, a job plot affords the sensor/metal ratio but does not differentiate between 1:1, 2:2 complexation or formation of even higher aggregrates, which would explain the cooperative recognition of Cu(II) observed with syn-2.

Figure 14:
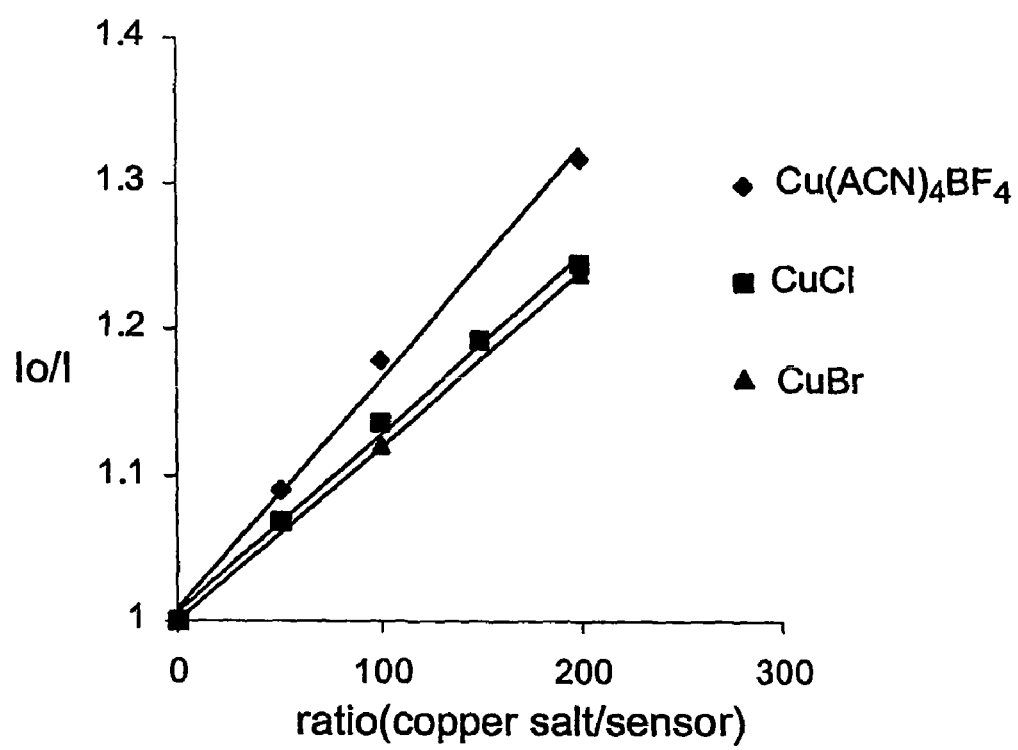
FIG. 14 depicts counterion effect on the fluorescence quenching of syn-2 in acetonitrile. The concentration of syn-2 was $5 \times 10^{-6}$ M.

The selectivity between copper and zinc ions is quite important for bioanalytical and environmental studies. Cu(II) and Zn(II) are essential trace elements that occur in metalloproteins with various biological functions in bacteria, plants and mammals. Cu(II) is also a significant environmental pollutant. An important requirement for an useful cation-selective sensor is the absence of a significant fluorescence response to anions also present in solution. We therefore selected three different Cu(I) salts for fluorescence titration experiments to determine any counteranion effects on the photochemical properties of the sensor. Indeed, syn-2 did not show any significant fluorescence quenching due to the presence of chloride, bromide or tetrafluoroborate, FIG. 14. The Stern-Völmer plots obtained with CuCl and CuBr are almost superimposable, whereas quenching by Cu(ACN)$_4$BF$_4$ was found to be approximately 7% more effective.

In summary, fluorescence titration experiments with the syn-isomer of 2 revealed highly efficient quenching by Cu(II) ions, which was attributed to cooperative recognition. Job analysis based on UV titration experiments revealed formation of a complex exhibiting equimolar amounts of the sensor and Cu(II). Almost no quenching effects were observed with Cu(I) and Zn(II) salts, which is probably a consequence of negligible photo-induced electron transfer pathways for non-radiative relaxation. The fluorescence quenching was found to be cation-selective and almost independent of counteranions present in solution. The high sensitivity inherent to fluorescence spectroscopy combined with the remarkable ion-selectivity of this new class of chemosensors opens new venues for probing small traces of metal ions.

We believe that the development of a synthetic route toward C$_2$-symmetric and conformationally stable 1,8-diarylnaphthalenes such as anti-2 and anti-3 will allow the exploration of a new class of compounds for enantioselective sensing of chiral molecules. The synthesis and enantioseparation of new axially chiral 1,8-dihetarylnaphthalenes that are capable of participating in diastereomeric interactions that can be quantitatively measured by fluorescence quenching are contemplated embodiments of the present invention.

Use of 1,8-Diarylnaphthalenes as Chiral Carboxylic Acid Sensors

The bidentate ligand 32 exhibits two anti-parallel acridyl moieties that form a C$_2$-symmetric cleft for stereoselective recognition of chiral carboxylic acids measurable by fluorescence spectroscopy The structure of this C2-symmetric sensor is designed to (a) embed interactions with chiral acids into a highly stereoselective environment, and to (b) utilize fluorescence spectroscopy to monitor stereoselective recognition.

Fluorescence studies of 32 in acetonitrile revealed an emission maximum at 550 nm. Despite its congested structure, diacridylnaphthalene 32 has a fluorescence quantum yield of 0.17 and a fluorescence lifetime of 5.46 ns. Fluorescence experiments were conducted using a Fluoromax-2 from Instruments S.A. Inc. All emission spectra were collected under nitrogen using a $2.6 \times 10^{-6}$ M solution of (+)-32 in carefully degassed acetonitrile under inert atmosphere. Excitation wavelength was 360 nm and emission wavelength was 550 nm. The quantum yield of 1 was determined as 0.17 following literature procedures (Jones II, G.; Jackson, W. R.; Choi, C.-Y. *J. Phys. Chem.* 1985, 89, 294-300). Diacridylnaphthalene 1 was excited at 360 nm and relative integrated intensities of the emission spectra were compared to anthracene in benzene. The fluorescence lifetime of anti-1 in acetonitrile was determined as 1.56 ns. Frequency domain data were obtained with a 10 GHz frequency domain fluorometer (Laczko, G.; Gryczynski, I.; Gryczynski, Z.; Wiczk, W.; Malak, H.; Lakowicz, J. R. *Rev. Sci. Instrum.* 1990, 61, 2331-2337). The modulated excitation was provided by the harmonic content of a LASER pulse train with a repetition rate of 3.81326 MHz and a pulse width of 7 ps from a synchronously pumped and cavity dumped pyridine 1 dye LASER. The dye LASER was pumped with a mode-locked Ar ion LASER (coherent). The dye LASER output was frequency doubled to 350 nm for excitation of 1. The emitted fluorescence was observed through a glass long wave pass filter ($\lambda_{obs} > 520$ nm). The fluorescence intensity decay data were fitted to the multi-exponential model $I(t) = \Sigma \alpha_i \exp(-t/\tau_i)$ where $\tau_i$ are the individual decay times and $\alpha_i$ are the associated preexponential factors. The parameters were recovered by non-linear least squares using the theory and software described elsewhere (Lakowicz, J. R.; Laczko, G.; Cherek, H.; Gratton, E.; Linkeman, H. *Biophys. J.* 1984, 46, 463-477).

Figure 41:
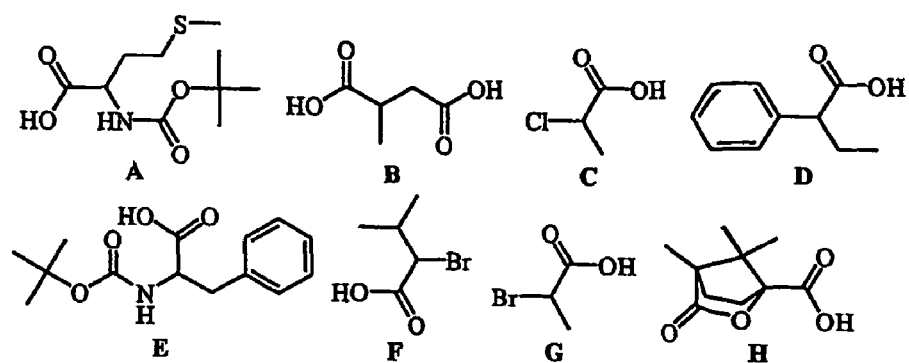
FIG. 41 depicts carboxylic acids A to H.

As mentioned above, we were pleased to find that the anti-isomers of 32 can be separated into enantiomers by HPLC on a WhelkO-1 column and decided to employ chiral analytes A to H in fluorescence titration experiments, FIG. 41.

Titration studies using (+)-32 at $2.6 \times 10^{-6}$ M in acetonitrile (excitation at 360 nm, emission maximum at 550 nm) showed that the sensor can differentiate between the enantiomers of all carboxylic acids employed in this study. Fluorescence quenching was observed with enantioselectivities, $\alpha$, up to 4.5 in the case of camphanic acid, H. Since, diacridylnaphthalene (+)-32 exhibits two potential binding sites, the fluorescence quenching was analyzed using the Stern-Volmer equations derived for 1:1 (1) and 1:2 (2) complexes to determine the enantioselectivity and binding mode of the corresponding diastereomeric complexes:

$$\frac{I_0}{I - I_0} = \frac{b}{a - b} \left\{ \frac{1}{K[M]} + 1 \right\} \quad (1)$$

$$\frac{I_0}{I - I_0} = \frac{b}{a - b} \left\{ \frac{1}{K[M]^2} + 1 \right\} \quad (2)$$

where $I_0$ is the inherent fluorescence intensity of (+)-32, I is the fluorescence intensity in the presence of the quencher, Q, and $K_{SV}$ is the Stern-Volmer constant.

Figure 43:
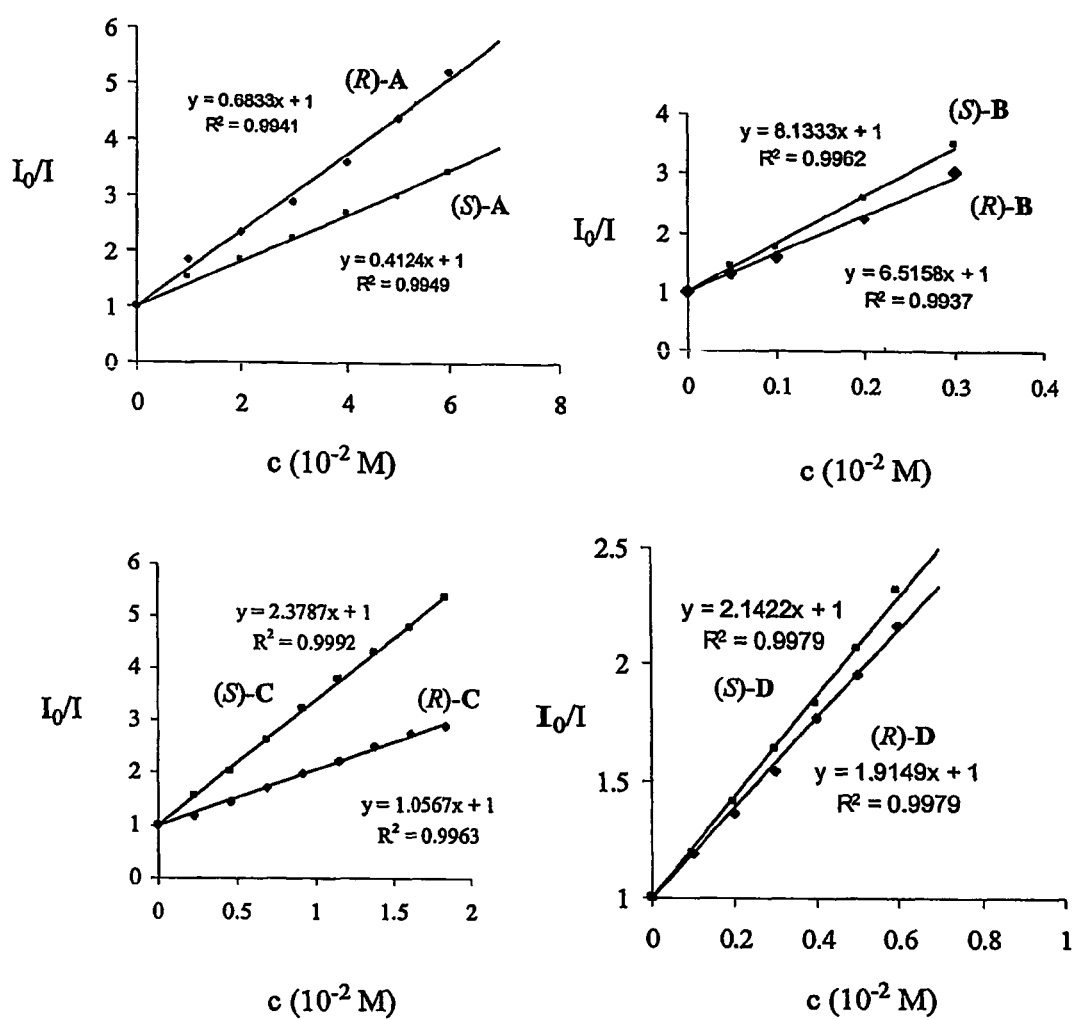
FIG. 43 depicts Linear Stern-Volmer plots for the enantioselective fluorescence quenching of (+)-32 in the presence of carboxylic acids A to D. The concentration of (+)-32 in acetonitrile was $2.6\times10^{-6}$ M. Excitation (emission) wavelength: 360 nm (550 nm).
Figure 44:
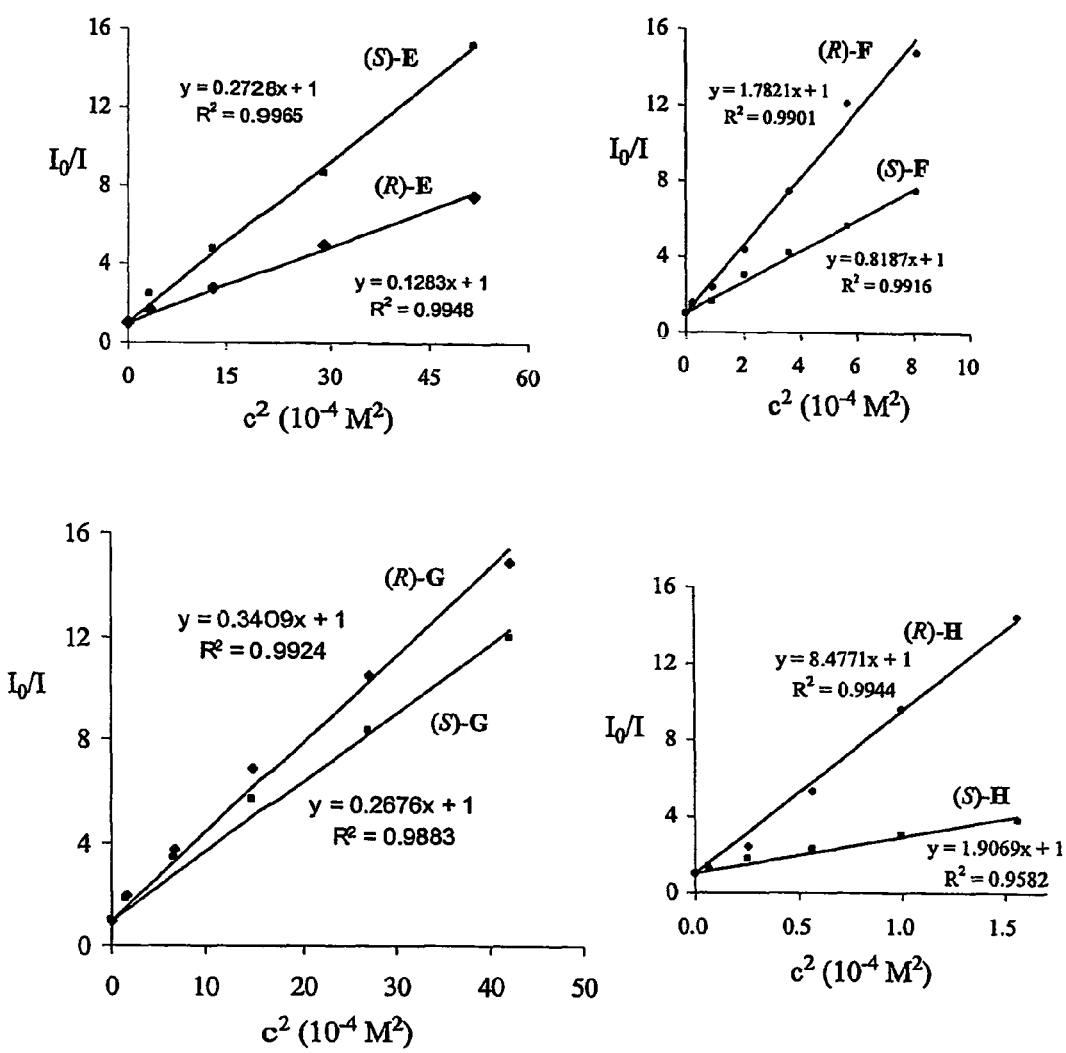
FIG. 44 depicts Linear Stern-Volmer plots for the enantioselective fluorescence quenching of (+)-32 in the presence of carboxylic acids E to H. The concentration of (+)-32 in acetonitrile was $2.6\times10^{-6}$ M. Excitation (emission) wavelength: 360 nm (550 nm).
Figure 47:
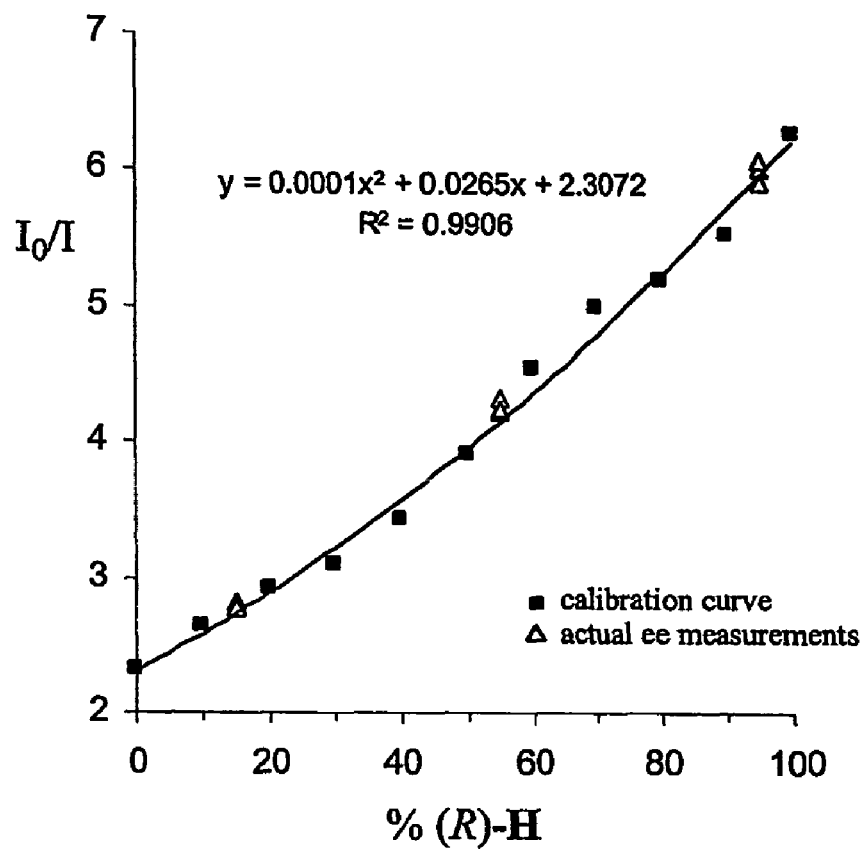
FIG. 47 depicts Figure calibration and actual enantiopurity measurement of nine samples containing 15, 55, and 95% of (R)-H. The concentration of the sensor 32 was $4.4\times10^{-6}$ M and the total concentration of H (R+S) was $1.25\times10^{-2}$ M in acetonitrile. Excitation (emission) wavelength: 360 nm (550 nm).

We found that acids A-H form an equimolar complex with (+)-32, whereas two equivalents of A-H coordinate simultaneously to the diacridylnaphthalene sensor. For example, (+)-32 was found to differentiate between (R)- and (S)-N-t-Boc-methionine, A, with an enantioselectivity factor, $\alpha$, $K^R_{sv}/K^S_{sv}$ of 1.7 based on a linear Stern-Volmer plot for the corresponding diastereomeric 1:1 complexes, FIG. 43. By contrast, (+)-32 forms a 1:2 complex with N-t-Boc-phenylalanine, E, with an enantioselectivity factor $K^S_{sv}/K^R_{sv}$ of 2.1. The fluorosensor also differentiates between the enantiomers of methylsuccinic acid, B, 2-chloropropionic acid, C, 2-phenylbutyric acid, D, 2-bromo-3-methylbutyric acid, F, and 2-bromopropionic acid G, FIGS. 43-45. In order to evaluate the accuracy and reproducibility of our sensing method we prepared nine samples containing 15, 55, and 95% of (R)-H and determined the enantiomeric composition based on the fluorescence quenching of 32. Averaging the fluorescence measurements of the individually prepared samples we calculated 16, 58, and 96% enantiopurity using a calibration curve. The results are within +/−3% of the actual enantiopurity of the samples and thus demonstrate the high reproducibility and accuracy of this method, FIG. 47-48.

1,1'-Binaphthyl-derived fluorosensors have been designed for chiral recognition of mandelic acid its derivatives (Lin, J.; Hu, Q.-S.; Xu, M.-H.; Pu, L. *J. Am. Chem. Soc.* 2002, 124, 2088-2089. (f) Pu, L. *Chem. Rev.* 2004, 104, 1687-1716; Xu, M.-H.; Lin, J.; Hu, Q.-S.; Pu, L. *J. Am. Chem. Soc.* 2002, 124, 14239-14246; Lin, J.; Zhang, H.-C.; Pu, L. *Org. Lett.* 2002, 4, 3297-3300; and Lin, J.; Li, Z.-B.; Zhang, H.-C.; Pu, L. *Tetrahedron Lett.* 2004, 45, 103-106). However, to the best of our knowledge, diacridylnaphthalene 32 is the first enantioselective fluorosensor applicable to a broad variety of carboxylic acids including amino acids, aliphatic acids, arylalkanoic acids, and halogenated carboxylic acids. The observed change of the fluorescence intensity of excited (+)-32 in the presence of carboxylic acids A-H is probably a result of static quenching through non-radiative relaxation of diastereomeric acid-base adducts (Lakowicz, J. R. Principles of fluorescence spectroscopy; 2nd ed.; Kluwer Academic, New York, 1999, 238-257). The equilibrium binding constants of the diastereomeric complexes were obtained using the Benesi-Hildebrand equation for 1:1 complexes (A-D) and 1:2 complexes (E-H), FIG. 45 (Wong, W.-L.; Huang, K.-H.; Teng, P.-F.; Lee, C.-S.; Kwong, H.-L. *Chem. Commun.* 2004, 384-385; Benesi, H. A.; Hildebrand, J. H. *J. Am. Chem. Soc.* 1949, 71, 2703-2707; Connors, K. A. Binding constants. The measurements of molecular complex stability; Wiley & Sons, New York, 1987, 149-160.) The binding constants vary significantly and indicate that coordination between the sensor and the carboxylic acids may either be attributed to O—H . . . N hydrogen bonds or to charge-assisted carboxylate-acridinium $O^-$ . . . $H—N^+$-hydrogen bonding involving proton transfer in some cases (Lee, I. S.; Shin, D. M.; Chung, Y. K. *Cryst. Growth Des.* 2003, 3, 521-529; Bhogala, B. R.; Nangia, A. *Cryst. Growth Des.* 2003, 3, 547-554.)

Achiral fluorosensors have been used for HTS of combinatorial libraries but only few examples of enantioselective analysis with chiral fluoroprobes have been reported to date (Klein, G.; Reymond, J. L. *Helv. Chim. Acta* 1999, 82, 400-407; Copeland, G. T.; Miller, S. J. *J. Am. Chem. Soc.* 1999, 121, 4306-4307; Stauffer, S. R.; Beare, N. A.; Stambuli, J. P.; Hartwig, J. F. *J. Am. Chem. Soc.* 2001, 123, 4641-4642; Korbel, G. A.; Lalic, G., Shair, M. D. *J. Am. Chem. Soc.* 2001, 123, 361-362; Matsushita, M.; Yoshida, K; Yamamoto, N.; Wirsching, P.; Lerner, R. A.; Janda, K. *Angew. Chem. Int. Ed.* 2003, 42, 5984-5987). Since our results show that 1,8-diacridylnaphthalene 32 is a fluorosensor with a broad application spectrum, it may be employed in HTS efforts based on indicator-displacement assays to evaluate the asymmetric synthesis of chiral carboxylic acids including non-steroidal anti-inflammatory drugs such as naproxen or ibuprofen (Zhu, L.; Anslyn, E. V. *J. Am. Chem. Soc.* 2004, 126, 3676-3677).

In summary, we have developed a $C_2$-symmetric sensor that undergoes stereoselective interactions with a variety of chiral carboxylic acids resulting in fluorescence quenching. In one embodiment these carboxylic acids are selected from the group consisting of amino acids, aliphatic acids, aromatic acids, heteroaliphatic acids, heteroaromatic acids, arylalkanoic acids, heteroarylalkonic acids and halogenated carboxylic acids. The high sensitivity inherent to fluorescence spectroscopy combined with the considerable stereoselectivity and broad application spectrum of this chemosensor provides the potential for real-time analysis of the enantiomeric composition of chiral carboxylic acids.

Design of 1,8-Diarylnaphthalene N-Oxide Sensors

Figure 21:
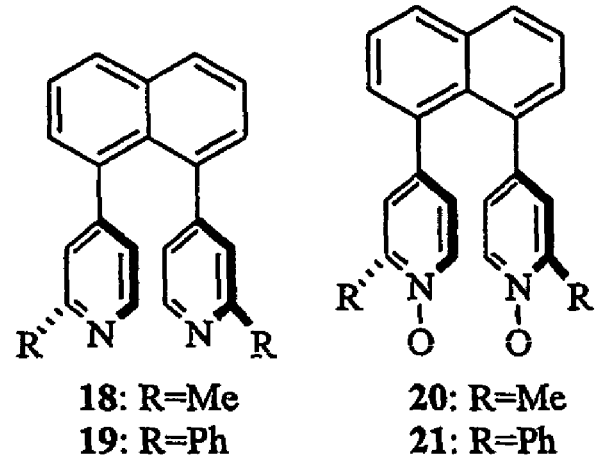
FIG. 21 depicts the structures of atropisomers 18-21.
Figure 22:
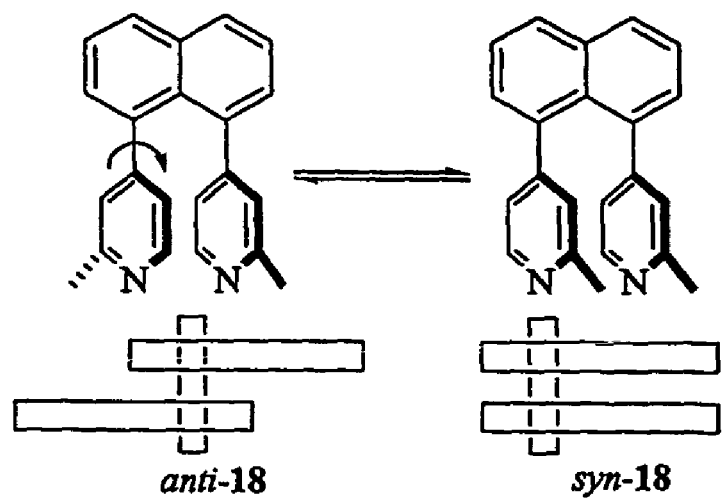
FIG. 22 depicts the isomerization of 18.

In continuation of our studies of the stereodynamics of axially chiral 1,8-dipyridylnaphthalenes 1-4, we have envisioned the development of a new class of compounds derived from the 1,8-dihetarylnaphthalene framework for stereoselective sensing, FIG. 21. See Wolf, C.; Ghebremariam, B. T. *Synthesis* 2002, 749-752; Wolf, C.; Ghebremariam, B. T. *Tetrahedron: Asymm.* 2002, 13, 1153-1156; and Wolf, C.; Tumambac, G. E. *J. Phys. Chem. A* 2003, 107, 815-817. 1,8-Disubstituted naphthalenes display striking properties because of their unique geometry and related atropisomerism. A variety of peri substituted naphthalene derivatives exhibiting alkyl, aryl, and hetaryl groups has been synthesized to study steric and electronic interactions between π-stacked aryl rings. See Fields, D. L.; Regan, T. H. *J. Org. Chem.* 1971, 36, 2995-3001; Steele, M.; Watkinson, M.; Whiting, A. *J. Chem. Soc., Perkin Trans.* 2001, 588-598. (k) Thirsk, C.; Hawkes, G. E.; Kroemer, R. T.; Liedl, K. R.; Loertig, T.; Nasser, R.; Pritchard, R. G.; Steele, M.; Warren, J. E.; Whiting, A. *J. Chem. Soc., Perkin Trans.* 2 2002, 1510-1519; Zoltewicz, J. A.; Maier, N. M.; Lavieri, S.; Ghiviriga, I.; Abboud, K. A. *Tetrahedron* 1997, 53, 5379-5388; and references therein. Both peri aryl rings have been reported to be cofacial and almost perpendicular to the naphthalene moiety in the ground state. The naphthalene moiety is twisted and the two aryl groups are splayed out to minimize steric interactions and through-space Coulomb repulsion between the peri substituents. Rotation about the pyridyl-naphthalene bond of 1,8-bis(2,2'-dimethyl-4,4'-dipyridyl)naphthalene, 1, causes interconversion of the chiral anti-isomers to the meso syn-isomer via a T-shaped transition state exhibiting the edge of the rotating aromatic ring directed towards the face of the neighboring ring, FIG. 22.

We determined the range of the Gibbs activation energy, $\Delta G^{\neq}$, for the syn/anti-diastereoisomerization of 1-4 as 64 to 73 kJ/mol using variable-temperature NMR spectroscopy (DNMR) and dynamic HPLC and computer simulation (DH-PLC). See Gafni, A. *J. Am. Chem. Soc.* 1980, 102, 7367-7368 and Yorozu, T.; Hayashi, K; Irie, M. *J. Am. Chem. Soc.* 1981, 103, 5480-5484. We concluded that incorporation of two selectively substituted acridyl groups into the peri positions of naphthalene should result in conformationally stable, bidentate 1,8-bis(9,9'-diacridyl)naphthalenes that would be highly useful enantioselective sensors. See De Silva, A. P.; Gunaratne, H. Q. N.; Gunnlaugsson, T.; Huxley, A. J. M.; McCoy, C. P.; Rademacher, J. T., Rice, T. E. *Chem. Rev.* 1997, 97, 1515-1586.

Figure 23:
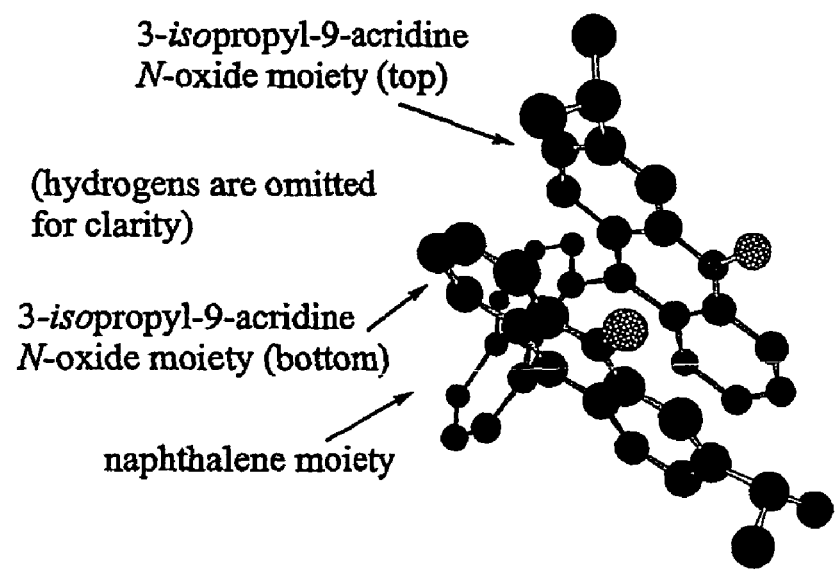
FIG. 23 depicts a PM3-calculated ground state of (R,R)-22.
Figure 24:
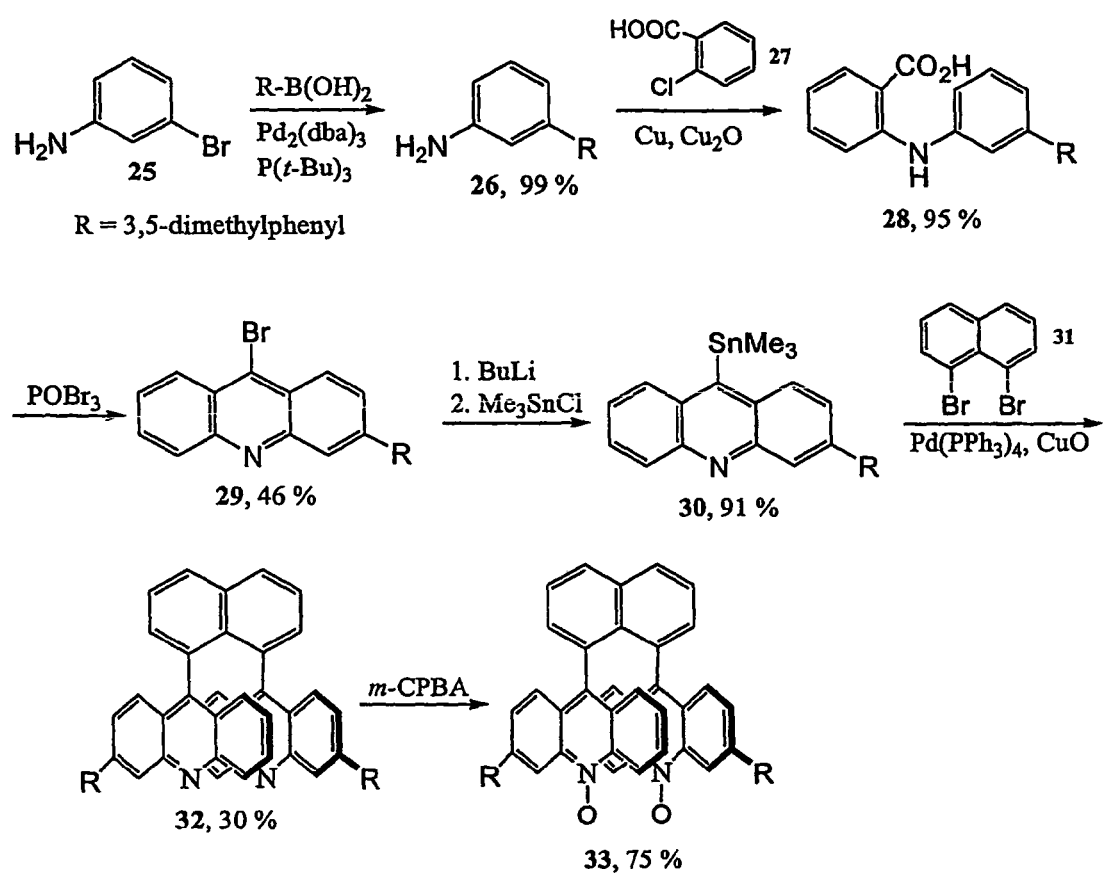
FIG. 24 depicts the synthesis of 1,8-diacridylnaphthalene N,N'-dioxide 33.

Optimization of the ground state of (R,R)-1,8-bis(3,3'-diisopropyl-9,9'-diacridyl)naphthalene N,N'-dioxide, (R,R)-5, by PM3 calculations show that both acridine rings are cofacial and almost perpendicular to the naphthalene moiety, FIG. 23. The distance between both oxygen atoms of 5 was calculated as 4.1 Å, which would provide an attractive coordination environment for organic molecules such as bidentate amines, alcohols, and carboxylic acids. Notably, chiral N-oxides have been employed as Lewis base or Lewis acid catalysts in various asymmetric reactions, including Michael additions, cyanosilylations, aldol additions, and ring openings of meso epoxides. See Malkov, A. V.; Bell, M.; Vassieu, M.; Bugatti, V.; Kocovsky, P. *J. Mol. Catal.* 2003, 196, 179-186; Saito, M.; Nakajima, M.; Hashimoto, S. *Tetrahedron* 2000, 56, 9589-9594; Chen, F. Feng, X.; Qin, B.; Zhang, G.; Jiang, Y. *Org. Lett.* 2003, 5, 949-952; Denmark, S. E.; Fan, Y. *J. Am. Chem.*

Soc. 2002, 124, 4233-4235; Tao, B.; and Lo, M. M.-C.; Fu, G. C. *J. Am. Chem. Soc.* 2001, 123, 353-354.

Because of the well-known usefulness of N,N'-dioxides in asymmetric catalysis and their ability to form strong complexes with hydrogen bond donors and a variety of metal ions, we concluded that axially chiral N,N'-dioxides such as 5 provide an attractive opportunity for developing new molecular sensors. See Karayannis, N. M.; Pytlewski, L. L.; Mikulski, C. M. *Coord. Chem. Rev.* 1973, 11, 93-159 and Ryzhakov, A. V.; Nizhnik, Y. P.; Andreev, V. P. *Russ. J. Org. Chem.* 2000, 36, 884-886. The structure of this new class of $C_2$-symmetric N,N'-dioxides is designed to (a) embed interactions with chiral molecules into a highly stereoselective environment, and to (b) utilize fluorescence spectroscopy to monitor stereoselective recognition.

Various high-throughput screening (HTS) methods utilizing chromatography for the evaluation of chiral catalysts have been developed by us and others. See Wolf, C.; Hawes, P. A. *J. Org. Chem.* 2002, 67, 2727-2729; Wolf, C.; Francis, C. J.; Hawes, P. A.; Shah, M. *Tetrahedron: Asymm.* 2002, 13, 1733-1741; and Duursma, A.; Minnaard, A. J.; Feringa, B. L. *Tetrahedron* 2002, 58, 5773-5778. Employing diethylzinc in the enantioselective alkylation of aldehydes to chiral alcohols we have shown that multi-substrate screening can provide yields, enantioselectivity, substrate specificity, and sense of chiral induction of a catalyst. However, multi-substrate one-pot screening often suffers from interference between simultaneously run reactions and chromatographic separation of several products obtained from one reaction mixture is often difficult and time-consuming.

We anticipate that N,N'-dioxide 33 and derivatives thereof will be highly useful for HTS of the enantiomeric composition and absolute configuration of many chiral compounds and thus provide a new tool for real-time analysis of asymmetric reactions. The introduction of enantioselective fluorescent sensors to HTS is expected to afford superior sensitivity, time-efficiency, and applicability over other rapid methods based on electrophoresis, NMR, HPLC/CD, MS or enzymatic techniques. See (a) Reetz, M. T.; Kuhling, K. M.; Deege, A.; Hinrichs, H.; Belder, D. *Angew. Chem. Int. Ed.* 2000, 39, 3891-3893; (b) Evans, M. A.; Morken, J. P. *J. Am. Chem. Soc.* 2002, 124, 9020-9021; (c) Ding, K.; Ishii, A.; Mikami, K. *Angew. Chem. Int. Ed.* 1999, 38, 497-501; (d) Taji, H.; Watanabe, M.; Harada, N.; Naoki, H.; Ueda, Y. *Org. Lett.* 2002, 4, 2699-2702; (e) Reetz, M. T. *Angew. Chem. Int. Ed.* 2002, 41, 1335-1338.

A few achiral fluorosensors have been used for HTS of combinatorial libraries but only one example of enantioselective analysis utilizing chiral probes has been reported to date. See (a) Copeland, G. T.; Miller, S. J. *J. Am. Chem. Soc.* 1999, 121, 4306-4307; (b) Stauffer, S. R.; Beare, N. A.; Stambuli, J. P.; Hartwig, J. F. *J. Am. Chem. Soc.* 2001, 123, 4641-4642; (c) Korbel, G. A.; Lalic, G., Shair, M. D. *J. Am. Chem. Soc.* 2001, 123, 361-362. Since our results show that N,N'-dioxides such as 16 can be used for enantioselective recognition of chiral hydrogen bond donors, this new class of fluorosensors will allow real-time screening of various asymmetric reactions, e.g. the synthesis of chiral alcohols from aldehydes mentioned above or the synthesis of amino acids and amino alcohols.

Synthesis of 1,8-Diarylnaphthalene N-Oxides

We were able to prepare 1,8-bis(4,4'-dimethyl-9,9'-acridyl)naphthalene, 23, and 1,8-bis(4,4'-dimethyl-9,9'-diacridyl)naphthalene, 24, utilizing CuO-promoted Stille cross-couplings of 1,8-dibromonaphthalene and 4-alkyl-9-trimethylstannylacridines as described above. The isolated meso syn- and $C_2$-symmetric anti-isomers of 23 and 24 did not show any sign of isomerization after heating to 180° C. for 24 h indicating a Gibbs activation energy for interconversion, $\Delta G^{\neq}$, of at least 180 kJ/mol based on the Eyring equation. However, using a variety of chiral HPLC columns we were not able to separate the enantiomers of anti-23 or anti-24. In addition, formation of the corresponding N-oxides was found to proceed with very low yields, which is probably a consequence of steric shielding of the acridyl nitrogens by the adjacent alkyl groups.

Optimization of the conformation of anti-24 by PM3 calculations confirmed the shielding effect of the ipso-isopropyl groups. We concluded that better accessibility of the acridyl nitrogens is required in order to facilitate formation of N-oxides and HPLC enantioseparation. We therefore decided to incorporate 3,5-dimethylphenyl moieties into position 3 of the acridyl rings, FIG. 25.

Suzuki coupling of commercially available 3-bromoaniline, 25, and 3,5-dimethylboronic acid afforded 3-(3,5-dimethylphenyl)aniline, 26, in high yields. Treatment of 26 with 2-chlorobenzoic acid, 27, gave N-3-(3,5-dimethylphenyl)anthranilic acid, 28, which was converted to 9-bromo-3-(3,5-dimethylphenyl)acridine, 29, using phosphorous oxybromide. As expected, we observed that 9-bromo-1-(3,5-dimethylphenyl)acridine was formed as a major by-product during ring construction. Lithiation of 29 at −78° C. followed by stannylation with trimethylstannyl chloride resulted in the formation of 3-(3,5-dimethylphenyl)-9-trimethylstannylacridine, 30, in high yields. Employing stannane 30 and 1,8-dibromonaphthalene, 31, in a CuO-promoted Stille coupling previously developed in our laboratories yielded 1,8-bis(3,3'-(3,5-dimethylphenyl)-9,9'-diacridyl)naphthalene, 32. Oxidation of 32 using m-chloroperoxybenzoic acid gave 1,8-bis(3,3'-(3,5-dimethylphenyl)-9,9'-diacridyl)naphthalene N,N'-dioxide, 33.

Figure 25:
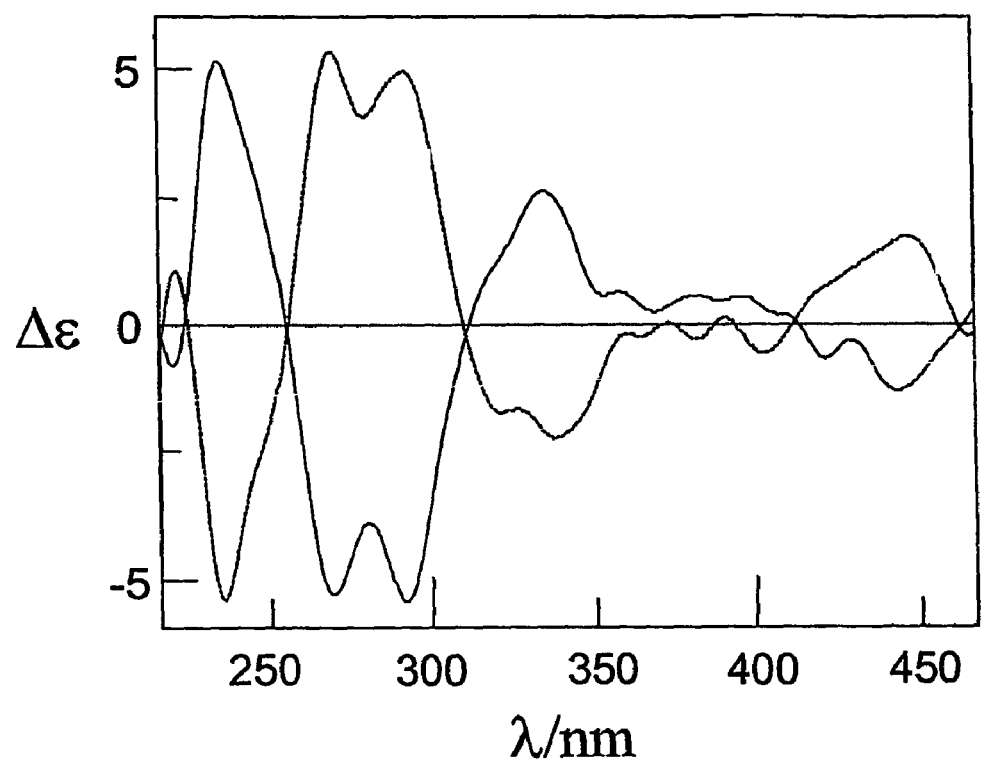
FIG. 25 depicts a CD spectrum of the enantiomers of 33.

We were pleased to find that the anti-isomers of 33 can be separated on a Chiralpak AD column. The CD spectra of the enantiomers of 33 are shown in FIG. 25.

To elucidate the three-dimensional structure of N,N'-dioxide 33 and to provide an understanding of its coordination sphere and potential as an enantioselective sensor, we obtained single crystals for X-ray analysis. From a dichloromethane solution, we obtained a co-crystal with one molecule of dichloromethane through slow diffusion of diethyl ether at room temperature. In addition, slow solvent evaporation of a solution of 33 in acetonitrile resulted in formation of another single crystal suitable for X-ray diffraction, FIGS. 27 and 28. The crystallographic coordinates of the single crystals of 33 have been deposited with the Cambridge Crystallographic Data Centre; deposition numbers CCDC 218158 and CCDC 218159.

Accordingly, 33 can afford at least two different conformations in the solid state. The 'open structure' exhibits a wider cleft between the two 3,5-dimethylphenyl moieties, whereas the 'closed structure' affords a smaller cleft. The closest distance between the ortho hydrogens of the two 3,5-dimethylphenyl rings, i.e. H(21) and (H21') was determined as 5.28 Å and 12.09 Å, respectively. Notably, the distance between the two N-oxide groups remains the same in both structures, i.e. 4.32 Å or 4.30 Å. In the open structure, the acridyl rings are slightly splayed away from each other about 3.2° and the torsion angle between the acridyl rings was found to be 24.8°. The closed structure exhibits the acridyl moieties splayed about 4.8° and a torsion angle of −20.9°, FIG. 28. Interestingly, the closed structure co-crystallized with one molecule of dichloromethane (not shown) whereas the open structure co-crystallized with one molecule of acetonitrile (not shown) and a water molecule, which undergoes hydrogen bonding to both N-oxide groups. The two single crystal structures of N,N'-dioxide 33 demonstrate its ability to participate in hydrogen bonding and a considerable structural flexibility, which is expected to facilitate binding to molecules of varying geometry and size.

In sum, we have discovered and synthesized a class of axially chiral N,N'-dioxides exhibiting anti-parallel 3-substituted acridyl N-oxide moieties attached to the peri positions of naphthalene. The highly constrained $C_2$-symmetric framework was synthesized via CuO-mediated palladium-catalyzed Stille cross-coupling of dibromonaphthalene and 3-(3, 5-dimethylphenyl)-9-trimethylstannylacridine. Oxidation gave fluorescent 1,8-bis(3,3'-(3,5-dimethylphenyl)-9,9'-diacridyl)naphthalene N,N'-dioxide, which was found to differentiate between the enantiomers of N-t-Boc-valine and anti-diaminocyclohexane. Single crystal structure analysis and fluorescence titration experiments showed that this new fluorosensor affords a flexible structure that is likely to facilitate stereoselective hydrogen bonding to a variety of chiral compounds.

Enantioselective Sensor Studies

Exhibiting two anti-parallel, selectively substituted acridyl moieties, N,N'-dioxide 33 is designed to undergo stereoselective recognition of chiral compounds measurable by fluorescence spectroscopy. Fluorescence studies of N,N'-dioxide 33 in acetonitrile revealed an emission maximum at 567 nm. Molecular modeling and X-ray analysis suggested that 33 would undergo strong interactions with hydrogen bond donors such as diamines or amino acids which would result in either a shift of the fluorescence emission maximum or a change in fluorescence intensity.

Figure 29:
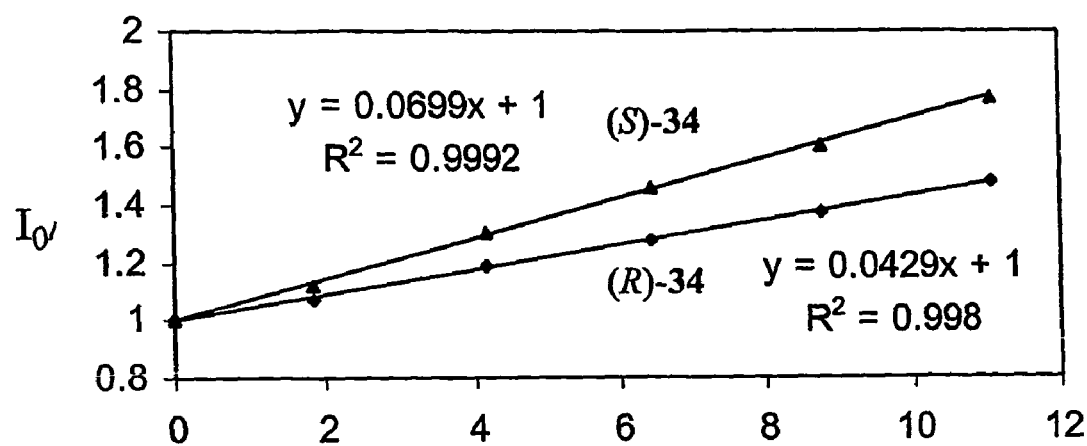
FIG. 29 depicts a stern-Völmer plot of enantiopure 33 in the presence of (R)- and (S)-N-t-Boc-valine, 17.
Figure 30:
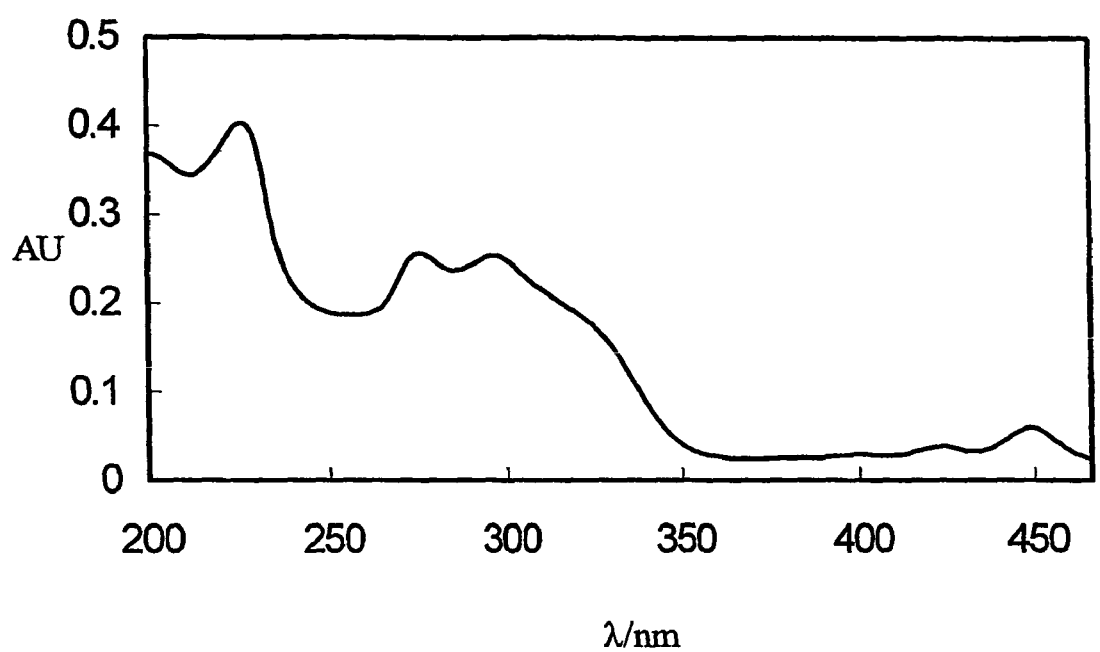
FIG. 30 depicts a UV spectrum of anti-33 in acetonitrile.
Figure 31:
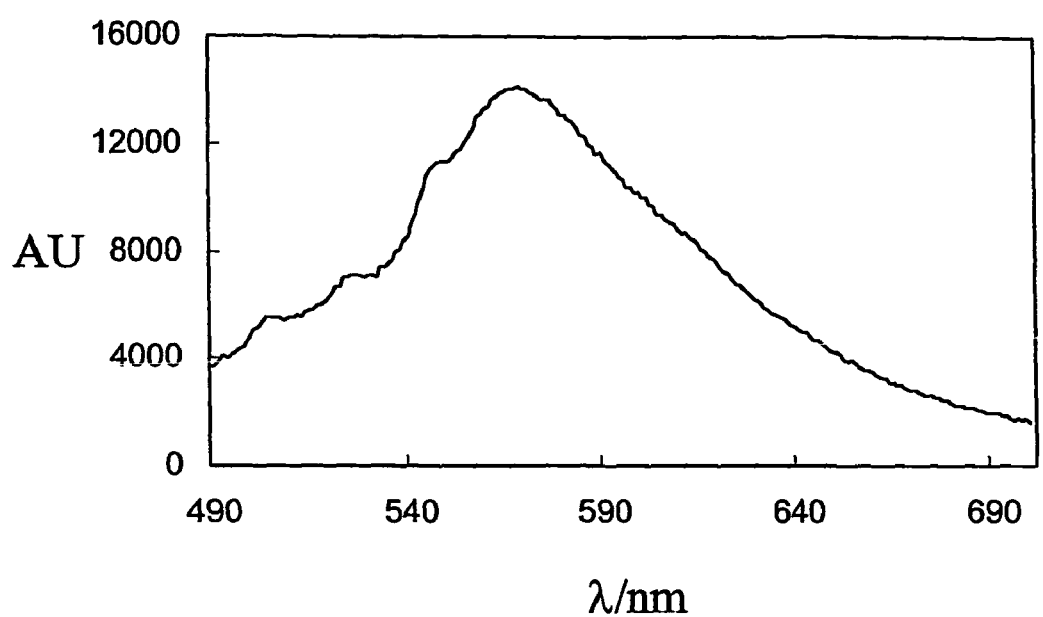
FIG. 31 depicts a fluorescence spectrum of anti-33 in acetonitrile.
Figure 32:
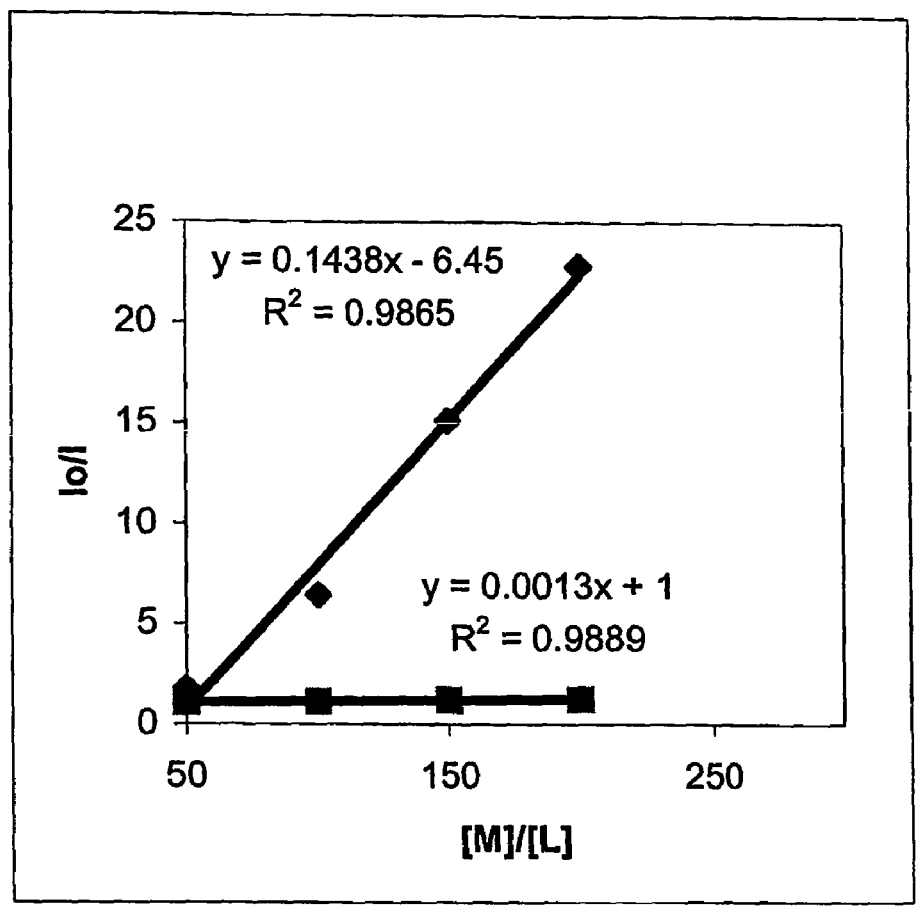
FIG. 32 depicts a Stern-Volmer plot for syn-18 in presence of $Cu^{2+}$ and $Cu^+$ (Linear Stern-Volmer plots Selectivity factor $(Ksv(Cu^{2+})/Ksv(Cu^+)=111)$.
Figure 33:
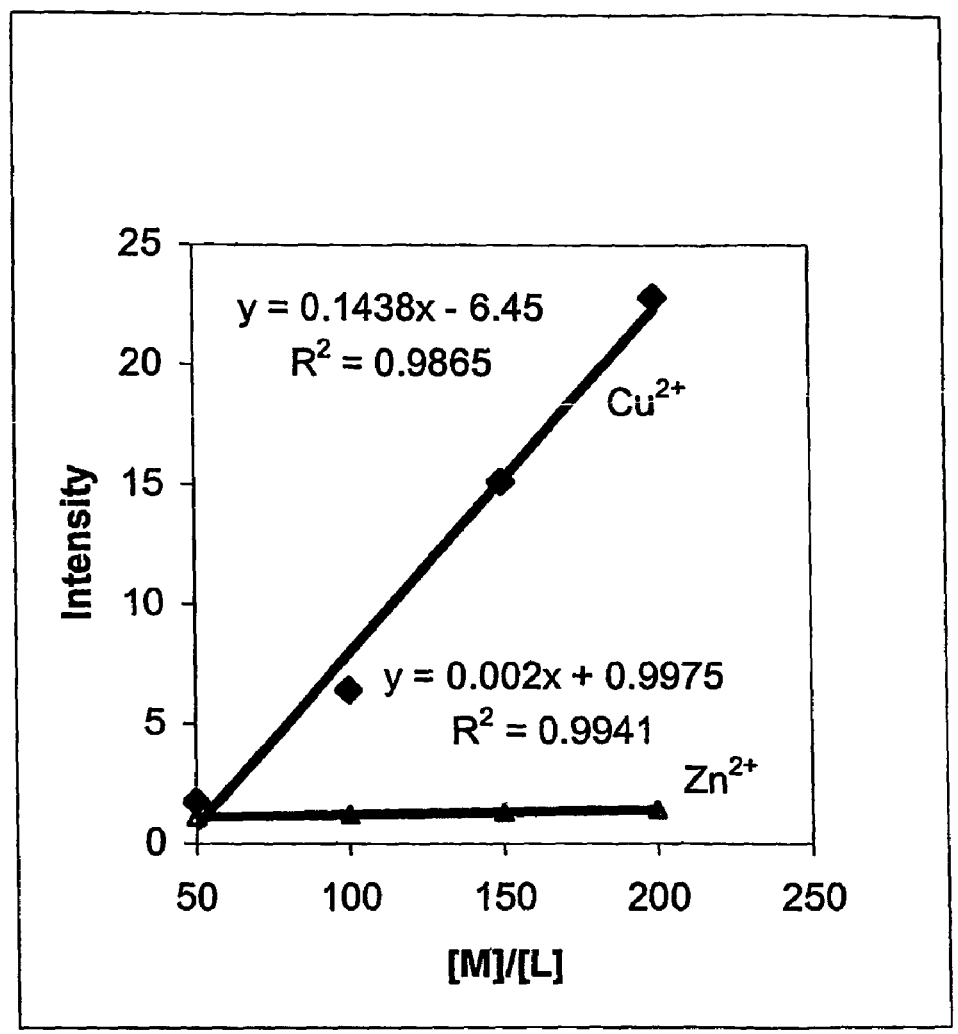
FIG. 33 depicts a Stern-Volmer plot for syn-18 in presence of $Cu^{2+}$ and $Zn^{2+}$ (Linear Stern-Volmer plots Selectivity factor $(Ksv(Cu^{2+})/K_{SV}(Zn^{2+})=72)$.
Figure 34:
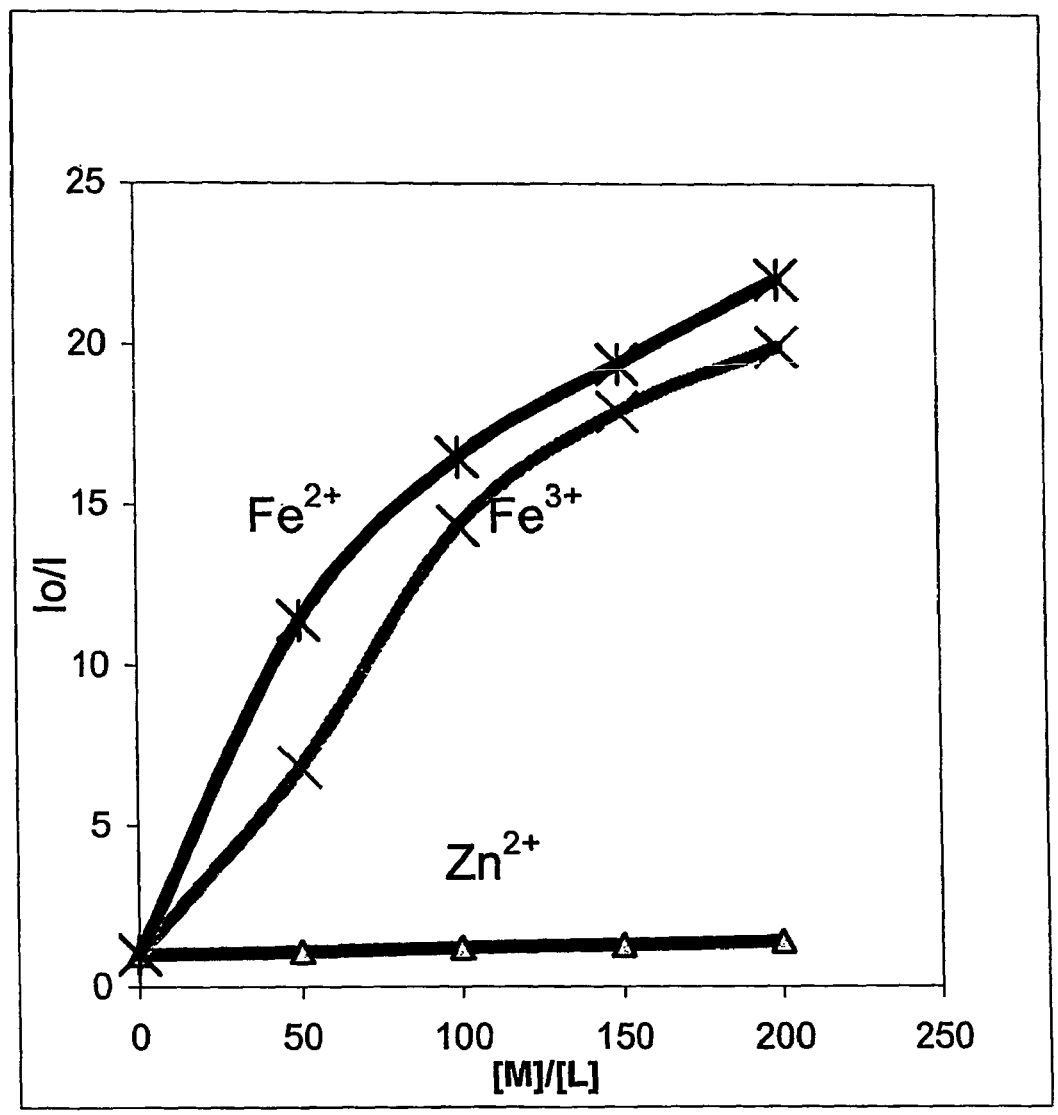
FIG. 34 depicts a Stern-Volmer plots for syn-18 in presence of $Zn^{2+}$, $Fe^{2+}$ and $Fe^{3+}$.
Figure 35:
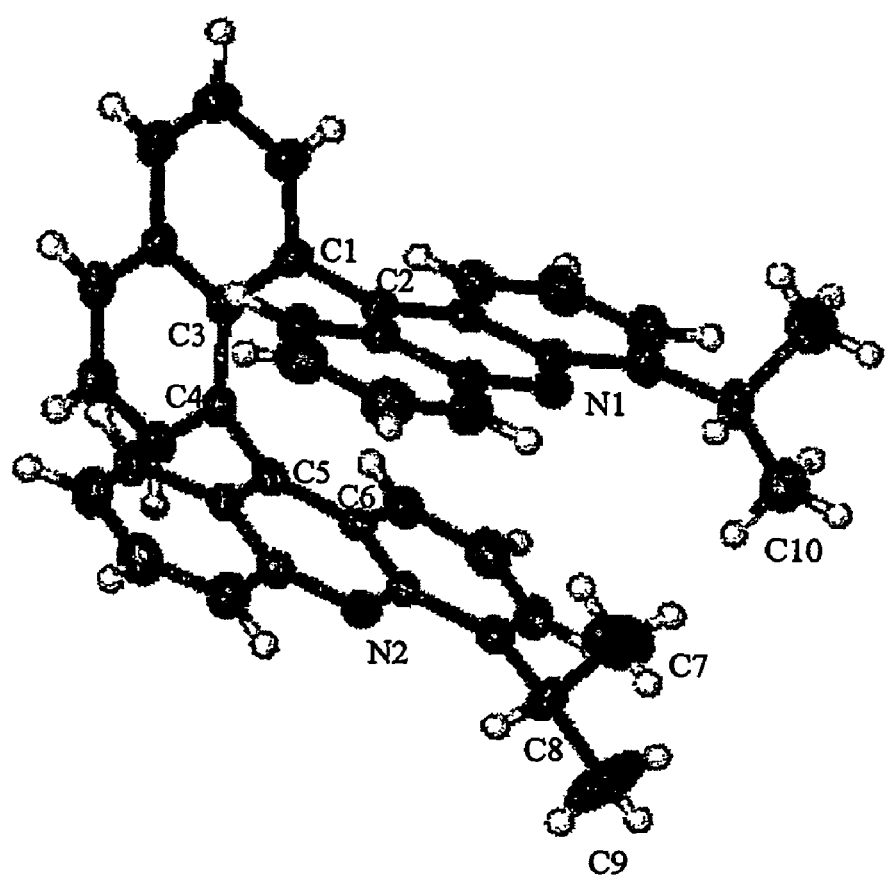
FIG. 35 depicts a single crystal structure of syn-19. (Crystal system: Monoclinic, Space group: $P2_1/n$; Selected bond lengths (Å): C1-C2: 1.4807, C4-C5: 1.499, N1-N2: 4.028, C7-C10: 3.865; Selected torsion angles: C3-C4-C5-C6: 101.30, C1-C2-C4-C5: 21.8°).
Figure 36:
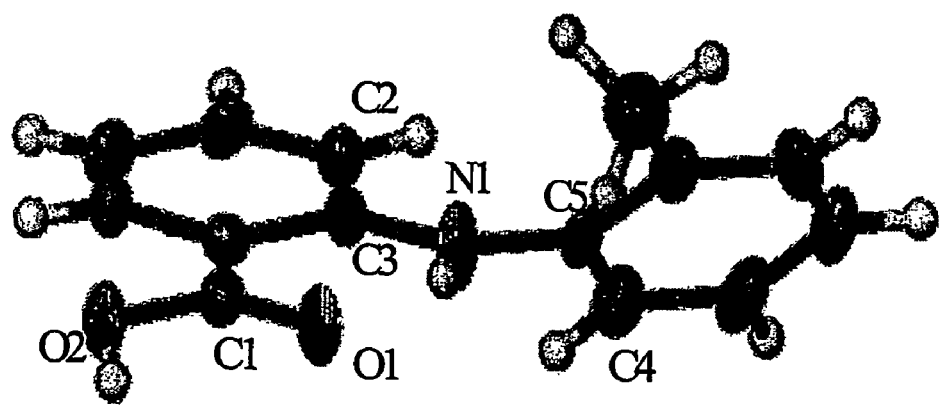
FIG. 36 depicts a single crystal structure of 2-(2'-Methylphenylamino)benzoic Acid 25 (Crystal system: Monoclinic Space group: $C2_1/c$; Selected bond lengths: (Å) C1-O1: 1.238, C1-O2: 1.323, C3-N1: 1.369, C5-N1: 1.414; Torsion angle: C2-C3-C4-C5: 134.1°).
Figure 37:
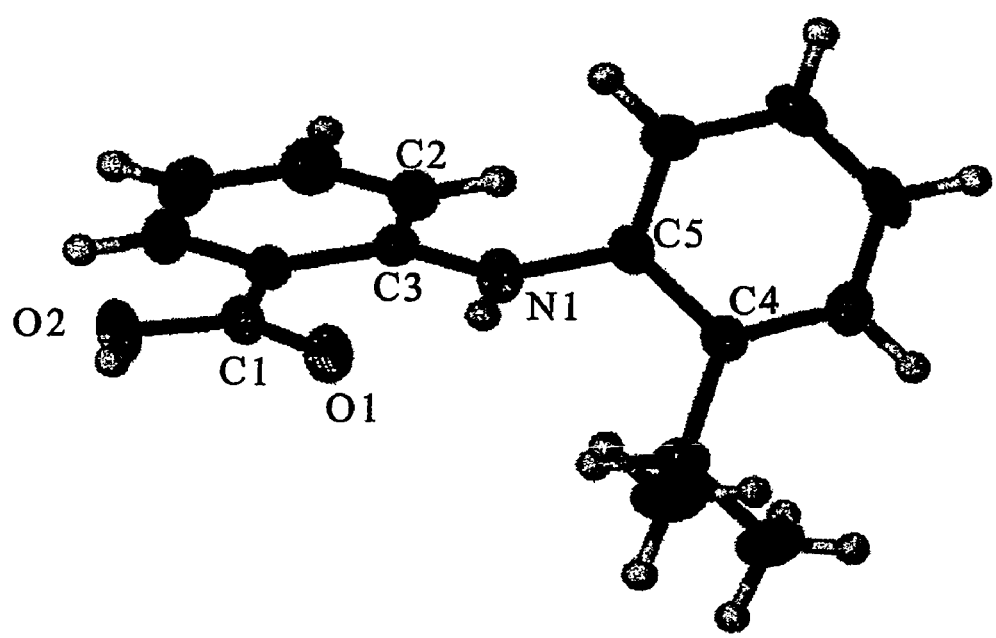
FIG. 37 depicts a single crystal structure of 2-(2'-Isopropylphenylamino)benzoic Acid 24 (Crystal system: Triclinic, Space group: P-1; Select bond lengths (Å): C1-O1: 1.236, C1-O2: 1.324, C3-N1: 1.371, C5-N1: 1.417; Torsion angle: C2-C3-C4-C5: 81.4°).

Based on the $C_2$-Symmetry of 33, we decided to employ chiral bidentate analytes 34 and 35 in fluorescence titration experiments. Titration studies using one isolated enantiomer of 33 at $3.5 \times 10^{-5}$ M (excitation at 475 nm, emission maximum at 571 nm) and various amounts of (R)- and (S)-N-t-Boc-valine, 33, in toluene showed enantioselective fluorescence quenching and a remarkably high enantioselectivity factor ($K^S_{sv}/K^R_{sv}$) of 1.63, FIG. 29. Moreover, the change of the fluorescence response of N,N'-dioxide 33 in the presence of $5.9 \times 10^{-3}$ M N-t-Boc-valine was found to decrease linearly as the enantiopurity of (S)-34 increases, FIG. 30. By contrast, Stern-Vömer plots using trans-1,2-diaminocyclohexane, 35, in acetonitrile (excitation at 475 nm, emission maximum at 571 nm) revealed enantioselective fluorescence enhancement and an enantioselectivity factor ($K^{RR}_{sv}/K^{SS}_{sv}$) of 1.50, FIG. 31.

The data indicate the usefulness of sensors such as 33 for enantioselective sensing of hydrogen bond donors including alcohols, carboxylic acids, and amines. Based on our crystallographic data and PM3 calculations we postulate that the sensor's well-defined coordination geometry and $C_2$-symmetry allow rationalization and thus prediction of enantiodifferentiation. While the 3,5-dimethylphenyl groups occupy two quadrants of the coordination sphere of 33 and thus define its enantioselective cleft, the other two quadrants remain unoccupied (open). Coordination of a bidentate hydrogen bond donor such as 34 will be favored if the approaching enantiomer can place its isopropyl group into an open quadrant of the sensor while maintaining a preferentially populated low energy conformation, FIG. 31. Thus, (R,R)-33 is expected to form a more stable diastereomeric complex with (R)-34, whereas (s)-34 experiences considerable steric repulsion because its isopropyl group is directed to an occupied quadrant of the selector, i.e. formation of an (R,R)-33-(S)-34 adduct is energetically disfavored. While fluorescence enhancement is not well understood, enantioselective fluorescence quenching of excited N,N'-dioxide 33 in presence of amino acid 34 may be attributed to static quenching (i.e. constant fluorescence lifetimes) via non-radiative relaxation of diastereomeric hydrogen-bond adducts. We therefore assume that (R)-34 is a more effective fluorescence quencher of (R,R)-33 than (S)-34.

In sum, the linear fluorescence quenching effect in presence of N-t-Boc-valine was attributed to static quenching via non-radiative relaxation of diastereomeric hydrogen-bond complexes. The high sensitivity inherent to fluorescence spectroscopy combined with the considerable stereoselectivity of this new class of chemosensors affords a new tool for real-time analysis of the enantiomeric composition of chiral compounds. We assume that this new class of bidentate ligands provides a promising venue for developing new asymmetric Lewis acid and Lewis base catalysts. Axially chiral 1,8-diacridylnaphthalene N,N'-dioxides for enantioselective fluorosensing of mono- and bifunctional chiral compounds and applications in asymmetric catalysis contemplated embodiments of the present invention.

Compounds of the Invention

One aspect of the present invention relates to a compound represented by formula I:

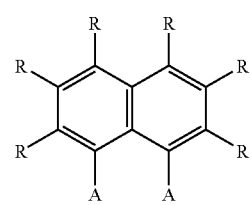

I wherein

R represents independently for each occurrence H, alkyl, aryl, aralkyl, or alkenyl; and A represents independently for each occurrence aryl or heteroaryl.

In certain embodiments, the present invention relates to compound I, wherein R represents independently for each occurrence H or alkyl.

In certain embodiments, the present invention relates to compound I, wherein A is heteroaryl.

In certain embodiments, the present invention relates to compound I, wherein A is heteroaryl, and R represents independently for each occurrence H or alkyl.

In certain embodiments, the present invention relates to compound I, wherein A is selected from the group consisting of:

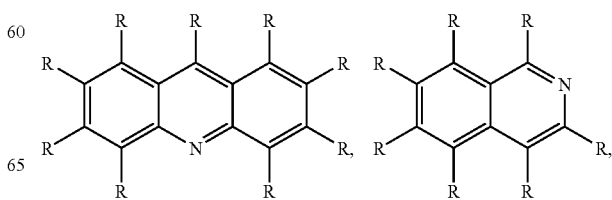

-continued

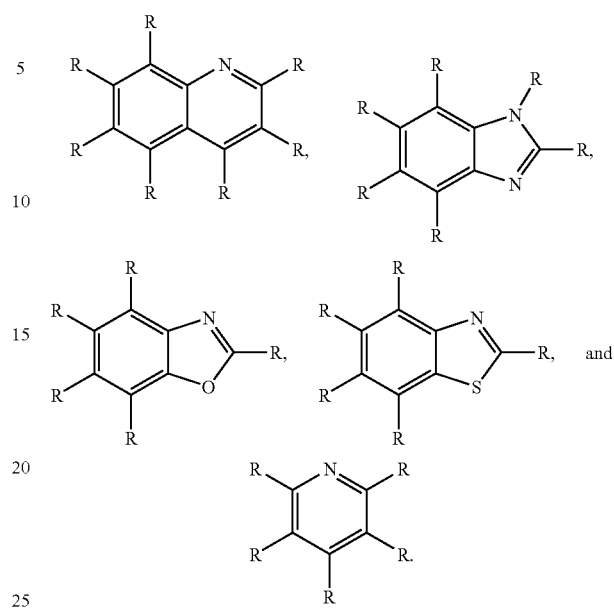

wherein

R represents independently for each occurrence H, alkyl, aryl, or a bond to the naphthyl ring of the compound represented by formula I.

Another aspect of the present invention relates to a compound represented by formula II:

II

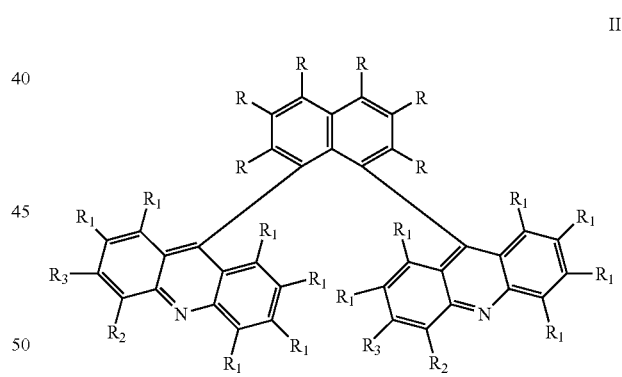

wherein

R, $R_1$, $R_2$, and $R_3$ represent independently for each occurrence H, alkyl, aryl, aralkyl, or alkenyl.

In certain embodiments, the present invention relates to compound II, wherein R represents independently for each occurrence H or alkyl.

In certain embodiments, the present invention relates to compound II, wherein R represents independently for each occurrence H.

In certain embodiments, the present invention relates to compound II, wherein $R_1$ represents independently for each occurrence H or alkyl.

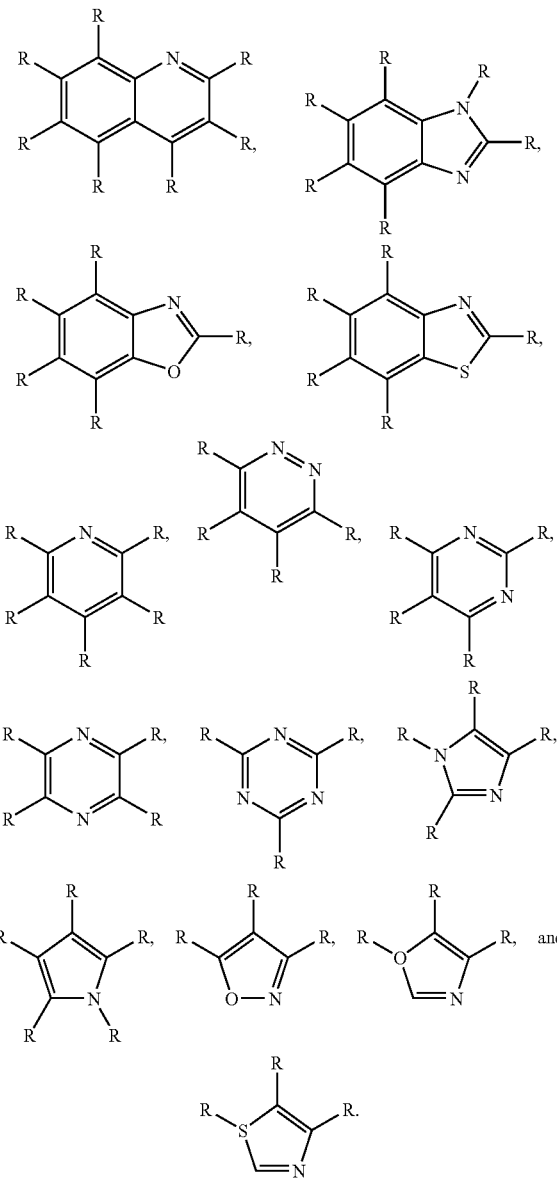

wherein

R represents independently for each occurrence H, alkyl, aryl, or a bond to the naphthyl ring of the compound represented by formula I.

In certain embodiments, the present invention relates to compound I, wherein A is selected from the group consisting of:

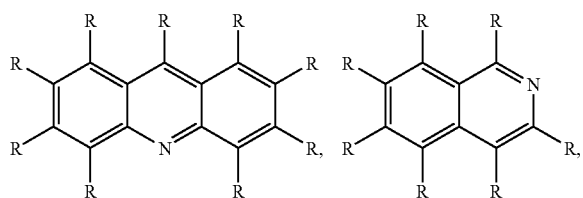

In certain embodiments, the present invention relates to compound II, wherein $R_1$ represents independently for each occurrence H.

In certain embodiments, the present invention relates to compound II, wherein $R_2$ represents independently for each occurrence H, alkyl, or aryl.

In certain embodiments, the present invention relates to compound II, wherein $R_2$ represents independently for each occurrence alkyl.

In certain embodiments, the present invention relates to compound II, wherein $R_2$ represents independently for each occurrence methyl, ethyl, propyl, isopropyl, butyl, isobutyl, sec-butyl, or pentyl.

In certain embodiments, the present invention relates to compound II, wherein $R_2$ represents independently for each occurrence methyl or isopropyl.

In certain embodiments, the present invention relates to compound II, wherein $R_3$ represents independently for each occurrence H, alkyl, or aryl.

In certain embodiments, the present invention relates to compound II, wherein $R_3$ represents independently for each occurrence aryl.

In certain embodiments, the present invention relates to compound II, wherein $R_3$ represents independently for each occurrence an optionally substituted phenyl group.

In certain embodiments, the present invention relates to compound II, wherein $R_3$ represents independently for each occurrence 3,5-dimethylphenyl.

In certain embodiments, the present invention relates to compound II, wherein R is H, $R_1$ is H, $R_3$ is H, and $R_2$ is alkyl.

In certain embodiments, the present invention relates to compound II, wherein R is H, $R_1$ is H, $R_3$ is H, and $R_2$ is methyl, ethyl, propyl, isopropyl, butyl, isobutyl, sec-butyl, or pentyl.

In certain embodiments, the present invention relates to compound II, wherein R is H, $R_1$ is H, $R_3$ is H, and $R_2$ is methyl.

In certain embodiments, the present invention relates to compound II, wherein R is H, $R_1$ is H, $R_3$ is H, and $R_2$ is isopropyl.

In certain embodiments, the present invention relates to compound II, wherein R is H, $R_1$ is H, $R_2$ is H, and $R_3$ represents independently for each occurrence aryl.

In certain embodiments, the present invention relates to compound II, wherein R is H, $R_1$ is H, $R_2$ is H, and $R_3$ represents independently for each occurrence an optionally substituted phenyl group.

In certain embodiments, the present invention relates to compound II, wherein R is H, $R_1$ is H, $R^2$ is H, and $R_3$ is 3,5-dimethylphenyl.

In certain embodiments, the present invention relates to compound II, wherein said compound is a chiral.

In certain embodiments, the present invention relates to compound II, wherein said compound is a single diastereomer.

Another aspect of the present invention relates to a compound represented by formula III:

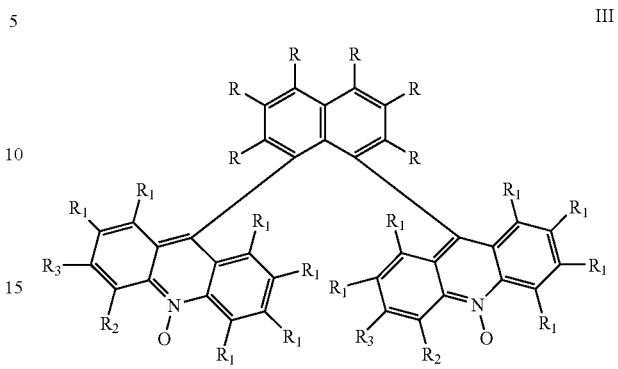

wherein
R, $R_1$, $R_2$, and $R_3$ represent independently for each occurrence H, alkyl, aryl, aralkyl, or alkenyl.

In certain embodiments, the present invention relates to compound III, wherein R represents independently for each occurrence H or alkyl.

In certain embodiments, the present invention relates to compound III, wherein R represents independently for each occurrence H.

In certain embodiments, the present invention relates to compound III, wherein $R_1$ represents independently for each occurrence H or alkyl.

In certain embodiments, the present invention relates to compound III, wherein $R_1$ represents independently for each occurrence H.

In certain embodiments, the present invention relates to compound III, wherein $R_2$ represents independently for each occurrence H, alkyl, or aryl.

In certain embodiments, the present invention relates to compound III, wherein $R_2$ represents independently for each occurrence alkyl.

In certain embodiments, the present invention relates to compound III, wherein $R_2$ represents independently for each occurrence methyl, ethyl, propyl, isopropyl, butyl, isobutyl, sec-butyl, or pentyl.

In certain embodiments, the present invention relates to compound III, wherein $R_3$ represents independently for each occurrence H, alkyl, or aryl.

In certain embodiments, the present invention relates to compound III, wherein $R_3$ represents independently for each occurrence aryl.

In certain embodiments, the present invention relates to compound III, wherein $R_3$ represents independently for each occurrence an optionally substituted phenyl group.

In certain embodiments, the present invention relates to compound III, wherein $R_3$ represents independently for each occurrence 3,5-dimethylphenyl.

In certain embodiments, the present invention relates to compound III, wherein R is H, $R_1$ is H, $R_3$ is H, and $R_2$ is alkyl.

In certain embodiments, the present invention relates to compound III, wherein R is H, $R_1$ is H, $R_3$ is H, and $R_2$ is methyl, ethyl, propyl, isopropyl, butyl, isobutyl, sec-butyl, or pentyl.

In certain embodiments, the present invention relates to compound III, wherein R is H, $R_1$ is H, $R_3$ is H, and $R_2$ is methyl.

In certain embodiments, the present invention relates to compound III, wherein R is H, $R_1$ is H, $R_3$ is H, and $R_2$ is isopropyl.

In certain embodiments, the present invention relates to compound III, wherein R is H, $R_1$ is H, $R_2$ is H, and $R_3$ represents independently for each occurrence aryl.

In certain embodiments, the present invention relates to compound III, wherein R is H, $R_1$ is H, $R_2$ is H, and $R_3$ represents independently for each occurrence an optionally substituted phenyl group.

In certain embodiments, the present invention relates to compound III, wherein R is H, $R_1$ is H, $R_2$ is H, and $R_3$ is 3,5-dimethylphenyl.

In certain embodiments, the present invention relates to compound III, wherein said compound is a single enantiomer.

Methods of the Invention

One aspect of the present invention relates to a method of detecting and quantifying an analyte in a sample, comprising the steps of:

contacting a sample optionally comprising an analyte with a compound of formula II; measuring the fluorescence of said compound II in said sample; and comparing said fluoresence measurement to the fluoresence of said compound II in the absence of said sample.

In certain embodiments, the present invention relates to the aforementioned method, wherein the analyte is a cation.

In certain embodiments, the present invention relates to the aforementioned method, wherein the analyte is a alkali, alkaline earth, or transition metal ion.

In certain embodiments, the present invention relates to the aforementioned method, wherein the analyte is a alkali or alkaline earth metal ion.

In certain embodiments, the present invention relates to the aforementioned method, wherein the analyte is a lithium, sodium, potassium, magnesium, calcium, or strontium metal ion.

In certain embodiments, the present invention relates to the aforementioned method, wherein the analyte is a sodium, potassium, or calcium metal ion.

In certain embodiments, the present invention relates to the aforementioned method, wherein the analyte is a transition metal ion.

In certain embodiments, the present invention relates to the aforementioned method, wherein the analyte is a copper, iron, nickel, manganese, cobalt, chromium, vanadium, titanium, zirconium, rhodium, palladium, silver, cadmium, mercury, gold, platinum, or hafnium ion.

In certain embodiments, the present invention relates to the aforementioned method, wherein the analyte is a copper, iron, nickel, or manganese ion.

In certain embodiments, the present invention relates to the aforementioned method, wherein the analyte is a copper ion.

In certain embodiments, the present invention relates to the aforementioned method, wherein the analyte is a $Cu^{2+}$.

In certain embodiments, the present invention relates to the aforementioned method, wherein said compound of formula II is as defined in any one of the above embodiments.

Another aspect of the present invention relates to a method of detecting and quantifying an analyte in a sample, comprising the step of:

contacting a sample optionally comprising an analyte with a compound of formula II or III; measuring the fluorescence of said compound II or III in said sample; and comparing said fluoresence measurement to the fluoresence of said compound II or III in the absence of said sample.

In certain embodiments, the present invention relates to the aforementioned method, wherein the analyte is a compound that comprises a hydrogen atom capable of participating in a hydrogen bond.

In certain embodiments, the present invention relates to the aforementioned method, wherein the analyte is a compound that comprises a hydroxyl, carboxylic acid, amine, amide, thiol, or percarboxylic acid functional group.

In certain embodiments, the present invention relates to the aforementioned method, wherein the analyte is a compound that comprises a hydroxyl, carboxylic acid, or amine functional group.

In certain embodiments, the present invention relates to the aforementioned method, wherein the analyte is a compound that comprises a hydroxyl functional group.

In certain embodiments, the present invention relates to the aforementioned method, wherein the analyte is a compound that comprises a carboxylic acid functional group.

In certain embodiments, the present invention relates to the aforementioned method, wherein the analyte is a chiral compound that comprises a hydrogen atom capable of participating in a hydrogen bond.

In certain embodiments, the present invention relates to the aforementioned method, wherein the analyte is a chiral compound that comprises a hydroxyl, carboxylic acid, amine, amide, thiol, or percarboxylic acid functional group.

In certain embodiments, the present invention relates to the aforementioned method, wherein the analyte is a chiral compound that comprises a hydroxyl, carboxylic acid, or amine functional group.

In certain embodiments, the present invention relates to the aforementioned method, wherein the analyte is a chiral compound that comprises a hydroxyl functional group.

In certain embodiments, the present invention relates to the aforementioned method, wherein the analyte is a chiral compound that comprises a carboxylic acid functional group.

In certain embodiments, the present invention relates to the aforementioned method, wherein said compound of formula II or III is as defined in any one of the above embodiments.

In certain embodiments, the present invention relates to the aforementioned method, wherein said compound of formula II or III wherein R is H, $R_1$ is H, $R_2$ is H, and $R_3$ represents independently for each occurrence aryl.

DEFINITIONS

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

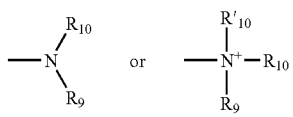

wherein $R_9$, $R_{10}$ and $R'_{10}$ each independently represent a group permitted by the rules of valence.

The term "acylamino" is art-recognized and refers to a moiety that can be represented by the general formula:

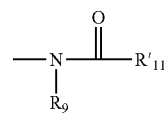

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

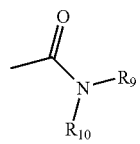

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

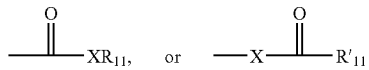

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

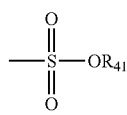

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

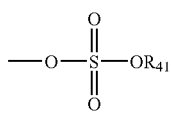

in which R$_{41}$ is as defined above.

The term "sulfonylamino" is art recognized and includes a moiety that can be represented by the general formula:

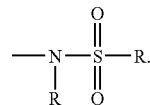

The term "sulfamoyl" is art-recognized and includes a moiety that can be represented by the general formula:

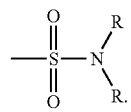

The term "sulfonyl", as used herein, refers to a moiety that can be represented by the general formula:

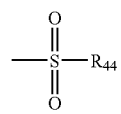

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

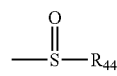

in which R$_{44}$ is selected from the group consisting of hydrogen, alkyl, alkenyl, alknyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_7$, m and R$_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2nd* ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Combinatorial Libraries

The subject compounds may be synthesized using the methods of combinatorial synthesis described in this section. Combinatorial libraries of the compounds may be used for the screening of pharmaceutical, agrochemical or other biological or medically-related activity or material-related qualities. A combinatorial library for the purposes of the present invention is a mixture of chemically related compounds which may be screened together for a desired property, said libraries may be in solution or covalently linked to a solid support. The preparation of many related compounds in a single reaction greatly reduces and simplifies the number of screening processes which need to be carried out Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical liability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

General Procedures

All reaction were carried out under nitrogen. Commercially available reagents and solvents were used without further purification. Flash chromatography was carried out on silica gel (particle size 0.032-0.063 mm). NMR spectra were obtained at 300 MHz ($^1$H NMR) and 75 MHz ($^{13}$C NMR) using CDCl$_3$ as the solvent. Chemical shifts are reported in ppm relative to TMS. Elemental analysis data were collected using a Perkin Elmer 2400 CHN. UV measurements were performed on an Agilent 8453 UV-Visible spectrometer. Extinction coefficients were determined from 5 different measurements in CH$_2$Cl$_2$. Absorption and emission spectra were collected under nitrogen. Fluorescence experiments were conducted using a Fluoromax-2 from Instruments S.A. Inc. Quantum yields of 2 and 3 were determined in benzene following literature procedures. See Jones II, G.; Jackson, W. R.; Choi, C.-Y. *J. Phys. Chem.* 1985, 89, 294-300. 1,8-Bis(4,4'-dialkyl-9,9'-diacridyl)naphthalenes were excited at 381 nm and relative integrated intensities of the emission spectra were compared to anthracene. The quantum efficiency of anthracene in benzene (25.6%) was taken from the literature.

Synthetic Procedures 1,8-Bis(4,4'-dimethyl-9,9'-diacridyl)naphthalene, 2

A mixture 1,8-dibromonaphthanene 1 (92 mg, 0.32 mmol), tetrakis(triphenylphosphine)palladium(0) (0.11 g, 0.10 mmol, 30 mol %), and CuO (51 mg, 0.64 mmol) in 10 mL DMF was stirred at 140° C. After 5 min, a solution of 4-methyl-9-trimethylstannanyl acridine 12 (0.46 g, 1.29 mmol) dissolved in 2 mL of DMF was added in one portion. After 16 hours, the reaction mixture was quenched with 10% aqueous ammonium hydroxide, extracted with diethyl ether, dried over MgSO$_4$ and concentrated in vacuo. Purification of the orange residue by flash chromatography (100:5:1 hexanes:ethyl acetate:triethylamine) afforded 2 (41 mg, 25%) as a yellow solid. The diastereoisomers were separated on a Phenylglycine column (250 mm×4.6 mm) using hexanes/EtOH (98:2) as the mobile phase. The anti- and syn-conformation of the two isomer of 2 was determined by $^1$H-NMR spectroscopy using 1.2 mol equivalents of (+)-Eu(tfc)$_3$ as a chiral shift reagent. anti-Isomer: $^1$H-NMR δ=2.72 (s, 6H), 6.50 (d, J=8.8 Hz, 1H), 6.52 (d, J=8.8 Hz, 1H), 6.58-6.78 (m, 6H), 7.18 (d, J=6.6 Hz, 2H), 7.22-7.27 (m, 2H), 7.35 (ddd, J=1.7 Hz, J=7.8 Hz, J=8.8 Hz, 2H), 7.68-7.73 (m, 4H), 8.25 (dd, J=1.3 Hz, J=8.8 Hz, 2H). $^{13}$C-NMR δ=18.87, 123.75, 124.67, 125.00, 125.70, 125.74, 128.18, 128.37, 129.72, 129.87, 130.58, 130.73, 134.37, 135.10, 135.90, 146.73, 146.81, 146.04, 146.32. LC/APCI/MS: m/z=511 (M+H). syn-Isomer: $^1$H-NMR δ=2.67 (s, 6H), 6.45-6.52 (m, 2H), 6.58-6.70 (m, 4H), 6.80 (d, J=8.8 Hz 2H), 7.20-7.40 (m, 6H), 7.65-7.78 (m, 4H), 8.25 (dd, J=1.3 Hz, J=8.8 Hz, 2H). $^{13}$C-NMR δ=18.94, 123.42, 124.67, 125.00, 125.73, 125.76, 128.21, 128.41, 129.73, 129.85, 130.58, 130.73, 134.37, 135.10, 135.90, 146.72, 146.81, 146.04, 146.32. LC/APCI/MS: m/z=511 (M+H). Anal. calcd. for syn and anti-$C_{38}H_{26}N_2$: C, 89.38; H, 5.13; N, 5.49. Found: C, 89.80; H, 5.57; N, 4.99.

1,8-Bis(4,4'-diisopropyl-9,9'-diacridyl)naphthlalene, 3

A mixture 1,8-dibromonaphthanene 1 (10.25 g, 0.89 mmol), tetrakis(triphenylphosphine)palladium(0) (0.31 g, 0.27 mmol, 30 mol %), and CuO (0.14 g, 1.78 mmol) in 18 mL DMF was stirred at 140° C. After 5 min, a solution of 4-isopropyl-9-trimethylstannanyl acridine 12 (1.45 g, 3.8 mmol) dissolved in 2 mL DMF was added in one portion. After 16 hours, the reaction mixture was quenched with 10% aqueous ammonium hydroxide, extracted with diethyl ether, dried over $MgSO_4$ and concentrated in vacuum. Purification of the orange residue by flash chromatography (100:5:1 hexanes:ethyl acetate:trimethylamine) afforded 3 (126 mg, 25%) as a yellow solid. The diastereoisomers were separated on a Phenylglycine column (250 mm×4.6 mm) using hexanes/EtOH (98.4:1.6) as the mobile phase. Isomer 1: $^1$H-NMR δ=1.22 (d, J=6.9 Hz, 6H), 1.52 (d, J=6.9 Hz, 6H), 4.23 (sept, J=6.9 Hz, 2H), 6.60-6.70 (m, 6H), 6.85 (d, J=8.4 Hz, 2H), 7.18-7.30 (m, 6H), 7.60-7.78 (m, 4H), 8.26 (dd, J=1.6 Hz, J=8.4 Hz, 2H). $^{13}$C-NMR δ=24.38, 27.25, 27.33, 123.58, 123.96, 124.68, 124.74, 124.74, 125.54, 125.58, 125.87, 128.21, 129.72, 129.90, 130.92, 134.93, 135.10, 144.95, 145.01, 145.61, 145.97, 146.79. LC/APCI/MS: m/z=567 (M+H). Isomer 2: $^1$H-NMR δ=1.22 (d, J=6.9 Hz, 6H), 1.52 (d, J=6.9 Hz, 6H), 4.23 (sept, J=6.9 Hz, 2H), 6.59-6.78 (m, 6H), 7.20-7.37 (m, 8H), 7.64-7.72 (m, 4H), 8.26 (dd, J=1.6 Hz, J=8.4 Hz, 2H). $^{13}$C-NMR δ=24.62, 26.98, 27.08, 123.54, 123.95, 124.60, 124.71, 125.16, 125.52, 125.74, 128.09, 129.69, 129.93, 130.79, 134.59, 134.70, 144.95, 145.01, 145.57, 145.77, 146.79. LC/APCI/MS: m/z=567 (M+H). Anal. calcd. for syn and anti-$C_{42}H_{34}N_2$: C, 89.01; H, 6.05; N, 4.94. Found: C, 89.38; H, 6.25; N, 4.67.

2-(2'-Methylphenylamino)benzoic acid, 7

A mixture of 2-methylaniline (2.68 g, 25 mmol), 2-chlorobenzoic acid (3.8 g, 24 mmol), $K_2CO_3$ (4.1 g, 30 mmol), Cu powder (0.05 g), $Cu_2O$ (0.05 g), and 5 mL 2-methoxyethanol was refluxed for 2 hours. The cooled reaction mixture was poured into 30 mL water. Charcoal was then added and the solution was filtrated through Celite. The crude product was obtained by acidification of the filtrate with diluted HCl at ambient temperature, and subsequent recrystallization from acetone/water (1/8). The crystals were dissolved in 100 mL 5% aqueous $Na_2CO_3$. The solution was filtered through Celite and the product was precipitated by acidification to afford acid 7 (3.0 g, 55%) as a white powder. $^1$H-NMR δ=2.29 (s, 3H), 6.72 (bs, 1H), 6.85 (d, J=8.2 Hz, 2H) 7.12 (dd, J=7.2 Hz, J=7.4 Hz, 1H), 7.20-7.34 (m, 5H), 8.05 (d, J=7.2 Hz, 1H), 9.18 (bs, 1H). $^{13}$C-NMR=18.96, 114.4, 117.3, 125.67, 125.98, 127.22, 127.49, 131.61, 131.85, 134.10, 135.79, 135.97, 139.16, 150.35.

2-(2'-Isopropylphenylamino)benzoic acid, 8

A mixture of 2-isopropylaniline (3.4 g, 25 mmol), 2-chlorobenzoic acid (3.8 g, 24 mmol), $K_2CO_3$ (4.1 g, 30 mmol), Cu powder (0.05 g), $Cu_2O$ (0.05 g), in 5 mL 2-methoxyethanol was refluxed for 2 hours. The cooled reaction mixture was poured into 30 mL water. Charcoal was then added and the solution was filtered through Celite. The crude product was obtained by acidification of the filtrate with diluted HCl at ambient temperature, and subsequent recrystallization from acetone/water (1/8). The crystals were dissolved in 100 mL 5% aqueous $Na_2CO_3$, filtered through Celite and the crystals were recrystallized by acidification to yield acid 8 (4.4 g, 73%) as a white powder. $^1$H-NMR δ=1.22 (d, J=6.9 Hz, 6H), 3.21 (sept, J=6.9 Hz, 1H), 4.68 (bs, 1H), 6.68 (dd, J=7.2 Hz, J=7.4 Hz, 1H), 6.81 (d, J=8.2 Hz, 1H), 7.22-7.40 (m, 4H), 8.1 (dd, J=1.7 Hz, J=8.2 Hz, 1H), 9.18 (s, 1H). $^{13}$C-NMR δ=23.97, 28.83, 114.38, 117.09, 126.72, 126.90, 127.13, 127.31, 133.08, 135.68, 136.04, 137.84, 145.09, 151.20, 174.73.

9-Bromo-4-methylacridine, 9

2-(2'-Methylphenylamino)benzoic acid 7 (1.0 g, 4.4 mmol) was suspended in 11.0 g (38 mmol) of phosphorus oxybromide, and the mixture was heated to 120° C. for 2 hours. Excess phosphorus oxybromide was removed by distillation and the residual solution was poured into a 1:1 mixture of aqueous ammonium hydroxide:$CH_2Cl_2$. The $CH_2Cl_2$ solution was separated, dried, filtered, and the combined organic layers were dried in vacuo to give 9 (1.0 g, 85%) as a yellow powder. $^1$H-NMR δ=2.94 (s, 3H), 7.53 (dd, J=8.5 Hz, J=8.8 Hz, 1H), 7.59-7.69 (m, 2H), 7.78 (ddd, J=1.4 Hz, J=8.5 Hz, J=8.5 Hz, 1H), 8.28 (dd, J=8.5 Hz, J=8.5 Hz, 2H), 8.43 (dd, J=1.4 Hz, J=8.8 Hz, 1H). $^{13}$C-NMR δ=19.48, 126.37, 128.49, 128.76, 129.07, 129.28, 129.72, 130.95, 131.15, 131.88, 135.87, 138.12, 148.43, 148.71. Anal. calcd. for $C_{14}H_{10}NBr$: C, 61.79; H, 3.70; N, 5.15. Found: C, 61.40; H, 3.72; N, 5.05.

9-Bromo-4-isopropyl-acridine, 10

2-(2'-Isopropylphenylamino)benzoic acid 8 (1.0 g, 3.9 mmol) was suspended in 11.0 g (38 mmol) of phosphorus oxybromide, and the mixture was heated to 120° C. for 2 hours. Excess phosphorus oxybromide was removed by distillation and the residual solution was poured into a 1:1 mixture of aqueous ammonium hydroxide:$CH_2Cl_2$. The $CH_2Cl_2$ solution was separated, dried, filtered, and the combined organic layers was dried in vacuum to give 10 (1.2 g, 79%) as yellow powder. $^1$H-NMR δ=1.45 (d, J=6.9 Hz, 6H), 4.56 (sept, J=6.9 Hz, 1H), 7.56-7.70 (m, 3H), 7.78 (ddd, J=1.5 Hz, J=6.6 Hz, J=6.6 Hz, 1H), 8.24 (d, J=8.4 Hz, 1H), 8.29 (dd, J=1.5 Hz, J=8.5 Hz, 1H), 8.41 (d, J=8.8 Hz, 1H). $^{13}$C-NMR δ=24.00, 28.21, 125.20, 125.62, 125.86, 126.49, 127.38, 127.64, 129.90, 130.58, 130.83, 135.69, 147.44, 148.01, 148.14. Anal. calcd. for $C_{16}H_{14}NBr$: C, 64.02; H, 4.70; N, 4.67. Found: C, 64.23; H, 4.78; N, 4.59.

4-Methyl-9-trimethylstannanylacridine, 11

A solution of 9-bromo-4-methylacridine 9 (1 g, 3.7 mmol) in 50 ml anhydrous diethyl ether was cooled to −78° C. under nitrogen. To the solution was added 1.6 M n-BuLi in hexanes (0.74 mmol, 0.46 mL) dropwise over a period of 15 min and a 1.0 M solution of $Me_3SnCl$ in hexanes (0.81 mL, 0.81 mmol). The reaction solution mixture was allowed to warm to room temperature, stirred for 18 hours and concentrated in vacuo. Purification of the orange residue by flash chromatography (100:10:1 hexanes:ethyl acetate:triethyl amine) afforded 11 (1.1 g, 84%) as a yellow solid. GC-MS revealed contamination of the product with 5-10% 4-methylacridine that could not be separated by chromatography. The stannane was therefore employed in the Stille coupling with 1,8-dibromonaphthalene without further purification. $^1$H-NMR δ=0.67 (s, 9H), 2.95 (s, 3H), 7.41 (dd, J=6.9 Hz, J=8.8 Hz, 1H), 7.52 (ddd, J=1.4 Hz, J=6.5 Hz, J=6.5 Hz, 1H), 7.61 (d, J=6.9 Hz, 1H), 7.74 (ddd, J=1.4 Hz, J=7.4 Hz, J=7.4 Hz, 1H), 7.97 (d, J=7.9 Hz, 1H), 8.12 (d, J=9.3 Hz, 1H), 8.28 (d, J=7.9 Hz, 1H). $^{13}$C-NMR δ=−4.63, 19.51, 125.33, 125.56, 128.42, 128.94, 129.30, 129.93, 131.38, 133.49, 133.62, 138.58, 147.36, 147.53, 156.78.

4-Isopropyl-9-trimethylstannylacridine, 12

Stannane 12 (1.4 g, 3.5 mmol) was obtained in 90% yield using 9-bromo-4-isopropyl-acridine 10 (1.2 g, 3.9 mmol), 1.6 M n-BuLi in hexanes (2.6 mL, 4.2 mmol) and a 1.0 M solution of $Me_3SnCl$ in hexanes (4.5 mL, 4.5 mmol) following the procedure described for the preparation of 11. GC-MS revealed contamination of the product with 5-10% 4-isopropylacridine that could not be separated by chromatography. The stannane was therefore employed in the Stille coupling with 1,8-dibromonaphthalene without further purification. $^1$H-NMR δ=0.71 (s, 9H), 1.51 (d, J=6.9 Hz, 6H), 4.69 (sept, J=6.9 Hz, 1H), 7.48-7.60 (m, 2H), 7.67 (d, J=6.4 Hz, 1H), 7.76 (ddd, J=1.4 Hz, J=6.0 Hz, J=6.0 Hz, 1H), 8.02 (dd, J=1.1 Hz, J=8.6 Hz, 1H), 8.16 (d, J=8.5 Hz, 1H), 8.33 (d, J=8.8 Hz, 1H). $^{13}$C-NMR δ=−4.05, 24.05, 28.02, 124.77, 125.37, 125.50, 128.05, 129.05, 129.95, 131.71, 1 33.33, 133.72, 146.16, 147.18, 148.72, 156.59.

Example 2

General Procedures

All reactions were carried out under nitrogen. Commercially available reagents and solvents were used without further purification. 1,8-Dibromonaphthalene was prepared from 1,8-diaminonaphthalene as described in the literature. Seyferth, D.; Vick, S. C. *J. Organomet. Chem.* 1977, 141, 178-187. Flash chromatography was performed on silica gel (particle size 0.032-0.063 mm). NMR spectra were obtained at 300 MHz ($^1$H NMR) and 75 MHz ($^{13}$C NMR) using $CDCl_3$ as the solvent. Chemical shifts are reported in ppm relative to TMS. Elemental analysis data were collected using a Perkin Elmer 2400 CHN. Fluorescence experiments were conducted using a Fluoromax-2 from Instruments S.A. Inc. Absorption and emission spectra were collected under nitrogen. Circular dichroism spectra were obtained in hexane/ethyl alcohol 4:1 using a JASCO J-710 circular dichroism chiroptical spectrometer. Atmospheric pressure chemical ionization (APCI) mass spectra were collected on a YMC-Pack CN column (4.6×250 mm) using an HP 1100 HPLC/MSD equipped with electrospray and atmospheric pressure chemical ionization MS detection and hexanes/EtOH=9:1 as the mobile phase. Chiral HPLC was carried out on an HP 1050 equipped with an autosampler and DAD detector using a Chiralpak AD column (250 mm×4.6 mm, 5 μm) and hexanes/ethyl alcohol (4:1) as the mobile phase. Preparative separations were performed by repetitive injections of 50 μL of 16 dissolved in hexanes/EtOH (1:1) at a concentration of approximately 20 mg/mL. For analytical separations, 2 was dissolved in the same diluent at a concentration of 1 mg/mL and 10 μL were injected. Single crystal X-ray diffractions of N,N'-dioxide 16 were performed at −90° C. ($16CH_2Cl_2$) and −87° C. ($16-H_2O—CH_3CN$) using a Siemens platform diffractometer with graphite monochromated Mo—Kα radiation (λ=0.71073 Å). The structures were solved by direct methods and refined with full-matrix least-squares/difference Fourier analysis using SHELX-97-2 software. Non-hydrogen atoms were refined with anisotropic displacement parameters and all hydrogen atoms were placed in calculated positions and refined with a riding model. Data were corrected for the affects of absorption using SADABS. Crystal data, collection parameters, refinement details, and key molecular parameters are shown in FIG. 28.

Synthetic Procedures 3-(3,5-dimethylphenyl)aniline, 9

To a solution of 3-bromoaniline, 8, (17.2 g, 0.10 mol), 3,5-dimethylphenylboronic acid (16.5 g, 0.11 mol), CsF (50 g, 0.33 mol), $Pd_2(dba)_3$ (0.92 g, 5 mmol) in 50 mL anhydrous THF was added a solution of $P(t-Bu)_3$ (0.49 g, 2.4 mmol) in 3 mL of THF. The exothermal reaction was cooled using a water bath. The solution mixture was stirred at room temperature for 2 hours and concentrated in vacuo. The residue was dissolved in methylene chloride and washed with water. The combined organic layers were dried over $MgSO_4$ and solvents were evaporated. Purification of the orange residue by flash chromatography (100:10:1 hexanes:ethyl acetate:triethylamine) afforded 9 (20.0 g, 99%) as a brown oil. $^1$H-NMR δ=2.30 (s, 6H), 3.53 (bs, 2H), 6.50 (dd, J=2.5 Hz, 7.1 Hz, 1H), 6.77 (d, J=1.6 Hz, 2.2 Hz, 1M), 6.91 (s, 1H), 6.94 (dd, J=1.2 Hz, 2.5 Hz, 1H), 7.10-7.15 (m, 3H). $^{13}$C-NMR δ=22.2, 115.4, 119.3, 125.7, 129.5, 130.2, 138.7, 141.8, 143.3, 145.7. Anal. calcd. for $C_{14}H_{15}N$: C, 85.28; H, 7.61; N, 7.11. Found: C, 85.61; H, 8.01; N, 7.00.

N-3-(3,5-dimethylphenyl)anthranilic acid, 11

A mixture of 3-(3,5-dimethylphenyl)aniline 9 (5.3 g, 27 mmol), 2-chlorobenzoic acid, 10, (4.2 g, 27 mmol), $K_2CO_3$ (4.1 g, 30 mmol), Cu powder (0.05 g), and $Cu_2O$ (0.05 g), in 5 mL of 2-methoxyethanol was refluxed for 2 hours. The cooled reaction mixture was poured into 30 mL water. Charcoal was then added and the solution was filtrated through Celite. The crude product was obtained by acidification of the filtrate with diluted HCl at ambient temperature, and subsequent recrystallization from acetone/water (1:8). The crystals were dissolved in 100 mL 5% aqueous $Na_2CO_3$. The solution was filtered through Celite and the product was precipitated by acidification to afford acid 11 (8.1 g, 95%) as a light yellow powder. $^1$H-NMR δ=2.39 (s, 6H), 4.43 (s, 2H), 6.77 (dd, J=7.1 Hz, 7.6 Hz, 1H), 7.02 (s, 1H), 7.22-7.50 (m, 8H), 8.06 (d, J=8.0 Hz, 1H). $^{13}$C-NMR δ=21.7, 113.7, 114.4, 115.9, 117.5, 121.9, 122.1, 123.1, 125.2, 128.7, 129.3, 129.8, 133.9, 135.3, 138.5, 140.9, 143.0, 149.1. Anal. calcd. for $C_{21}H_{19}NO_2$: C, 79.50; H, 5.99; N, 4.42. Found: C, 79.10; H, 6.23; N, 4.32.

9-bromo-3-(3,5-dimethylphenyl)acridine, 12

Acid 11 (1.0 g, 3.15 mmol) was suspended in 11.0 g (38 mmol) of phosphorus oxybromide, and the mixture was heated to 120° C. for 2 hours. Excess phosphorus oxybromide was removed by distillation and the residual solution was poured into a 1:1 mixture of aqueous ammonium hydroxide: $CH_2Cl_2$. The $CH_2Cl_2$ solution was separated, dried, and dried in vacuo. Purification of the orange residue by flash chromatography (100:100:1 hexanes:methylene chloride:triethylamine) gave 12 (0.5 g, 45%) as a yellow powder. $^1$H-NMR δ=2.44 (s, 6H), 7.09 (s, 1H), 7.46 (s, 2H), 7.63 (ddd, J=1.1 Hz, 6.6 Hz, 8.8 Hz, 1H), 8.28 (dd, J=8.5 Hz, 6.9 Hz, 1H), 7.92 (dd, J=1.6 Hz, 9.1 Hz, 1H), 8.22 (d, J=8.8 Hz, 1H) 8.39-8.47 (m, 3H). $^{13}$C-NMR δ=22.0, 125.3, 125.5, 126.0, 126.7, 127.0, 127.2, 127.5, 127.8, 129.9, 130.2, 130.4, 135.4, 138.6, 139.3, 142.8, 149.2, 149.2. Anal. calcd. for $C_{21}H_{16}NBr$: C, 69.61; H, 4.42; N, 3.87. Found: C, 70.03; H, 4.30; N, 3.40.

3-(3,5-dimethylphenyl)-9-trimethylstannylacridine, 13

A solution of 9-bromo-3-(3,5-dimethylphenyl)acridine, 12, (0.6 g, 1.6 mmol) in 10 ml anhydrous diethyl ether:THF (1:1) was cooled to −78° C. To the solution was added 1.6 M n-BuLi in hexanes (2.4 mmol, 1.5 mL) dropwise over a period of 15 min and then a 1.0 M solution of $Me_3SnCl$ in hexanes (3 mL, 3 mmol). The reaction mixture was allowed to warm to room temperature, stirred for 18 hours and concentrated in vacuo. Purification of the orange residue by flash chromatography (100:30:1 hexanes:ethyl acetate:triethylamine) afforded 13 (0.65 g, 91%) as a yellow solid. GC-MS revealed contamination of the product with 5-10% 3-(3,5-dimethylphenyl)acridine that could not be separated by chromatography. The stannane was therefore employed in the Stille cross-coupling with 1,8-dibromonaphthalene without further purification. $^1$H-NMR δ=0.70 (s, 9H), 2.44 (s, 6H), 7.08-7.10 (m, 1H), 7.49-7.56 (m, 3H), 7.76 (ddd, J=1.4 Hz, 6.6 Hz, 8.8 Hz, 1H), 7.88 (dd, J=1.9 Hz, 9.1 Hz, 1H), 8.13 (d, J=8.5 Hz, 1H), 8.22 (d, J=9.1 Hz, 1H), 8.27 (d, J=8.5 Hz, 1H), 8.49 (m, 1H). $^{13}$C-NMR δ=4.2, 21.8, 125.3, 125.4, 125.5, 127.7, 129.6, 129.8, 130.1, 130.4, 130.8, 132.8, 133.5, 138.4, 139.8, 142.0, 148.2, 148.2, 156.4.

1,8-bis(3,3'-(3,5-dimethylphenyl)-9,9'-diacridyl) naphthalene, 15

A mixture of 1,8-dibromonaphthalene, 14, (143 mg, 0.50 mmol), tetrakis(tiphenylphosphine)palladium(0) (0.11 g, 0.10 mmol, 30 mol %), and CuO (80 mg, 1 mmol) in 5 mL DMF was stirred at 140° C. After 5 min, a solution of 3-(3, 5-dimethylphenyl)-9-trimethylstannylacridine 13 (0.90 g, 2.0 mmol) in 2 mL of DMF was added in one portion. After 16 hours, the reaction mixture was quenched with 10% aqueous ammonium hydroxide, extracted with diethyl ether, dried over $MgSO_4$ and concentrated in vacuo. Purification of the orange residue by flash chromatography (100:5:1 hexanes: ethyl acetate:triethylamine) afforded 15 (100 mg, 30%) as a yellow solid. The diastereoisomers were separated into 60% of the anti-isomer and 40% of the syn-isomer. anti-Isomer: $^1$H-NMR δ=2.45 (s, 12H), 6.62-6.68 (m, 2H), 6.83-6.86 (m, 4H), 7.00-7.03 (m, 2H), 7.07 (s, 2H), 7.31-7.39 (m, 8H), 7.67 (d, J=9.1 Hz, 2H), 7.73-7.78 (m, 2H), 7.91 (s, 2H). 8.31 (d, J=8.2 Hz, 2l). $^{13}$C-NMR δ=22.3, 124.8, 125.4, 125.5, 125.6, 125.9, 126.2, 126.3, 126.6, 127.0, 129.3, 129.8, 130.1, 130.5, 131.2, 134.2, 134.6, 135.5, 139.0, 140.8, 141.9, 146.1, 147.5, 147.6. LC/APCI/MS: m/z=691 (M+H). Anal. calcd. for anti-$C_{52}H_{38}N_2$: C, 90.43; H, 5.55; N, 4.06. Found: C, 90.64; H, 5.30; N, 4.11. syn-Isomer. $^1$H-NMR 3=2.26 (s, 12H), 6.65-6.70 (m, 2H), 6.75-6.78 (m, 2H), 6.85-6.88 (m, 2H), 6.96-6.99 (m, 4H), 7.12 (s, 4H), 7.28-7.31 (m, 2l), 7.36-7.42 (m, 2H), 7.69-7.75 (m, 4H), 7.91 (d, J=1.65 Hz, 2H), 8.27 (dd, J=1.1 Hz, 8.36 Hz, 2H). $^{13}$C-NMR δ=22.0, 124.8, 125.3, 125.4, 125.5, 125.8, 126.1, 126.3, 126.4, 126.9, 129.4, 129.7, 130.1, 130.4, 131.1, 134.2, 134.7, 135.5, 138.8, 140.7, 142.1, 146.1, 147.4, 147.5. Anal. calcd. for syn-$C_{52}H_{38}N_2$: C, 90.43; H, 5.55; N, 4.06. Found: C, 90.70; H, 5.40; N, 4.36.

1,8-bis(3,3'-(3,5-dimethylphenyl)-9,9'-diacridyl) naphthalene N,N'-dioxide, 16

A solution of 1,8-bis(3,3'-(3,5-dimethylphenyl)-9,9'-diacridyl)naphthalene, 15, (100 mg, 0.15 mmol) in 3 mL of THF was treated with perbenzoic acid (68 mg, 77% purity, 0.30 mmol) in 2 mL of THF at room temperature. The mixture was allowed to stir at room temperature for 5 hours and the solvent was removed by evaporation under reduced pressure. The residue was dissolved in methylene chloride and washed with 2N sodium hydroxide, dried over $MgSO_4$ and concentrated in vacuo. Purification by flash chromatography (100:10 ethyl acetate:ethyl alcohol) afforded 1 (80 mg, 75%) as a red solid. $^1$H-NMR δ=2.45 (s, 12H), 6.63-6.69 (m, 2H), 6.81 (d, J=9.1 Hz, 2H), 6.87 (d, J=8.0 Hz, 2H), 7.09-7.14 (m, 4H), 7.34-7.41 (m, 8H), 7.77 (dd, J=7.2 Hz, 8.2 Hz, 2H), 8.32 (dd, J=1.1 Hz, 8.2 Hz 2H), 8.47 (d, J=9.1 Hz 2H). 8.69 (d, J=1.7 Hz, 2ll). $^{13}$C-NMR δ=22.3, 117.6, 120.5, 126.1, 126.5, 126.5, 126.6, 126.7, 126.3, 126.9, 127.5, 130.0, 130.7, 131.0, 132.2, 133.4, 134.1, 135.1, 135.9, 138.6, 138.6, 139.2, 140.2, 143.0. Anal. calcd. for $C_{52}H_{38}N_2O_2$: C, 86.43; H, 5.26; N, 3.88. Found: C, 86.40; H, 5.33; N, 3.76.

Example 3

General Procedures

All reactions were carried out under nitrogen. Commercially available reagents and solvents were used without further purification. 1,8-Dibromonaphthalene was prepared from 1,8-diaminonaphthalene as described in the literature (Seyferth, D.; Vick, S. C. *J. Organomet. Chem.* 1977, 141, 178-187). Flash chromatography was performed on silica gel particle size 0.032-0.063 mm). NMR spectra were obtained at 300 MHz ($^1$H NMR) and 75 MHz ($^{13}$C NMR) using $CDCl_3$ as the solvent. Chemical shifts are reported in ppm relative to TMS. Elemental analysis data were collected using a Perkin Elmer 2400 CHN. Atmospheric pressure chemical ionization (APCI) mass spectra were collected on a YMC-Pack CN column (4.6×250 mm) using an HP 1100 HPLC/MSD equipped with electrospray and atmospheric pressure chemical ionization MS detection and hexanes/EtOH (9:1) as the mobile phase.

Synthetic Procedures 3-(3,5-Dimethylphenyl)aniline, 26

To a solution of 3-bromoaniline, 25, (17.2 g, 0.10 mol), 3,5-dimethylphenylboronic acid (16.5 g, 0.11 mol), CsF (50 g, 0.33 mol), $Pd_2(dba)_3$ (0.92 g, 5 mmol) in 50 mL anhydrous THF was added a solution of P(t-Bu)$_3$ (0.49 g, 2.4 mmol) in 3 mL of THF. The exothermal reaction was cooled using a water bath. The solution mixture was stirred at room temperature for 2 hours and concentrated in vacuo. The residue was dissolved in methylene chloride and washed with water. The combined organic layers were dried over $MgSO_4$ and solvents were evaporated. Purification of the orange residue by flash chromatography (100:10:1 hexanes:ethyl acetate:triethylamine) afforded 26 (20.0 g, 99%) as a brown oil. $^1$H-NMR δ=2.30 (s, 6H), 3.53 (bs, 2H), 6.50 (dd, J=2.5 Hz, 7.1 Hz, 1H), 6.77 (d, J=1.6 Hz, 2.2 Hz, 1H), 6.91 (s, 1H), 6.94 (dd, J=1.2 Hz, 2.5 Hz, 1H), 7.10-7.15 (m, 3H). $^{13}$C-NMR δ=22.2, 115.4, 119.3, 125.7, 129.5, 130.2, 138.7, 141.8, 143.3, 145.7. Anal. calcd. for $C_{14}H_{15}N$: C, 85.28; H, 7.61; N, 7.11. Found: C, 85.61; H, 8.01; N, 7.00.

N-3-(3,5-Dimethylphenyl)anthranilic acid, 28

A mixture of 3-(3,5-dimethylphenyl)aniline 26 (5.3 g, 27 mmol), 2-chlorobenzoic acid 27 (4.2 g, 27 mmol), $K_2CO_3$ (4.1 g, 30 mmol), Cu powder (0.05 g), and $Cu_2O$ (0.05 g), in 5 mL of 2-methoxyethanol was refluxed for 2 hours. The cooled reaction mixture was poured into 30 mL water. Charcoal was then added and the solution was filtrated through Celite. The crude product was obtained by acidification of the filtrate with diluted HCl at ambient temperature, and subsequent recrystallization from acetone/water (1:8). The crystals were dissolved in 100 mL 5% aqueous $Na_2CO_3$. The solution was filtered through Celite and the product was precipitated by acidification to afford acid 28 (8.1 g, 95%) as a light yellow powder. $^1$H-NMR δ=2.39 (s, 6H), 4.43 (s, 2H), 6.77 (dd, J=7.1 Hz, 7.6 Hz, 1H), 7.02 (s, 1H), 7.22-7.50 (m, 8H), 8.06 (d, J=8.0 Hz, 1H). $^{13}$C-NMR δ=21.7, 113.7, 114.4, 115.9, 117.5, 121.9, 122.1, 123.1, 125.2, 128.7, 129.3, 129.8, 133.9, 135.3, 138.5, 140.9, 143.0, 149.1. Anal. calcd. for $C_{21}H_{19}NO_2$: C, 79.50; H, 5.99; N, 4.42. Found: C, 79.10; H, 6.23; N, 4.32.

9-Bromo-3-(3,5-dimethylphenyl)acridine, 29

Acid 28 (1.0 g, 3.15 mmol) was suspended in 11.0 g (38 mmol) of phosphorus oxybromide, and the mixture was heated to 120° C. for 2 hours. Excess phosphorus oxybromide was removed by distillation and the residual solution was poured into a 1:1 mixture of aqueous ammonium hydroxide:$CH_2Cl_2$. The $CH_2Cl_2$ solution was separated, dried, and dried in vacuo. Purification of the orange residue by flash chromatography (100:100:1 hexanes:methylene chloride:triethylamine) gave 29 (0.5 g, 45%) as a yellow powder. $^1$H-NMR δ=2.44 (s, 6H), 7.09 (s, 1H), 7.46 (s, 2H), 7.63 (ddd, J=1.1 Hz, 6.6 Hz, 8.8 Hz, 1H), 8.28 (dd, J=8.5 Hz, 6.9 Hz, 1H), 7.92 (dd, J=1.6 Hz, 9.1 Hz, 1H), 8.22 (d, J=8.8 Hz, 1H) 8.39-8.47 (m, 3H). $^{13}$C-NMR δ=22.0, 125.3, 125.5, 126.0, 126.7, 127.0, 127.2, 127.5, 127.8, 129.9, 130.2, 130.4, 135.4, 138.6, 139.3, 142.8, 149.2, 149.2. Anal. calcd. for $C_{21}H_{16}NBr$: C, 69.61; H, 4.42; N, 3.87. Found: C, 70.03; H, 4.30; N, 3.40.

3-(3,5-Dimethylphenyl)-9-trimethylstannylacridine, 30

A solution of 9-bromo-3-(3,5-dimethylphenyl)acridine, 29, (0.6 g, 1.6 mmol) in 10 ml anhydrous diethyl ether:THF (1:1) was cooled to –78° C. To the solution was added 1.6 M n-BuLi in hexanes (2.4 mmol, 1.5 mL) dropwise over a period of 15 min and then a 1.0 M solution of $Me_3SnCl$ in hexanes (3 mL, 3 mmol). The reaction mixture was allowed to warm to room temperature, stirred for 18 hours and concentrated in vacuo. Purification of the orange residue by flash chromatography (100:30:1 hexanes:ethyl acetate:triethylamine) afforded 30 (0.65 g, 91%) as a yellow solid. GC-MS revealed contamination of the product with 5-10% 3-(3,5-dimethylphenyl)acridine that could not be separated by chromatography. The stannane was therefore employed in the Stille cross-coupling with 1,8-dibromonaphthalene without filter purification. $^1$H-NMR δ=0.70 (s, 9H), 2.44 (s, 6H), 7.08-7.10 (m, 1H), 7.49-7.56 (m, 3H), 7.76 (ddd, J=1.4 Hz, 6.6 Hz, 8.8 Hz, 1H), 7.88 (dd, J=1.9 Hz, 9.1 Hz, 1H), 8.13 (d, J=8.5 Hz, 1H), 8.22 (d, J=9.1 Hz, 1H), 8.27 (d, J=8.5 Hz, 1H), 8.49 (m, 1H). $^{13}$C-NMR δ=−4.2, 21.8, 125.3, 125.4, 125.5, 127.7, 129.6, 129.8, 130.1, 130.4, 130.8, 132.8, 133.5, 138.4, 139.8, 142.0, 148.2, 148.2, 156.4.

1,8-Bis(3,3'-(3,5-dimethylphenyl)-9,9'-diacridyl) naphthalene, 32

A mixture of 1,8-dibromonaphthalene (143 mg, 0.50 mmol), tetrakis(triphenylphosphine)-palladium(0) (0.11 g, 0.10 μmol, 30 mol %), and CuO (80 mg, 1 mmol) in 5 mL DMF was stirred at 140° C. After 5 min, a solution of 3-(3,5-dimethylphenyl)-9-trimethylstannylacridine 31 (0.90 g, 2.0 mmol) in 2 mL of DMF was added in one portion. After 16 hours, the reaction mixture was quenched with 10% aqueous ammonium hydroxide, extracted with diethyl ether, dried over $MgSO_4$ and concentrated in vacuo. Purification of the orange residue by flash chromatography (100; 5:1 hexanes:ethyl acetate:triethylamine) afforded 32 (100 mg, 30%) as a yellow solid. The diastereoisomers were separated into 60% of the anti-isomer and 40% of the syn-isomer. anti-Isomer: $^1$H-NMR δ=2.45 (s, 12H), 6.62-6.68 (m, 2H), 6.83-6.86 (m, 4H), 7.00-7.03 (m, 2H), 7.07 (s, 2H), 7.31-7.39 (m, 8H), 7.67 (d, J=9.1 Hz, 2H), 7.73-7.78 (m, 2H), 7.91 (s, 2H). 8.31 (d, J=8.2 Hz, 2H). $^{13}$C-NMR δ=22.3, 124.8, 125.4, 125.5, 125.6, 125.9, 126.2, 126.3, 126.6, 127.0, 129.3, 129.8, 130.1, 130.5, 131.2, 134.2, 134.6, 135.5, 139.0, 140.8, 141.9, 146.1, 147.5, 147.6. LC/APC/MS: m/z=691 (M+H). Anal. calcd. for anti-$C_{52}H_{38}N_2$: C, 90.43; H, 5.55; N, 4.06. Found: C, 90.64; H, 5.30; N, 4.11. syn-Isomer: $^1$H-NMR δ=2.26 (s, 12H), 6.65-6.70 (m, 2H), 6.75-6.78 (m, 2H), 6.85-6.88 (m, 2H), 6.96-6.99 (m, 4H), 7.12 (s, 4H), 7.28-7.31 (m, 2H), 7.36-7.42 (m, 2H), 7.69-7.75 (m, 4H), 7.91 (d, J=1.65 Hz, 2H), 8.27 (dd, J=1.1 Hz, 8.36 Hz, 2H). $^{13}$C-NMR δ=22.0, 124.8, 125.3, 125.4, 125.5, 125.8, 126.1, 126.3, 126.4, 126.9, 129.4, 129.7, 130.1, 130.4, 131.1, 134.2, 134.7, 135.5, 138.8, 140.7, 142.1, 146.1, 147.4, 147.5. Anal. calcd. for syn-$C_{52}H_{38}N_2$: C, 90.43; H, 5.55; N, 4.06. Found: C, 90.70; H, 5.40; N, 4.36.

anti-1,8-bis(3,3'-(3,5-dimethylphenyl)-9,9-diacridyl) naphthalene N,N'-dioxide, 33

A solution of anti-32, (100 mg, 0.15 mmol) in 3 mL of THF was treated with perbenzoic acid (68 mg, 77% purity, 0.30 mmol) in 2 mL of THF at room temperature. The mixture was allowed to stir at room temperature for 5 hours and the solvent was removed by evaporation under reduced pressure. The residue was dissolved in methylene chloride and washed with 2N sodium hydroxide, dried over $MgSO_4$ and concentrated in vacuo. Purification by flash chromatography (100:10 ethyl acetate:ethyl alcohol) afforded 33 (80 mg, 75%) as a red solid. $^1$H-NMR (300 MHz, $CDCl_3$) δ=2.45 (s, 12H), 6.63-6.69 (m, 2H), 6.81 (d, J=9.1 Hz, 2H), 6.87 (d, J=8.0 Hz, 2H), 7.09-7.14 (m, 4H), 7.34-7.41 (m, 8H), 7.77 (dd, J=7.2 Hz, 8.2 Hz, 2H), 8.32 (dd, J=1.1 Hz, 8.2 Hz 2H), 8.47 (d, J=9.1 Hz 2H). 8.69 (d, J=1.7 Hz, 2H). $^{13}$C-NMR (75 MHz, $CDCl_3$) δ=22.3, 117.6, 120.5, 126.1, 126.5, 126.5, 126.6, 126.7, 126.3, 126.9, 127.5, 130.0, 130.7, 131.0, 132.2, 133.4, 134.1, 135.1, 135.9, 138.6, 138.6, 139.2, 140.2, 143.0. Anal. calcd. for $C_{52}H_{38}N_2O_2$: C, 86.43; H, 5.26; N, 3.88. Found: C, 86.40; H, 5.33; N, 3.76.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula I:

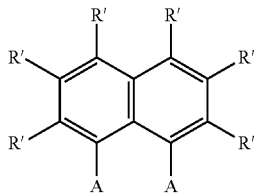

wherein
R' represents independently for each occurrence H, alkyl, aryl, aralkyl, or alkenyl;
A is selected from the group consisting of:

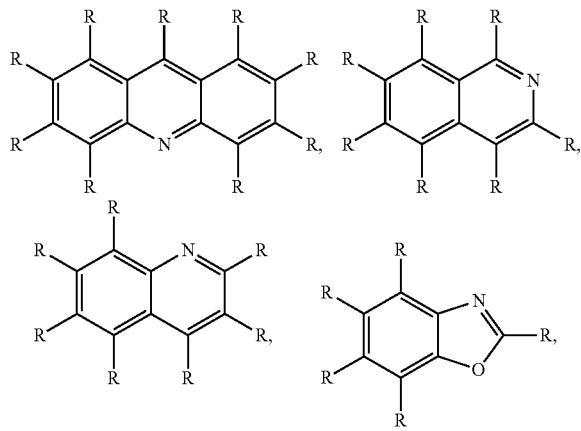

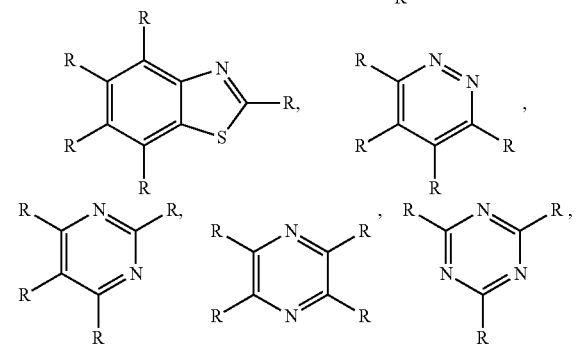

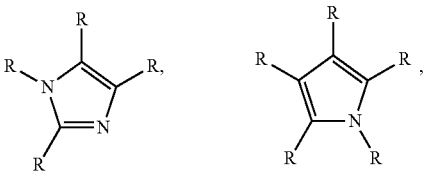

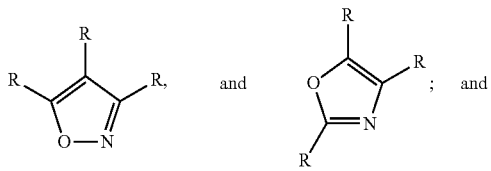

R represents independently for each occurrence H, alkyl, aryl, or a bond to the naphthyl ring of the compound represented by formula I.

2. The compound of claim 1, wherein R' represents independently for each occurrence H or alkyl.

3. The compound of claim 1, wherein A is selected from the group consisting of:

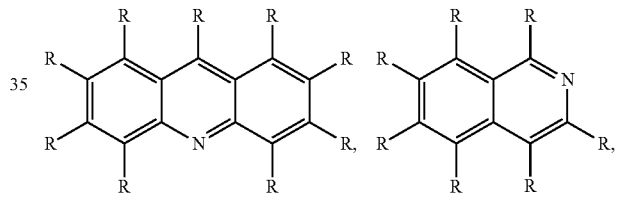

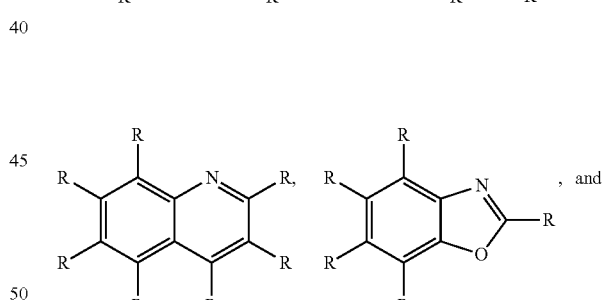

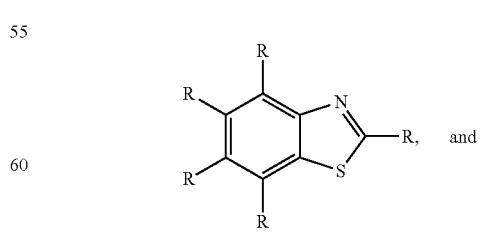

R represents independently for each occurrence H, alkyl, aryl, or a bond to the naphthyl ring of the compound represented by formula I.

4. A compound represented by formula II:

II wherein
R, $R_1$, $R_2$, and $R_3$ represent independently for each occurrence H, alkyl, aryl, aralkyl, or alkenyl.

5. The compound of claim 4, wherein R represents independently for each occurrence H or alkyl.

6. The compound of claim 4, wherein R represents independently for each occurrence H.

7. The compound of claim 4, wherein $R_1$ represents independently for each occurrence H or alkyl.

8. The compound of claim 4, wherein $R_1$ represents independently for each occurrence H.

9. The compound of claim 4, wherein $R_2$ represents independently for each occurrence H, alkyl, or aryl.

10. The compound of claim 4, wherein $R_2$ represents independently for each occurrence alkyl.

11. The compound of claim 4, wherein $R_2$ represents independently for each occurrence methyl, ethyl, propyl, isopropyl, butyl, isobutyl, sec-butyl, or pentyl.

12. The compound of claim 4, wherein $R_2$ represents independently for each occurrence methyl or isopropyl.

13. The compound of claim 4, wherein $R_3$ represents independently for each occurrence H, alkyl, or aryl.

14. The compound of claim 4, wherein $R_3$ represents independently for each occurrence aryl.

15. The compound of claim 4, wherein $R_3$ represents independently for each occurrence an optionally substituted phenyl group.

16. The compound of claim 4, wherein $R_3$ represents independently for each occurrence 3,5-dimethylphenyl.

17. The compound of claim 4, wherein R is H, $R_1$ is H, $R_3$ is H, and $R_2$ is alkyl.

18. The compound of claim 4, wherein R is H, $R_1$ is H, $R_3$ is H, and $R_2$ is methyl, ethyl, propyl, isopropyl, butyl, isobutyl, sec-butyl, or pentyl.

19. The compound of claim 4, wherein R is H, $R_1$ is H, $R_3$ is H, and $R_2$ is methyl.

20. The compound of claim 4, wherein R is H, $R_1$ is H, $R_3$ is H, and $R_2$ is isopropyl.

21. The compound of claim 4, wherein R is H, $R_1$ is H, $R_2$ is H, and $R_3$ represents independently for each occurrence aryl.

22. The compound of claim 4, wherein R is H, $R_1$ is H, $R_2$ is H, and $R_3$ represents independently for each occurrence an optionally substituted phenyl group.

23. The compound of claim 4, wherein R is H, $R_1$ is H, $R_2$ is H, and $R_3$ is 3,5-dimethylphenyl.

24. The compound of claim 4, wherein said compound is a chiral.

25. The compound of claim 4, wherein said compound is a single diastereomer.

26. A compound represented by formula III:

III wherein
R, $R_1$, $R_2$, and $R_3$ represent independently for each occurrence H, alkyl, aryl, aralkyl, or alkenyl.

27. The compound of claim 26, wherein R represents independently for each occurrence H or alkyl.

28. The compound of claim 26, wherein R represents independently for each occurrence H.

29. The compound of claim 26, wherein $R_1$ represents independently for each occurrence H or alkyl.

30. The compound of claim 26, wherein $R_1$ represents independently for each occurrence H.

31. The compound of claim 26, wherein $R_2$ represents independently for each occurrence H, alkyl, or aryl.

32. The compound of claim 26, wherein $R_2$ represents independently for each occurrence alkyl.

33. The compound of claim 26, wherein $R_2$ represents independently for each occurrence methyl, ethyl, propyl, isopropyl, butyl, isobutyl, sec-butyl, or pentyl.

34. The compound of claim 26, wherein $R_3$ represents independently for each occurrence H, alkyl, or aryl.

35. The compound of claim 26, wherein $R_3$ represents independently for each occurrence aryl.

36. The compound of claim 26, wherein $R_3$ represents independently for each occurrence an optionally substituted phenyl group.

37. The compound of claim 26, wherein $R_3$ represents independently for each occurrence 3,5-dimethylphenyl.

38. The compound of claim 26, wherein R is H, $R_1$ is H, $R_3$ is H, and $R_2$ is alkyl.

39. The compound of claim 26, wherein R is H, $R_1$ is H, $R_3$ is H, and $R_2$ is methyl, ethyl, propyl, isopropyl, butyl, isobutyl, sec-butyl, or pentyl.

40. The compound of claim 26, wherein R is H, $R_1$ is H, $R_3$ is H, and $R_2$ is methyl.

41. The compound of claim 26, wherein R is H, $R_1$ is H, $R_3$ is H, and $R_2$ is isopropyl.

42. The compound of claim 26, wherein R is H, $R_1$ is H, $R_2$ is H, and $R_3$ represents independently for each occurrence aryl.

43. The compound of claim 26, wherein R is H, $R_1$ is H, $R_2$ is H, and $R_3$ represents independently for each occurrence an optionally substituted phenyl group.

44. The compound of claim 26, wherein R is H, $R_1$ is H, $R_2$ is H, and $R_3$ is 3,5-dimethylphenyl.

45. The compound of claim 26, wherein said compound is a single enantiomer.

46. A compound represented by formula I:

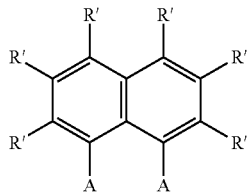

wherein
R' represents independently for each occurrence H, alkyl, aryl, aralkyl, or alkenyl;
A is selected from the group consisting of:

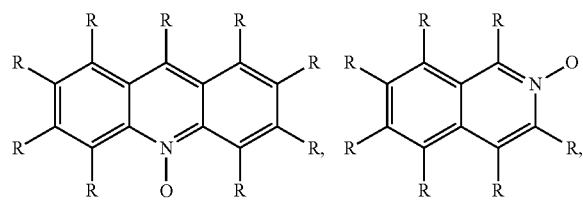

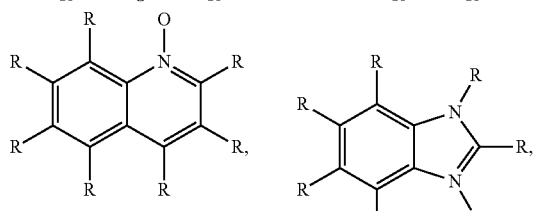

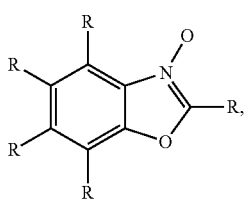

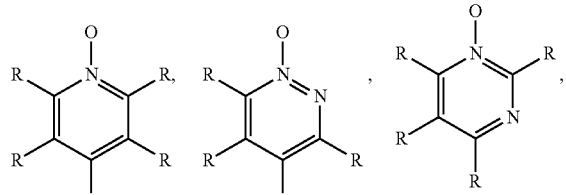

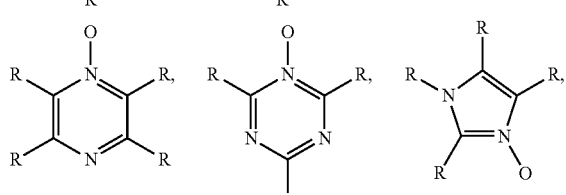

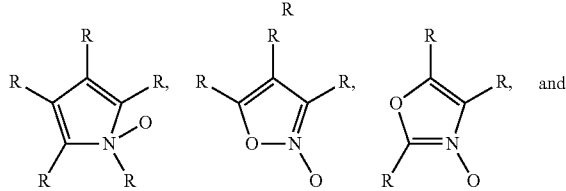

-continued

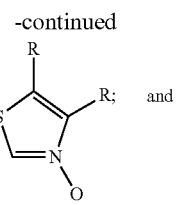

R represents independently for each occurrence H, alkyl, aryl, or a bond to the naphthyl ring of the compound represented by formula I.

47. The compound of claim 46, wherein A is selected from the group consisting of:

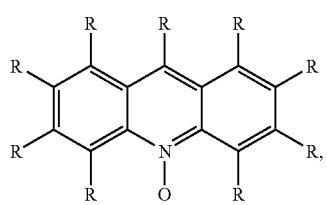

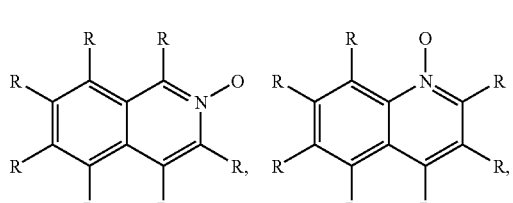

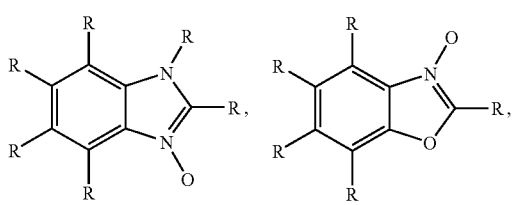

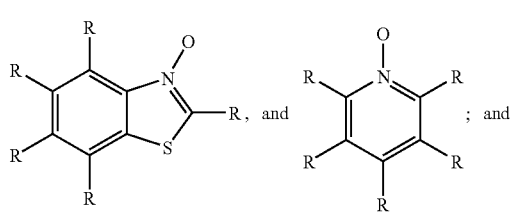

R represents independently for each occurrence H, alkyl, aryl, or a bond to the naphthyl ring of the compound represented by formula I.

48. The compound of claim 1, wherein the compound is represented by:
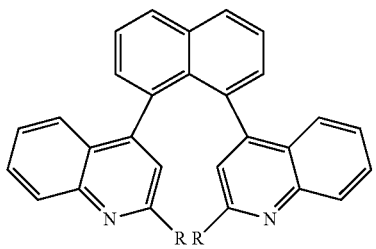
wherein R represents H, alkyl, or aryl.
49. The compound of claim 46, wherein the compound is represented by:
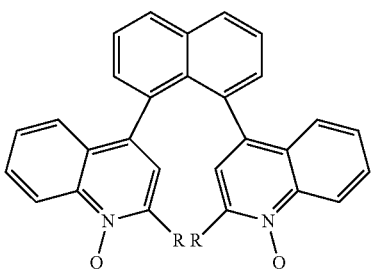
wherein R represents H, alkyl, or aryl.
* * * * *